(12) United States Patent
Maguire

(10) Patent No.: US 12,398,360 B2
(45) Date of Patent: Aug. 26, 2025

(54) CELL ENGINEERING PLATFORM

(71) Applicant: Avectas Limited, Kildare (IE)

(72) Inventor: Michael Maguire, Dublin (IE)

(73) Assignee: AVECTAS LIMITED, County Kildare (IE)

(*) Notice: Subject to any disclaimer, the term of this patent is extended or adjusted under 35 U.S.C. 154(b) by 1221 days.

(21) Appl. No.: 17/059,769

(22) PCT Filed: May 31, 2019

(86) PCT No.: PCT/IB2019/054555
§ 371 (c)(1),
(2) Date: Nov. 30, 2020

(87) PCT Pub. No.: WO2019/229722
PCT Pub. Date: Dec. 5, 2019

(65) Prior Publication Data
US 2021/0261901 A1  Aug. 26, 2021

Related U.S. Application Data

(60) Provisional application No. 62/679,715, filed on Jun. 1, 2018.

(51) Int. Cl.
*C12M 1/42* (2006.01)
*C12M 1/12* (2006.01)
(Continued)

(52) U.S. Cl.
CPC .............. *C12M 35/08* (2013.01); *C12M 3/00* (2013.01); *C12M 25/02* (2013.01);
(Continued)

(58) Field of Classification Search
CPC ....... C12M 35/08; C12M 25/02; C12N 15/87; C12N 15/63
See application file for complete search history.

(56) References Cited

U.S. PATENT DOCUMENTS

| 5,411,208 A | 5/1995 | Burgener |
| 5,534,423 A * | 7/1996 | Palsson .................. C12N 15/87 |
| | | 435/456 |

(Continued)

FOREIGN PATENT DOCUMENTS

| CN | 107206015 A | 9/2017 |
| WO | 2008074980 A1 | 6/2008 |

(Continued)

OTHER PUBLICATIONS

PCT Search Report and Written Opinion issued in connection with corresponding PCT Application No. PCT/IB2019/054555 on Dec. 5, 2019.

(Continued)

*Primary Examiner* — Jonathan M Hurst
(74) *Attorney, Agent, or Firm* — Mintz Levin Cohn Ferris Glovsky and Popeo, P.C.

(57) ABSTRACT

The current subject matter provides a cell engineering platform of a diagnostic and clinical use scale for vector-free and/or viral delivery of payload/cargo compounds and compositions into non-adherent cells. The platform achieves delivery to a large number of cells quickly in a closed system. Related apparatus, systems, techniques, articles and compositions are also described.

39 Claims, 52 Drawing Sheets

(51) Int. Cl.
*C12M 3/00* (2006.01)
*C12N 5/00* (2006.01)
*C12N 5/078* (2010.01)
*C12N 15/87* (2006.01)

(52) U.S. Cl.
CPC ......... *C12N 5/0068* (2013.01); *C12N 5/0634* (2013.01); *C12N 15/87* (2013.01)

(56) References Cited

U.S. PATENT DOCUMENTS

| | | | | |
|---|---|---|---|---|
| 5,654,185 | A * | 8/1997 | Palsson | C12M 25/02 435/235.1 |
| 5,877,023 | A * | 3/1999 | Sautter | C12M 35/04 800/278 |
| 5,914,245 | A | 6/1999 | Bylina et al. | |
| 5,922,687 | A * | 7/1999 | Mann | C12M 41/40 514/44 A |
| 6,093,557 | A * | 7/2000 | Pui | B01J 2/04 435/173.1 |
| 6,472,163 | B1 | 10/2002 | Coleman et al. | |
| 6,634,572 | B1 | 10/2003 | Burgener | |
| 7,667,004 | B2 | 2/2010 | Zhong et al. | |
| 8,697,359 | B1 | 4/2014 | Zhang | |
| 8,779,382 | B1 * | 7/2014 | Tsai | H01T 23/00 250/306 |
| 8,932,814 | B2 | 1/2015 | Cong et al. | |
| 9,023,649 | B2 | 5/2015 | Mali et al. | |
| 9,074,199 | B1 | 7/2015 | Chavez et al. | |
| 10,214,750 | B2 * | 2/2019 | Borenstein | C12M 35/08 |
| 10,562,048 | B2 * | 2/2020 | Chen | B05B 7/061 |
| 2002/0146825 | A1 * | 10/2002 | Uhler | C12N 15/87 435/458 |
| 2003/0092181 | A1 * | 5/2003 | Webb | C12N 15/87 435/285.1 |
| 2005/0170510 | A1 * | 8/2005 | Huang | C12M 35/02 435/459 |
| 2008/0248575 | A1 * | 10/2008 | Lee | C12N 15/87 264/225 |
| 2019/0292510 | A1 * | 9/2019 | Tandon | C12N 15/87 |
| 2021/0284945 | A1 | 9/2021 | Maguire | |
| 2022/0233716 | A1 | 7/2022 | Maguire et al. | |

FOREIGN PATENT DOCUMENTS

| | | |
|---|---|---|
| WO | 2015071474 A3 | 8/2015 |
| WO | 2018115973 A2 | 4/2016 |
| WO | 2017115128 A2 | 7/2017 |
| WO | 2018074980 A1 | 4/2018 |
| WO | 2016065341 A1 | 6/2018 |
| WO | 2019229722 A1 | 12/2019 |

OTHER PUBLICATIONS

Besser et al., ( 2009) "Modifying Interleukin-2 Concentrations During Culture Improves Function of T Cells for Adoptive Immunotherapy", Cytotherapy, 11(2):206-217.

Brocard et al., (Dec. 2006) "Peroxisome Targeting Signal 1: Is it Really a Simple Tripeptide?", Biochimica et Biophysica Acta (BBA)—Molecular Cell Research, 1763(12):1565-1573.

Cho et al., (Mar. 2013) "Targeted Genome Engineering in Human Cells with the Cas9 RNA-Guided Endonuclease", Nature Biotechnology, 31(3):230-232.

Dingwall et al., (Dec. 1991) "Nuclear Targeting Sequences—A Consensus?", Trends in Biochemical Sciences, 16(12):478-481.

Jinek et al., (Aug. 17, 2012) "A Programmable Dual-RNA-Guided DNA Endonuclease in Adaptive Bacterial Immunity", Science, 337(6096):816-821.

Kalderon et al., (Dec. 1984) "A Short Amino Acid Sequence Able to Specify Nuclear Location", Cell, 39( Pt 2):499-509.

Makkerh et al., (Aug. 1996) "Comparative Mutagenesis of Nuclear Localization Signals Reveals the Importance of Neutral and Acidic Amino Acids", Current Biology, 6(8):1025-1027.

Nakamura et al., (2000) "Codon Usage Tabulated from International DNA Sequence Database: Status for the Year 2000", Nucleic Acid Research, 28(1):292.

Omura, Tsuneo, (1998) "Mitochondria-Targeting Sequence, a Multi-Role Sorting Sequence Recognized at All Steps of Protein Import into Mitochondria", The Journal of Biochemistry, 123(6):1010-1016.

Park et al., (Aug. 2015) "Engineering Mesenchymal Stem Cells for Regenerative Medicine and Drug Delivery", Methods, 84:3-16.

Ran et al., (Nov. 2013) "Genome engineering using the CRISPR-Cas9 system", Nature Protocols, 8 (11):2281-2308.

Rapaport, Doron, (Nov. 2003) "Finding the Right Organelle. Targeting Signals in Mitochondrial Outer-Membrane Proteins", EMBO Reports, 4(10):948-952.

Scott et al., (Aug. 3, 2011) "NoD: A Nucleolar Localization Sequence Detector for Eukaryotic and Viral Proteins", BMC Bioinformatics, 12:317 (7 pages).

Tumeh et al., (Oct. 2010) "The Impact of Ex Vivo Clinical Grade Activation Protocols on Human T cell Phenotype and Function for the Generation of Genetically Modified Cells for Adoptive Cell Transfer Therapy", Journal of Immunotherapy, 33(6):759-768 (17 pages.).

O'Dea et al., (Mar. 30, 2017) "Vector-Free Intracellular Delivery by Reversible Permeabilization", PLOS One, 12(3): e0174779 (23 pages).

* cited by examiner

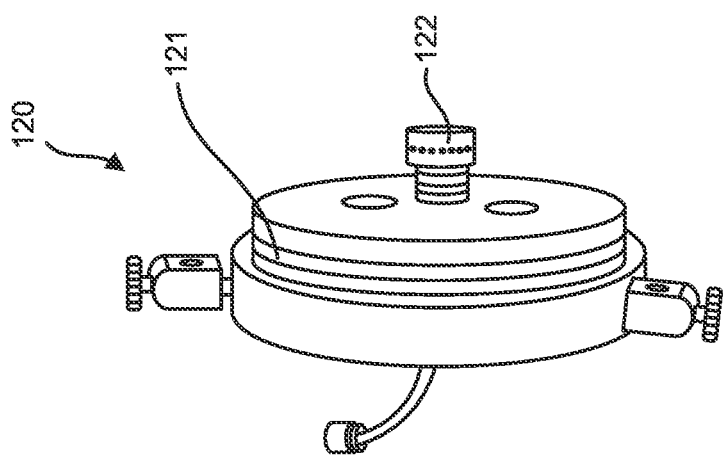
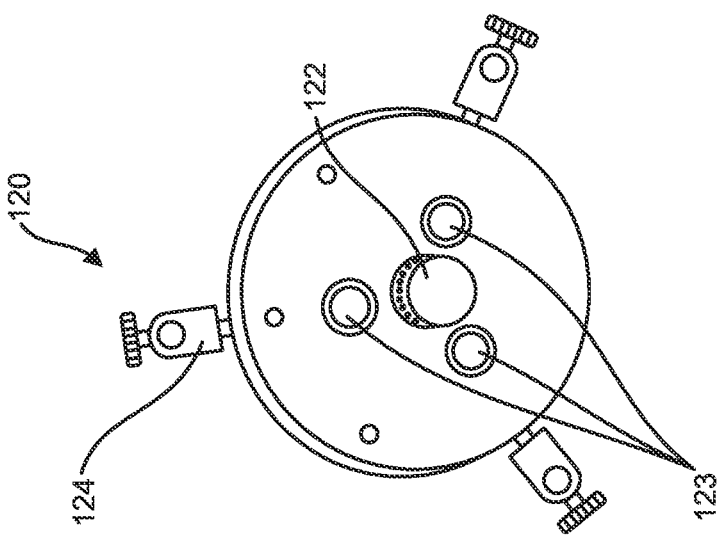
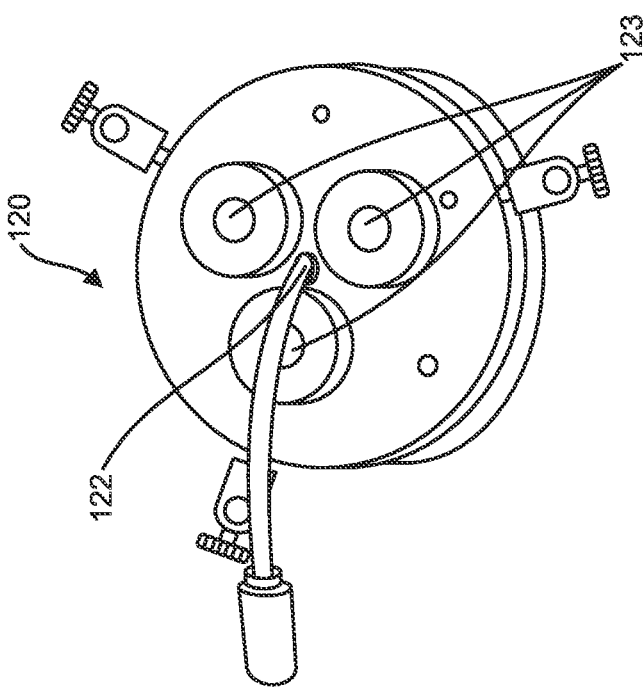
FIG. 4C
FIG. 4B
FIG. 4A

S11: Introduce cell-containing medium into the chamber

S12: Discharge the medium through the filters and thereby depositing the target cells on the filter surface S13: Spray delivery solution containing cell permeabilization agent and payload via the atomizer S14: Introduce stop solution into the chamber S15: Resuspend the cells S16: Collect the engineered cells

*FIG. 9A*

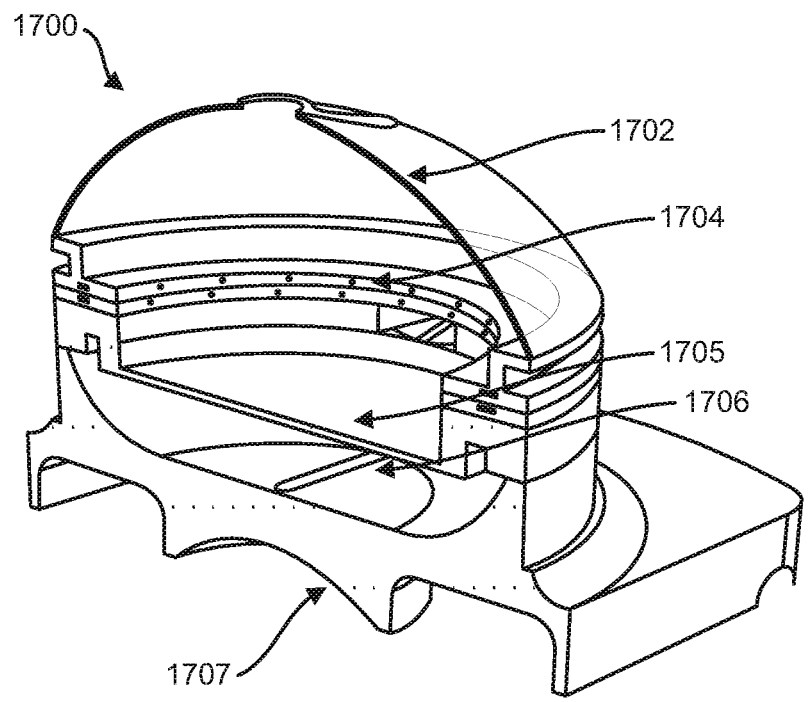
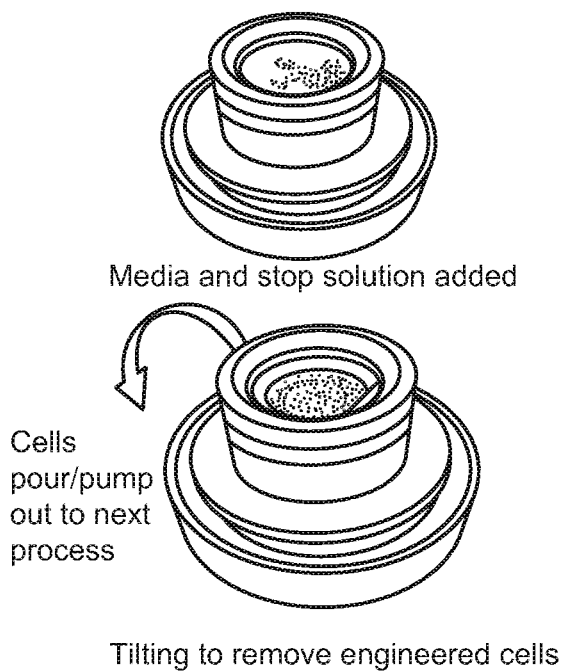
Media and stop solution added
Cells pour/pump out to next process
Tilting to remove engineered cells
FIG. 19

| | |
|---|---|
| System input | ¼ in welded PVC tube or Spiros carrying cells, culture media, molecular cargo, stop solution, air/gas |
| System output | ¼ in welded PVC tube or Spiros carrying $10^{1}9$ engineered T cells in 300mL serum free media for next unit |
| Target System throughput | $10^9$ T cells in < 60 mins |
| Cells | T Cells, NK Cells, PBMCs, CIK Cells & related cell lines |
| Cargos | mRNA form of gene editing tools eg megaTAL, RNPs, Plasmids, Proteins |
| Regulatory approvals | Sterile, single use processing assemblies Closed, cGMP-compliant |
| Cell Engineering Performance | >90% efficiency, viability and yield, functionality and proliferation capability preserved |
| Reagents | Permeabilizing solution and stop solution provided sterile and stable from CMO. |
| Configuration | Bench top or trolly mount enclosure max 750mm cube<br><20kg. Single phase 230VAC supply, 6 bar clean air or bottle. ¼ in tube welder on device (Terumo) |
| Operability with other processes | Interface to other equipment through standard interfaces |
| In-process quality controls | Sample ports at key locations |

*FIG. 23*

|  | Unit Operations Sampling | | Integrated System Sampling |
|---|---|---|---|
|  |  | CAR-TXpress™ |  |
| Selection/Isolation/ Enrichment | • Density gradient configuration (ficoll)<br>• FABian® (selection)<br>• Elutra® (enrichment)<br>• Sepax™ (enrichment)<br>• Anti-CD3/anti-CD28 beads<br>• Magnetic Selection<br>• Flow Cytometric Sorting | • SynGenX-LAB<br>• SynGenX-BACS | • CliniMACS Prodigy®<br>• Cocoon™ |
| Activation/Simulation | • Anti-CD3 mAb (OKT3) and IL-2<br>• CD3/CD28 Dynaboads®<br>• TransAct™ (nano) beads<br>• Viral Peptides<br>• Artificial Antigen Presenting Cells<br>• Expamer™<br>• ImmunoCult™ Human CD2/CD3/CD28 T-cell Activator |  |  |
| Gene Transfer/Gene Delivery | • Viral (transduction)<br>• Non-viral (transfection) |  |  |
| Expansion/Culture | • Gas permeable static bags<br>• Expandable bags (static fed-batch in bags)<br>• G-Rex (Gas Permeable Rapid Expansion)<br>• Xuri™ Cell Expansion System W25<br>• Xuri™ Cell Expansion System W5 (formerly WAVE)<br>• Quantum® |  |  |
| Formulation | • COBE® 2991 Cell Processor<br>• Cell Saver® 5<br>• LOVO Automated Cell Processing System<br>• Sefia | • SynGenX®<br>• BioArchive® |  |
| Cryopreservation | • Mr. Frosty™<br>• VIA Freeze™ Duo<br>• VIA Freeze™ Quad<br>• Cryomed™<br>• CoolCell® |  |  |
| Thaw | • VIA Thaw CB1000<br>• VIA Thaw SC2<br>• CellSeal® Automated Thawing System<br>• ThawSTAR® CFT2 Transport and Cell Thawing System System |  |  |
| Devices are for intended for research use only (RUO) unless otherwise indicated by their respective manufacturers. All trademarks, service marks, trade names, trade dress and/or product names are the property of their respective owners. | | | |
| Adapted from the following sources: Fesnak et al., Curr. Hematol. Malig. Rep., 2017; X. Wang and I. Riviere, Mol. Ther. Oncolytics, 2016 | | | |

*FIG. 24*

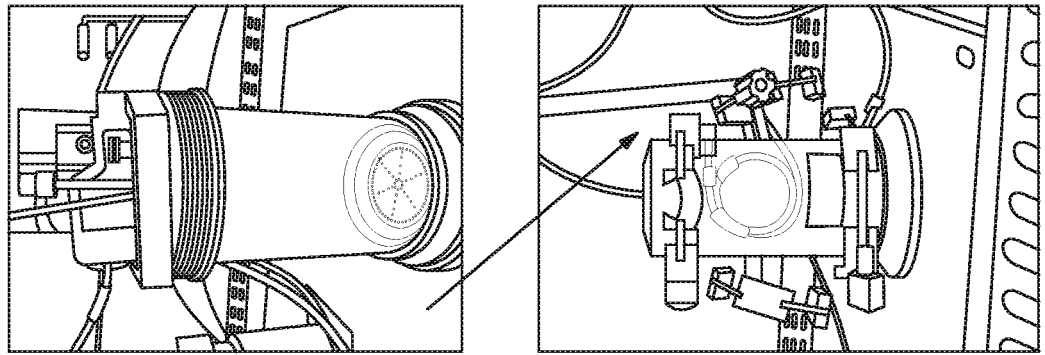
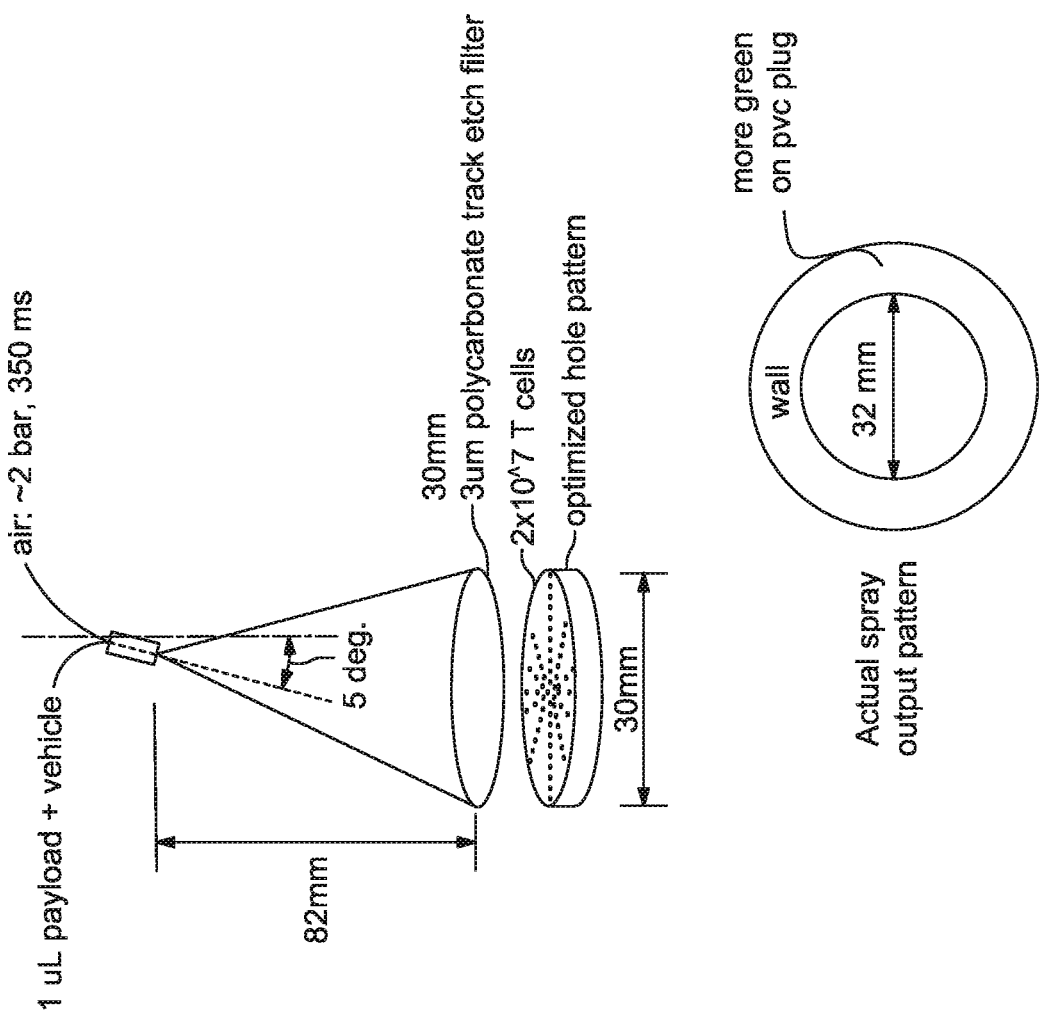
FIG. 27

| Starting material | PBMC | | | | | |
|---|---|---|---|---|---|---|
| Activation reagent | PBMC-initiated T cells (soluble CD3 & CD28 Ab) | | CD3+ T cells | | CD3+ T cells | |
| | | | TransAct 1x | | Dynabead 3x | |
| Processing time for isolation (1/2 LP) | 3 hr | | 7 hr | | 7 hr | |
| Processing time for assay (20x10^6 cells_1 donor) | Thaw | Preparation | Thaw | Preparation | Thaw | Preparation |
| | 30 min | 20 min | 30 min | 15 min | 30 min | 30 min |
| Activation time | 72 hr | | 48 hr | | 19 hr | |
| Complexity of protocol | Only wash step required to remove | | Only wash step required to remove | | More time-consuming due to de-bead step | |
| Efficiency | Up to 78% GFP mRNA | | Up to 45% | | Up to 80% GFP mRNA | |
| Viability | 80-100% | | 80-100% | | 80-100% | |
| Gentle on cells? | Yes, no membrane stripping | | Yes, no membrane stripping | | Strips membrane post-debead but recovers | |
| In clinical use | Yes | | Yes | | Yes | |

| Starting material | PBMC (AllCells) | | Pan T cells (AllCells) | | Pan T cells (AllCells) | |
|---|---|---|---|---|---|---|
| Activation reagent | PBMC-initiated T cells (soluble CD3 & CD28 Ab) | | TransAct 1x | | Dynabead 3x | |
| Processing time for isolation | 0 hr | | 0 hr | | 0 hr | |
| Processing time for assay (20x10^6 cells_1 donor) | Thaw | Preparation | Thaw | Preparation | Thaw | Preparation |
| | 30 min | 20 min | 30 min | 15 min | 30 min | 30 min |
| Activation time | ~72 hr | | - | | - | |
| Complexity of protocol | Only wash step required to remove | | Only wash step required to remove | | More time-consuming due to de-bead step | |
| Gentle on cells? | Yes, no membrane stripping | | Yes, no membrane stripping | | Strips membrane post-debead but recovers | |
| In clinical use | Yes | | Yes | | Yes | |

FIG. 31

Fill volumes of CryoMACS Freezing Bags

| Product | Nominal volume | Recommended fill volume |
|---|---|---|
| CyroMACS Freezing Bag 50 | 50 mL | 10 – 20 mL |
| CyroMACS Freezing Bag 250 | 250 mL | 30 – 70 mL |
| CyroMACS Freezing Bag 500 | 500 mL | 55 – 100 mL |
| CyroMACS Freezing Bag 750 | 750 mL | 80 – 190 mL |
| CyroMACS Freezing Bag 1000 | 1000 mL | 125 – 270 mL |

$1 \times 10^9$ Target Cells Addressed:
Typical yield PBMC ½ LP: $3 – 4 \times 10^9$ (60 - 80 vials) - Cells cryopreserved at $50 \times 10^6$ per vial
Typical yield CD3 ½ LP: $1.5 – 3.5 \times 10^9$ (75 – 175 vials) - Cells cryopreserved at $20 \times 10^6$ per vial
Fill volume of 1L Cryobag: 270 ml ($5.4 \times 10^9$ CD3)
Fill volume of 750 ml Cryobag: 190 ml ($3.8 \times 10^9$ CD3 or $9 \times 10^9$ PBMC)

| | Option A | | Option B | | Option C | |
|---|---|---|---|---|---|---|
| Starting material | CD3/Dyna | PBMC | CD3/Dyna | PBMC | CD3/Dyna | PBMC |
| # Cycles | 20 cycles | 20 cycles | 10 cycles | 10 cycles | 1 run | 1 run |
| # Cells | $5 \times 10^7$ cells p/cycle | $5 \times 10^7$ cells p/cycle | $10 \times 10^7$ cells p/cycle | $10 \times 10^7$ cells p/cycle | $1 \times 10^9$ cells p/run | $1 \times 10^9$ cells p/run |
| # of Cryovials | 5-6 | 2-3 | 10-12 | 4-5 | 100-110 | 40-50 |
| # of Cryobags | na | na | 1 x 50 ml | na | 1 x 750 ml/1 L | 1 x 750 ml/1 L |

*FIG. 32*

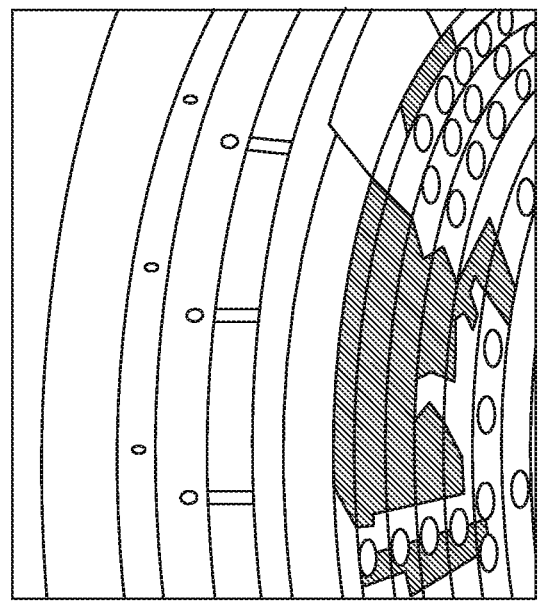
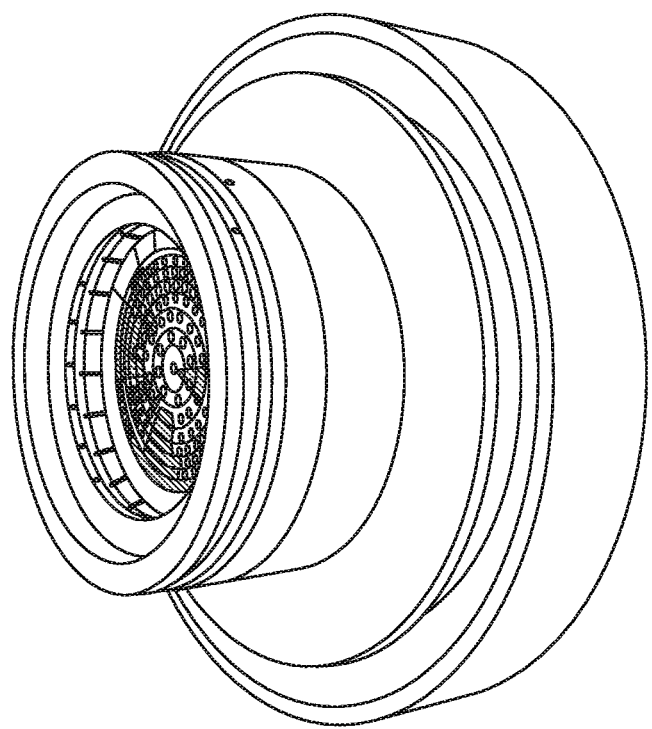
FIG. 35

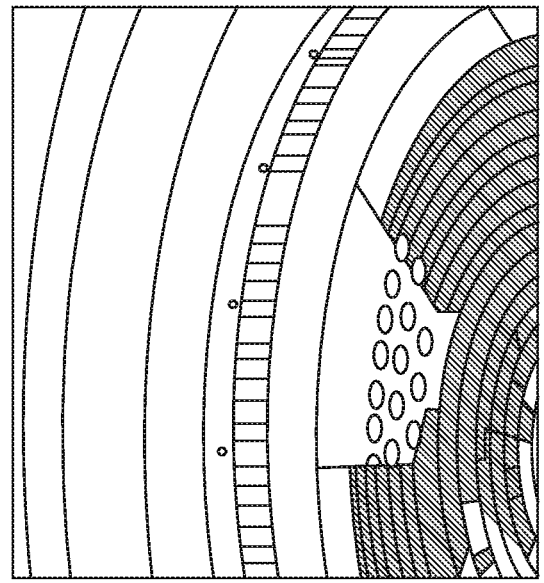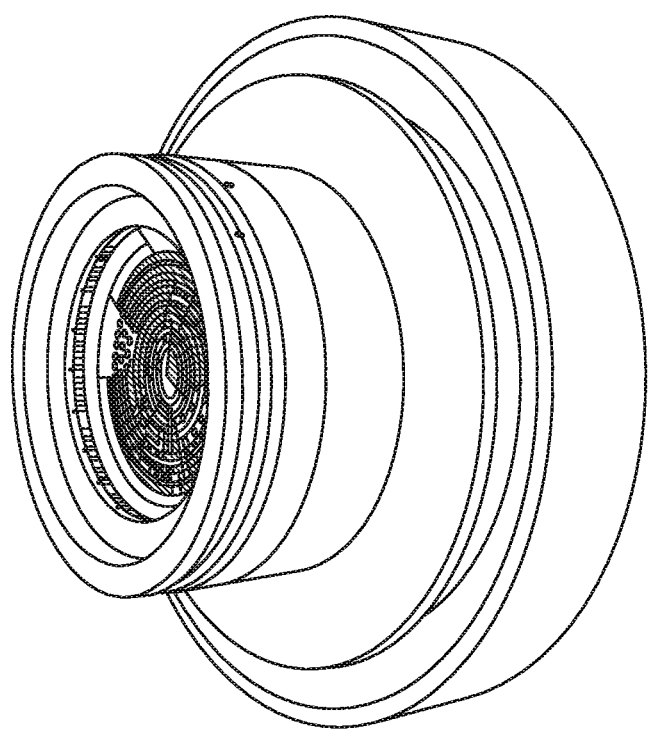
FIG. 36

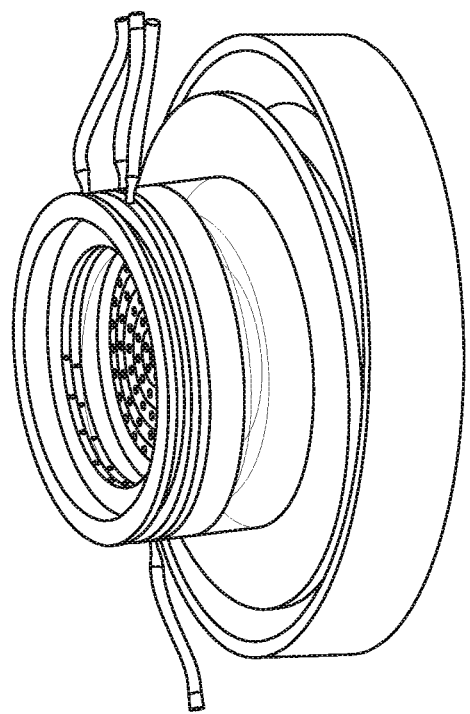
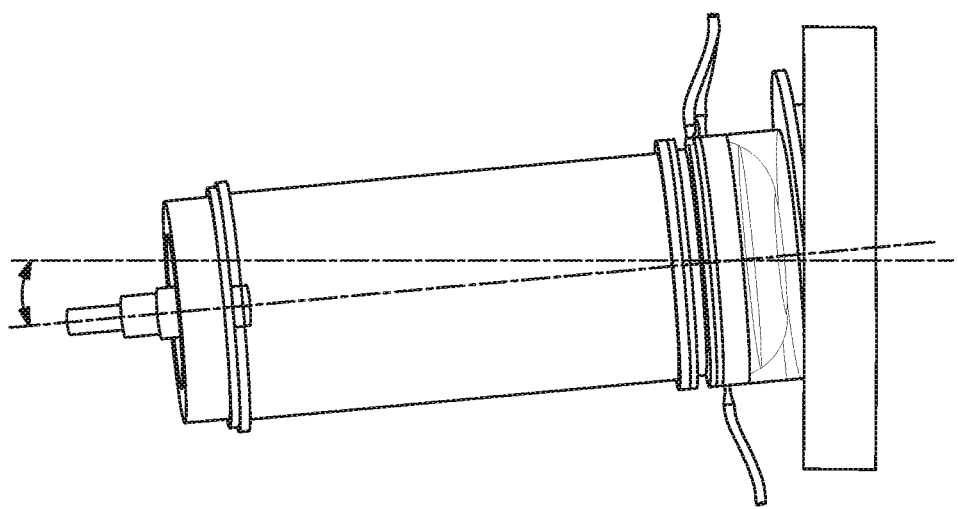
FIG. 37

CELL ENGINEERING PLATFORM

CROSS-REFERENCE TO RELATED APPLICATIONS

This application is a national stage application filed under 35 U.S.C. 371, of International Patent Application No. PCT/IB2019/054555 filed May 31, 2019, which claims priority from U.S. Provisional Application No. 62/679,715 filed on Jun. 1, 2018, the disclosure of each of which is hereby expressly incorporated herein by reference in their entirety.

TECHNICAL FIELD

The subject matter described herein relates to a cell engineering platform utilizing vector-free delivery.

BACKGROUND

Variability in cell transfection efficiency exists among different cell types. Transfection of suspension cells, e.g., non-adherent cells, has proven to be very difficult using conventional methods, particularly at scale.

SUMMARY

The current subject matter provides a cell engineering platform that can scale a technique of vector-free delivery of payload/cargo compounds and compositions into non-adherent cells. The platform can achieve delivery to a large number of cells quickly. For example, some implementations of the platform can deliver to between $10^7$ and $10^9$ cells or more in a single use for both diagnostic and therapeutic uses. The platform can be a closed system, enable sterile transfection, can deliver mRNA and RNP (ribonucleoprotein particle) to primary T cells, is easy to use, enables repeatable delivery, and the like.

The platform can achieve delivery of a payload across a plasma membrane of a non-adherent cell by performing the steps of providing a population of non-adherent cells and contacting the population of cells with a volume of an aqueous solution, the aqueous solution including the payload and an alcohol at greater than 2 percent (v/v) concentration. For example, the alcohol comprises ethanol, e.g., greater than 5% ethanol. In some examples, the aqueous solution comprises between 5-30% ethanol, e.g., 12% or 25% ethanol. Other compositions are possible.

In an aspect, a method includes filling a chamber of a cell engineering platform with a mixture of cells and a first medium and discharging the first medium from the chamber to cause the mixture to pass through a filter, thereby leaving the cells deposited on the filter. The cell engineering platform can include a chamber, a lid disposed at a first end of the chamber, a base disposed at a second end of the chamber, and a filter holder disposed within the chamber.

One or more of the following features can be included in any feasible combination. The method can include spraying a delivery solution that contains a permeabilization agent and a payload to the cells deposited on the filter. The method can include applying a stop solution in the chamber. The method can further include filling the chamber with a second medium to resuspend the cells from the filter. The discharged first medium can be reused as the second medium. The method can include agitating the chamber. The method can include extracting the resuspended cells from the chamber. The filling the chamber can be performed automatically with a pump and a controller. The method can include culturing the cells within the chamber. The discharging the first medium from the chamber can be performed by supplying a positive pressure into the chamber. Alternatively or additionally, the discharging the first medium from the chamber can be performed by gravity. Further, the applying the stop solution can be performed to wash the cells. The filling the chamber with the second medium can be performed as a cell wash process, a cell concentration change process, and/or a cell medium change process.

In another aspect, a system includes a housing configured to receive a filter plate comprising a well; a differential pressure applicator configured to apply a differential pressure to the well; a delivery solution applicator configured to deliver atomized delivery solution to the well; a stop solution applicator configured to deliver a stop solution to the well; and a culture medium applicator configured to deliver a culture medium to the well.

One or more of the following features can be included in any feasible combination. The housing can include a chamber, a lid disposed at a first end of the chamber, and a base disposed at a second end of the chamber. The filter plate can be disposed within the chamber. The differential pressure applicator can be connected to the lid of the housing and include a shower head, which includes a plurality of apertures at an end portion thereof. The stop solution applicator can deliver the stop solution to the well through a septum provided in the lid of the housing. The culture medium applicator can deliver the culture medium to the well through a septum provided in the lid of the housing or through a port of the chamber. The housing can be configured to tilt the filter plate. The delivery solution applicator can include a robotic arm and spray head, the robotic arm magnetically coupled to the spray head. The system can include a soft elastomeric barrier enclosing the filter plate and spray head. The soft elastomeric barrier separates the robotic arm and the spray head. The robotic arm is configured to carry the spray head to a plurality of locations on the filter plate. The stop solution applicator and the culture medium applicator are formed integral within the housing as ports, and the housing forms a vessel. The vessel includes a waste media outlet for collecting waste media.

The system can further include a soft elastomeric barrier enclosing the filter plate and delivery solution applicator within the housing, the soft elastomeric barrier and the housing forming a bioreactor. The housing can include a filter plate base configured to tilt, rotate, and/or vibrate the filter plate.

The delivery solution applicator can include a robotic arm and spray head, and the spray head is a single-use cartridge. The filter plate can be sized to hold greater than $10^7$ T cells. The system can be configured to automatically: provide to the filter plate cells in media; remove culture media to form a cellular monolayer on top of the filter plate; apply an atomized delivery solution to the cellular monolayer; incubate the cells; apply a stop solution to the incubated cellular monolayer; provide new media to the cellular monolayer; and tilt, vibrate, and/or rotate the filter plate to re-suspend the cells in the new media. The system is configured to repeat the application of the atomized delivery solution, the incubation, and the application of the stop solution.

The delivery solution applicator can include a nebulizer. The delivery solution applicator can be configured to deliver 10-300 microliters of the delivery solution per actuation. The system can further include a temperature control system configured to control a temperature of the delivery solution and/or of the plate comprising the well. The delivery solution can include an aqueous solution, the aqueous solution including the payload and an alcohol at greater than 2 percent (v/v) concentration. The alcohol comprises ethanol. The aqueous solution can include greater than 5% ethanol. The aqueous solution can include between 5-30% ethanol. The aqueous solution can include 12% or 25% ethanol. The aqueous solution can include between 12.5-500 mM KCl (potassium chloride). The aqueous solution can include $10^6$ mM KCl.

The system can further include the filter plate, and the well can be configured to contain a population of non-adherent cells. The non-adherent cell can include a peripheral blood mononuclear cell. The non-adherent cell can include an immune cell. The non-adherent cell can include a T lymphocyte. The payload can include a messenger ribonucleic acid (mRNA). The mRNA can encode a gene-editing composition. The gene editing composition can reduce the expression of PD-1 (programmed cell death protein 1). The mRNA can encode a chimeric antigen receptor.

The system can be for use to deliver a cargo compound or composition to a mammalian cell. The population of non-adherent cells can include a monolayer.

In yet another aspect, a system can include a chamber; a lid disposed at a first end of the chamber; a base disposed at a second end of the chamber; and a filter holder disposed within the chamber.

One or more of the following features can be included in any feasible combination. The filter holder can include a plurality of apertures arranged in a predetermined pattern. The filter holder can include a plurality of targets within which the plurality of apertures are arranged to allow cells to be deposited on a filter at areas corresponding to the plurality of apertures. The system can further include a gasket disposed between the filter holder and the base. The system can further include a filter holder insert received within the filter holder to accommodate the filter between the filter holder and the filter holder insert. The filter holder insert can include a concavely shaped top surface. The filter holder insert can include a plurality of openings corresponding to the plurality of targets. The filter holder can include three targets. The filter holder can include seven targets. The filter holder can include nineteen targets. The plurality of targets can be arranged in a square pattern, a rectangular pattern, a triangular patter, or a linear pattern.

The system can further include a controller configured to operate at least one of a pump, a valve, a heating element, a cooling element, and an agitation device. The pump can be a peristaltic pump or a positive displacement pump. The lid can further include a pressure port and an aperture. The base can include a port for receiving media or for draining the media. The lid can further include a septum. The pressure port can include a shower head, which includes a plurality of apertures at an end portion thereof. A 0.2 micron filter can be connected to the pressure port. The system can further include a pinch valve that is configured to open and close the pressure port to atmosphere through the 0.2 micron filter. The chamber of the system can include a port for extracting processed cells. The system can be sized to process greater than $1 \times 10^9$ T cells.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIGS. 4A-4C illustrate a lid according to the exemplary embodiment of the cell engineering platform.

FIGS. 9A-9C show flow diagrams for an exemplary method of vector-free payload delivery across cell membranes.

FIG. 19 is a CAD drawing illustrating a cross-sectional view of the example platform and rotation of the filter plate.

FIG. 23 is a table illustrating some example performance capabilities for the example platform.

FIG. 24 is a table illustrating compatible technologies that the example platform can be integrated with.

FIG. 27 is a series of images showing another example bio-reactor design for use with the platform.

FIG. 31 illustrates a comparison of processing time and complexity to isolate and activate 1 million cells. A comparison between peripheral blood mononuclear cells (PBMCs), cluster of differentiation 3 cells (CD3+) and Pan T cells is shown.

FIG. 32 illustrates a comparison of metrics for processing starting material (e.g., cells and activation reagent) and number of cycles, number of cells, number of cryovials and number of cryobags.

FIG. 35 illustrates the filter plate vessel with stop solution added.

FIG. 36 illustrates the filter plate vessel with new media added.

FIG. 37 illustrates the bioreactor tilting during operation.

Like reference symbols in the various drawings indicate like elements.

DETAILED DESCRIPTION

Despite some advances, delivery of certain particles and/or molecules into cells remains a challenge. Factors such as size or charge of a molecule to be delivered into a cell can limit and/or prevent delivery of the molecule into the cell. In particular, delivery across the cell membrane can be complicated due to the molecule and/or the membrane of the cell. A cell membrane or plasma is a semi-permeable biological membrane, which acts as a selective barrier. The membrane regulates an internal chemical composition of the cell. As the selective barrier for the cell, the membrane can allow only certain molecules to passively translocate across the membrane through, for example, passive diffusion into the cell. Small, hydrophobic molecules (such as $O_2$, $CO_2$, and $N_2$) and small, uncharged polar molecules (such as $H_2O$ and glycerol) can passively diffuse across cell membranes. Larger, uncharged polar molecules (such as amino acids, glucose, and nucleotides) and ions (such as $H^+$, $Na^+$, $K^+$ and $Cl^-$) cannot passively diffuse across cell membranes.

Figure 1:
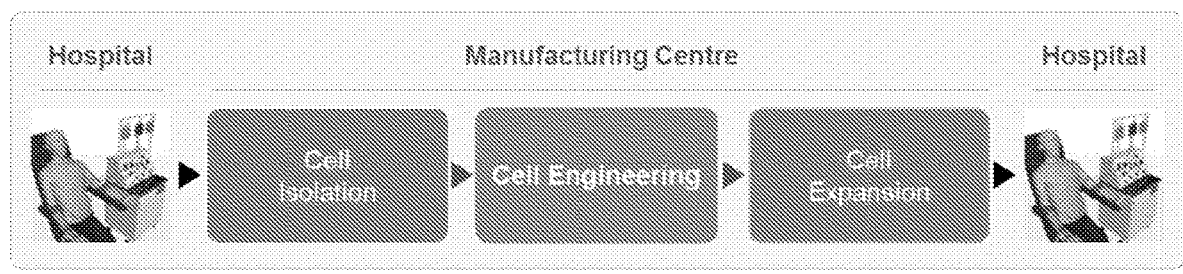
FIG. 1 illustrates an exemplary implementation of a treatment/process involving the cell engineering.

FIG. 1 illustrates an exemplary implementation of a treatment/process involving the cell engineering. Referring to FIG. 1, cells can be extracted from a patient, isolated (e.g., concentrated or enriched), and subsequently be treated with the cell engineering methods. The engineered cells can be expanded and returned to the patient. For delivery across cell membranes, methods using viral vectors can be used. However, the methods based on viral vectors generally require high costs and complex processes, provide limited accessibility, and offer variable and inconsistent results. Methods based on electroporation can also be used. However, the electroporation-based methods generally result in higher cell damage and offer poor cell recovery and cell functionality.

An object of the present disclosure is to provide a vector-free delivery method to address the cost and complexity challenges for the cell engineering technologies. To provide a reliable and consistent method for cell therapies, the current subject matter provides a cell engineering method and platform to deliver compounds or mixtures of compounds (e.g., payload) into cells across cell membranes by contacting the cells with a delivery solution (e.g., vehicle) containing the payload and an agent that reversibly permeates or dissolves a cell membrane. In particular, the cells are supplied to a system in a suspension, a monolayer of the cells are formed by draining the suspension, the delivery solution is supplied (e.g., sprayed) to permeabilize the cells, and the payload is delivered across the permeabilized cell membranes.

Using a platform of some implementations of the present disclosure, other cell engineering processes may also be performed before and/or after the vector-free payload delivery process, which significantly enhances productivity and allows the overall process to be streamlined. Moreover, not only the non-viral transfection method but also viral methods may be performed within the single platform. Accordingly, example implementations of the platform can provide improved scalability over other methods and systems, and can treat $10^{11}$ cells or more at a single process.

In some implementations, the platform for payload delivery across cell membranes may be used for the vector-free payload delivery, the viral payload delivery, or a combination of vector-free and viral payload delivery. For example, after the cells are collected on the filter substrate by discharging the cell-containing medium through the filter, a solution that contains viral payload may be delivered to the collected cells, thereby performing the viral payload delivery in the platform. Additionally or alternatively, the vector-free and the viral payload delivery processes may be performed to the same cells within a single device, which may decrease the process steps, time, and/or cost, increase the cell throughput, survivability, and effectiveness of the treatment, and moreover, reduce cell contamination that may happen when the cells are transported between multiple devices. Additional aspects of viral payload delivery are discussed in U.S. Provisional Patent Application No. 62/855,241 filed May 31, 2019, entitled "Methods of Viral Delivery to A Population of Cells and Viral Production Thereof", the entire contents of which is hereby expressly incorporated by reference herein.

Further, some implementations of the current subject matter can provide a cell engineering platform that can scale a technique of vector-free delivery of payload/cargo compounds and compositions into non-adherent cells. The example platform can achieve delivery to a large number of cells quickly. For example, some implementations of the platform can deliver to between $10^7$ and $10^9$ cells or more in a single use. The platform can be a closed system, enable sterile transfection, can deliver mRNA and RNP to primary T cells, is easy to use, enables repeatable delivery, and the like. For another example, human embryonic kidney (HEK) cells may be treated using the platform according to the present disclosure.

The platform can achieve delivery of a payload across a plasma membrane of a non-adherent cell by performing the steps of providing a population of non-adherent cells and contacting the population of cells with a volume of an aqueous solution, the aqueous solution including the payload and an alcohol at greater than 2 percent (v/v) concentration For example, the alcohol comprises ethanol, e.g., greater than 5% ethanol. In some examples, the aqueous solution comprises between 5-30% ethanol, e.g., 12% or 25% ethanol. Other compositions are possible.

The current subject matter also provides a platform that can automate the vector-free and/or the viral payload delivery process and allow the process to be performed at various scales. When cells are manually loaded to the platform and/or manually unloaded from the platform, the throughput of the system is limited, and difficulties exist in applying to clinical process/treatment. There may be concerns for contamination and inconsistent process depending on operators and/or various environmental parameters. By the process automation, the vector-free payload delivery process can be performed more consistently, a concern for contamination can be significantly reduced, and therefore, the system can be scaled more easily. Hereinbelow, exemplary embodiments of the platform to perform the vector-free payload delivery process with automated processes will be described.

Example 1

Figure 2:
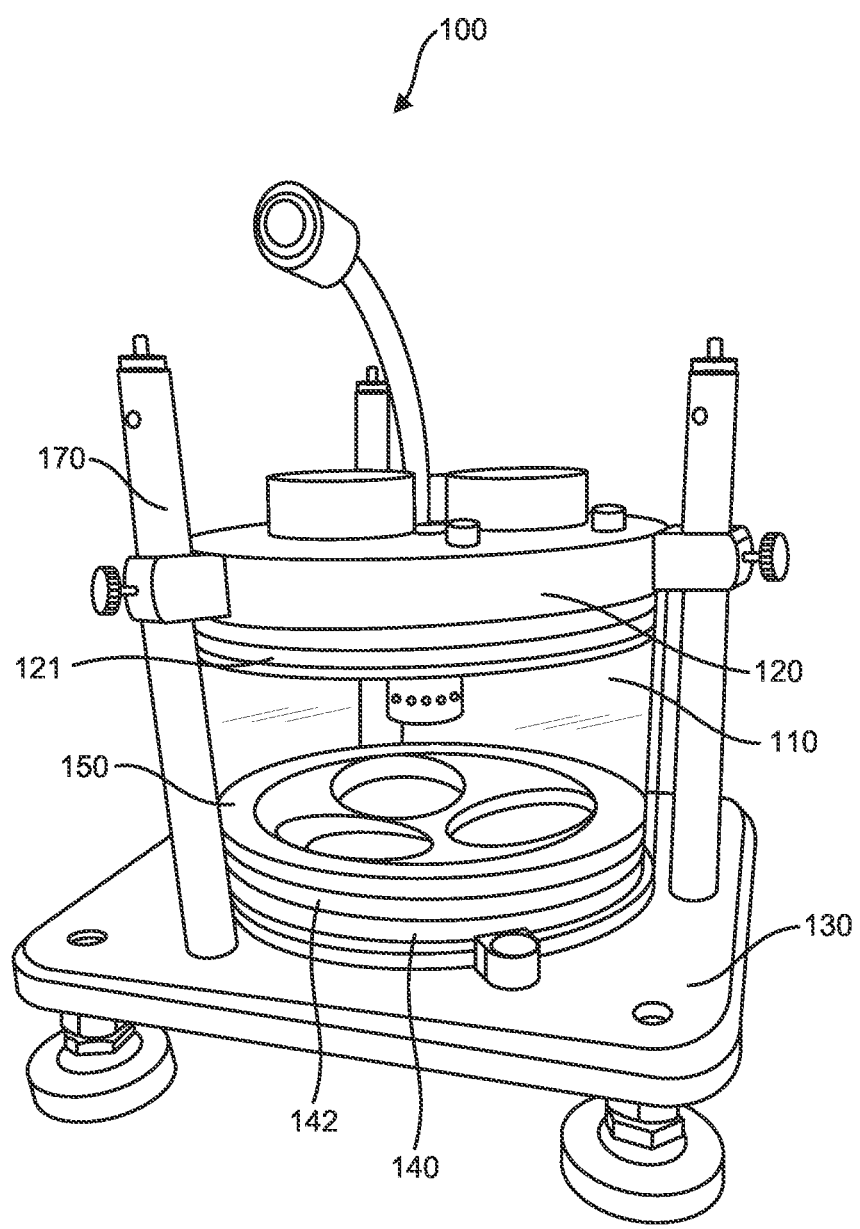
FIG. 2 illustrates an exemplary embodiment of the cell engineering platform for vector-free payload delivery across the cell membrane.
Figure 3:
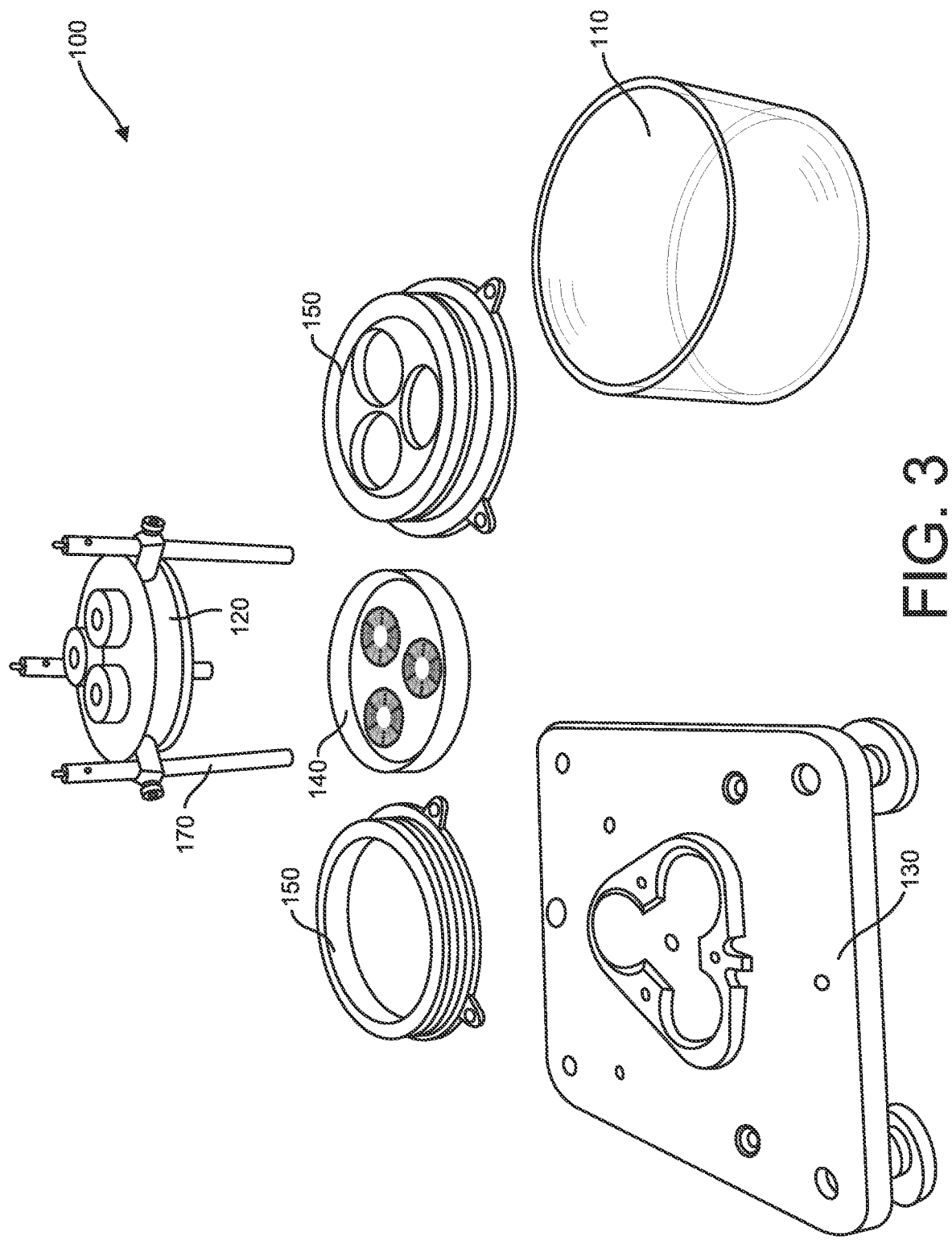
FIG. 3 illustrates the exemplary embodiment of the cell engineering platform of FIG. 2 shown with parts disassembled for illustration purposes.

FIG. 2 illustrates an exemplary embodiment of the cell engineering platform 100 for vector-free payload delivery across cell membranes, and FIG. 3 illustrates the exemplary embodiment of the cell engineering platform 100 of FIG. 2 shown with parts disassembled for illustration purposes. Referring to FIGS. 2 and 3, the platform 100 for cell engineering includes a chamber 110, a lid 120 disposed at a first end of the chamber 110, a base 130 disposed at a second end of the chamber 110, a filter holder 140, and a filter holder insert 150. The platform may include a gasket 160 disposed between the base 130 and the filter holder 140. The platform 100 may also include a controller.

The chamber 110 is enclosed by a chamber wall. To provide an optical observation capability, the chamber wall may include (e.g., be made of) a clear plastic material such as polypropylene, acrylic, polycarbonate, and the like. The chamber wall may have an overall shape of a cylindrical shell with a top and a bottom surfaces thereof open, and a diameter and a height of the chamber 110 may be determined based on applications and system requirements. For example, the chamber 110 may have an internal diameter of 110 mm. Alternatively or additionally, the chamber 110 may include a flat surface to facilitate an optical imaging device to be used for monitoring and/or controlling the transfection process. Although the chamber 110 is shown as a cylindrical shell, the present disclosure is not limited thereto, and the chamber 100 may have various shapes, for example, square, rectangular, and triangular shapes as well as a configuration in which cell targets are arranged in a linear configuration.

FIGS. 4A-4C show pictures of the lid 120. FIG. 4A shows a top surface of the lid 120, FIG. 4B shows a bottom surface of the lid 120, and FIG. 4C shows a side surface of the lid 120. The lid 120 is disposed on a top portion of the cell engineering platform 100, and thereby seal the chamber 110 of the platform 100. For sealing, the lid 120 may include an o-ring 121. The lid 120 may include a pressure port 122. The pressure port 122 may allow the chamber 110 to be connected to a pressure source. The pressure source may supply a positive pressure or a negative pressure to the chamber 110 of the platform 100. Referring to FIGS. 4A and 4C, a pressure source may be connected to a top portion of the pressure port 122, which is disposed above or at an outer side of the lid 120. A bottom portion of the pressure port 122, which is disposed below or at an inner side of the lid 120 may include a shower head, which includes a plurality of apertures to distribute fluid over the plurality of the apertures, to supply the pressure more evenly into the chamber 110. As shown in FIG. 4C, the plurality of apertures of the shower head may be directed toward substantially sideways to prevent the flow (e.g., gas or liquid) being delivered through the apertures from disturbing (e.g., blowing) the cells deposited on the filter.

Alternatively or additionally, the pressure port 122 may allow the chamber 110 to be connected to (e.g., exposed to) an ambient pressure. Further, the pressure port 122 may allow the chamber to be connected to an ambient pressure through a filter. The filter may be, for example, a 0.2 micron filter. The filter may also be a nano particle filter and/or a high efficiency particulate air (HEPA) filter. When the pressure port 122 is connected to the ambient pressure through the filter, the chamber 110 may be drained due to gravity instead of the pressure source. To open or close the pressure port, a valve may be disposed upstream of the filter. For example, the valve may be a pinch valve.

The lid 120 may include (e.g., be made of) a stainless steel material such as SS316, a plastic material, or the like. The lid 120 may also include at least one aperture 123 to accommodate an atomizer, a sensor, or the like. The sensor may include one or more of a temperature sensor, a humidity sensor, and a pressure sensor. When an atomizer is mounted in the at least one aperture 123, the atomizer may be mounted through an orientation adjustment device such as a gimbal to allow adjustment of the atomizer orientation. In some implementations, the lid 120 may include at least one mounting aperture 124 to accommodate a post 170 to fix the lid 120 to the post 120 and support the platform 100.

Figure 5:
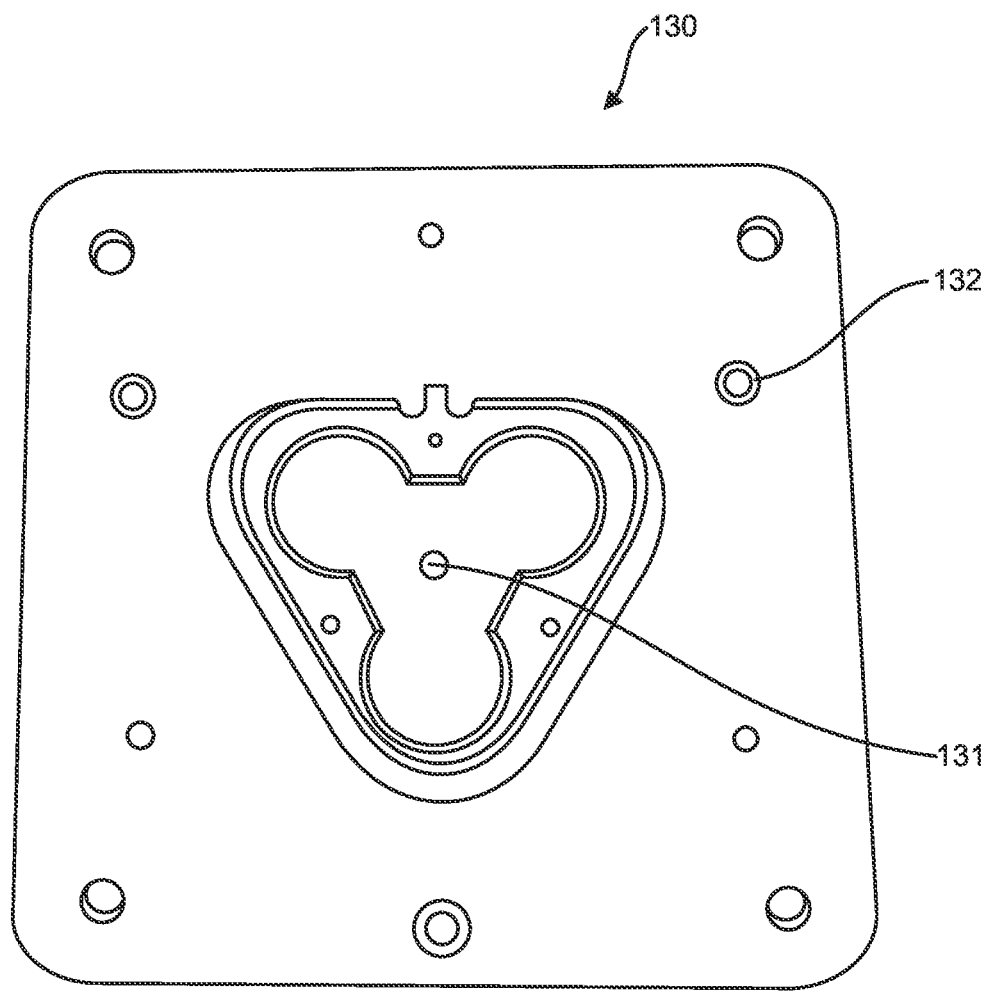
FIG. 5 illustrates a base according to the exemplary embodiment of the cell engineering platform.

FIG. 5 shows the base 130 of the platform 100. The base 130 is disposed at a bottom portion of the chamber 110, and mounts the membrane holder 140. The base 130 may include a drain port 131. Additionally or alternatively, the base 130 may include one or more of a vacuum port, a conduit connected to a syringe for resuspension of cells in the medium to provide an opportunity to resuspend at different concentration or with different medium, a heating element, a temperature sensor (e.g., PT100 RTD, thermocouple, or the like), and a vibration device to provide agitation during the process. The base 130 may include apertures 132 to accommodate the post 170 mounted thereto.

Figure 6:
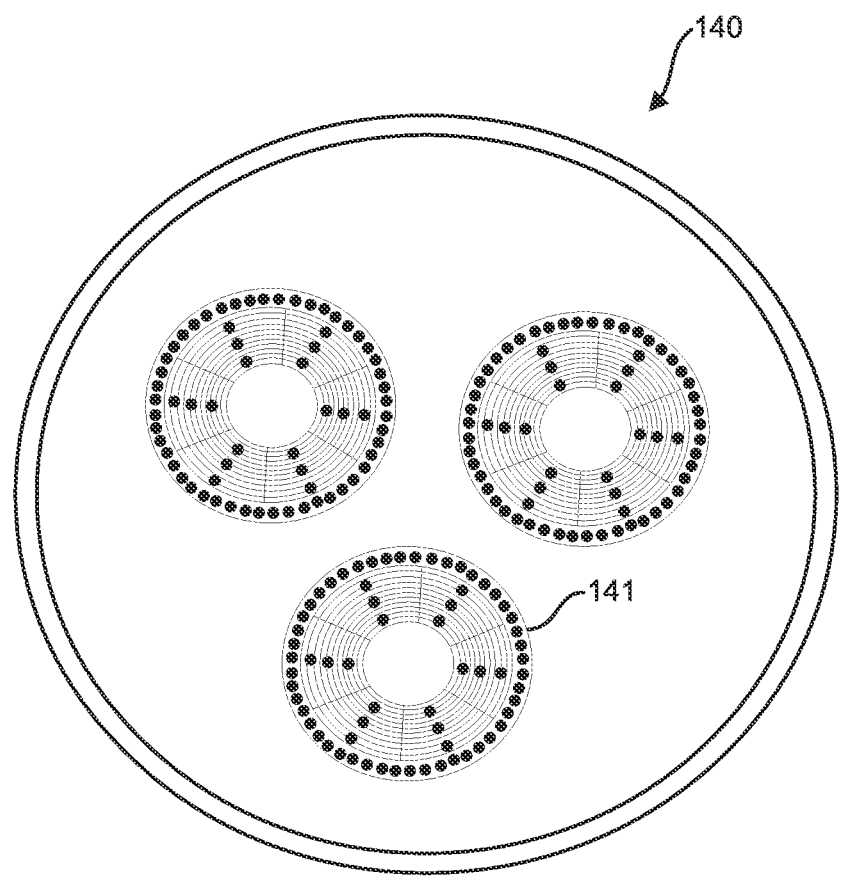
FIG. 6 illustrates a filter holder according to the exemplary embodiment of the cell engineering platform.

FIG. 6 shows the filter holder 140. The filter holder 140 may be made of acetal, aluminum, or the like. The filter holder 140 is disposed at a bottom portion of the chamber 110 and fixed to the base 130. The filter holder 140 may accommodate at least one filter on a top surface thereof. The filter holder 140 may include a target configured to allow the cells to be deposited on the filter. The filter holder 140 may include a plurality of targets. The filter holder 140 may include three targets. At locations corresponding to each target, the filter holder 140 may include a plurality of apertures 141 to allow the cell suspension medium to be transported therethrough. When a positive pressure is applied to the chamber 110 through the pressure port 122 of the lid 120, the cell suspension medium can be drained through the plurality of apertures 141 and through the base 130 while the cells are collected on filter surfaces, and thereby forming a mono-layer of the cells. Alternatively or additionally, the draining may be performed by opening the valve of the pressure port 122, connected to the 0.2 micro filter, to the ambient pressure, and thereby draining the medium by gravity. The plurality of apertures 141 may be arranged to have a predetermined pattern. For example, the apertures 141 may be aligned around an outer diameter of the filter and/or along multiple radial directions of the filter. The filter holder 140 may further include an o-ring 142 to provide a seal between the filter holder 140 and the chamber 110.

Figure 7C:
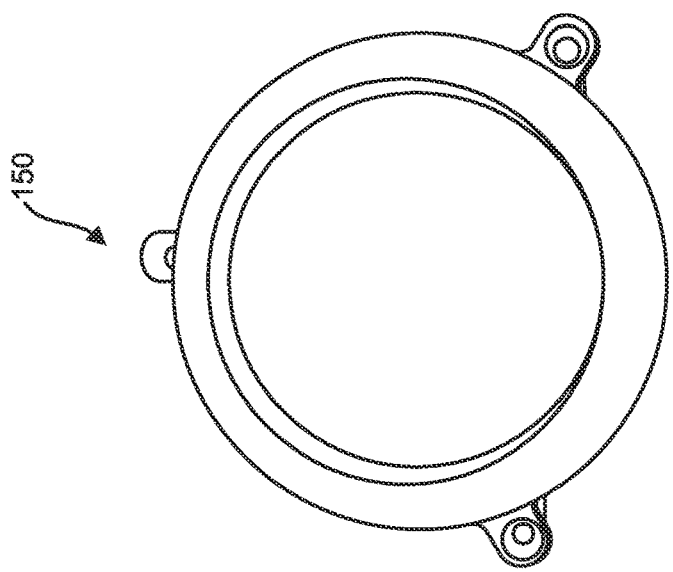
FIGS. 7A-7C illustrate various configurations of a filter holder insert according to the exemplary embodiment of the cell engineering platform.
Figure 7B:
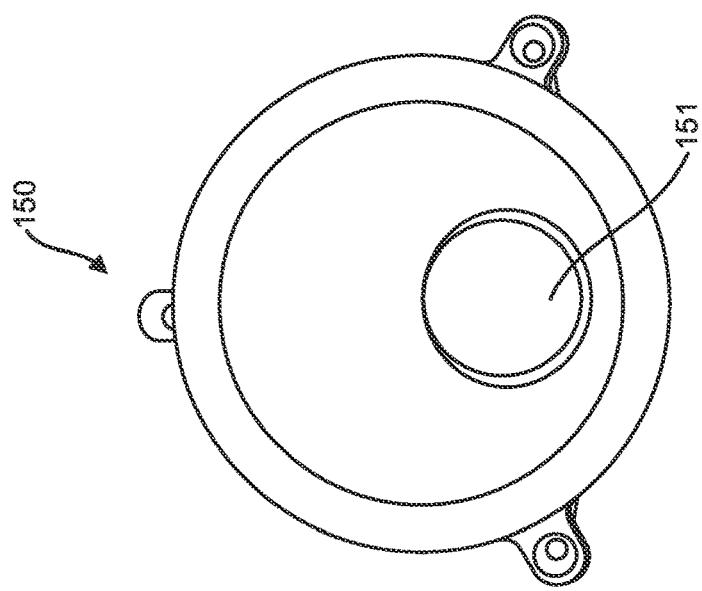
Figure 7A:
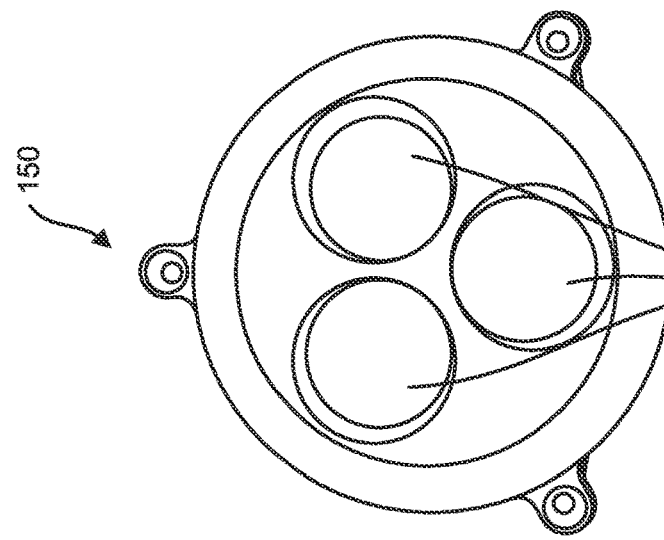

FIGS. 7A-7C show various configurations of the filter holder insert 150. The filter holder insert 150 is disposed at the bottom portion of the chamber 110 and on an upper surface of the filter holder 140, and thereby fix (e.g., hold or clamp) the filter between the filter holder 140 and the filter holder insert 150. As shown in FIGS. 7A to 7C, the filter holder insert 150 may have various configurations. For example, the filter holder insert 150 may have configuration including three targets (FIG. 7A), one target, (FIG. 7B), or an open inner portion (FIG. 7C). The filter holder insert 150 with three targets (FIG. 7A) can facilitate cell distribution and cell recovery only within the filtration areas 151. The filter holder insert 150 with one target (FIG. 7B) may be used when smaller amount of cell is desired. As shown in FIG. 2, the filter holder insert 150 may include a concavely shaped upper surface to allow the cells to be deposited on the filters to receive the spray plume more efficiently. The concave shape may also prevent the filters from bulging near the center during the filling and discharging, and resuspending the cells. The configuration of the targets is not limited to the illustrated configurations, and may also have more than three targets, for example, 7 to 19 or more targets. The plurality of targets may be arranged in square, rectangular, triangular, and/or linear configurations.

Figure 8C:
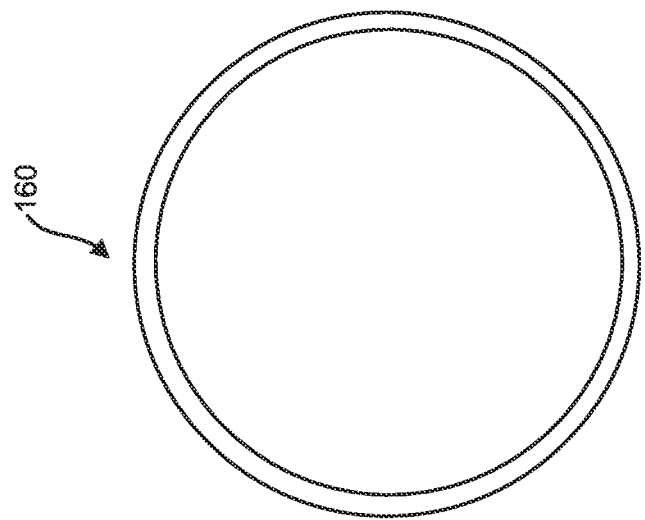
FIGS. 8A-8C illustrate various configurations of a gasket according to the exemplary embodiment of the cell engineering platform.
Figure 8B:
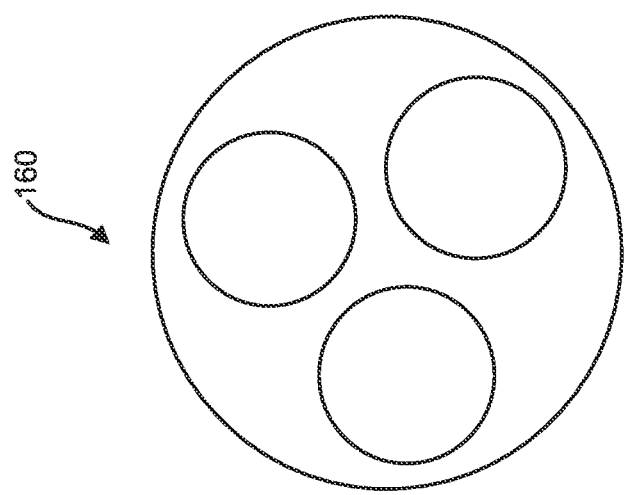
Figure 8A:
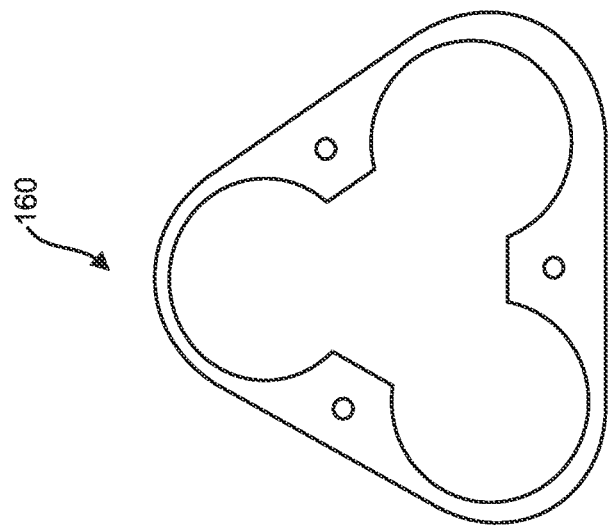

In some embodiments, the platform 100 may include a gasket 160, for example, a rubber gasket, to provide a seal between the base 130 and a bottom surface of the filter holder 140. The seal between the base 130 and the filter holder 140 prevents the cell medium from flowing between the base 130 and the filter holder 140, allows the entire cell medium to flow through the filters, and thereby increases the cell collection efficiency. As shown in FIGS. 8A-8C, the gasket 160 may have various shapes that correspond to the filter configuration. FIG. 8C shows a configuration of the gasket 160 suitable to be used with the open inner portion configuration as shown in FIG. 7C. FIGS. 8A and 8B show the gaskets 160 to be used with the three target configuration shown in FIG. 7A.

In some embodiments, the platform 100 includes a pump such as a peristaltic pump or a positive displacement pump along with a valve to automatically control the fluid flows. The pump may be controlled by the controller. The controller may also control the atomizer, the temperature/pressure sensor, the heating element of the base, and the vibration device. For the atomizer control, a human machine interface (HMI) (e.g., Omron NB3Q-TW01B 5-inch HMI) and programmable logic controller (PLC) (e.g., Omron NX1 NXIP29024DT1 PLC) hardware platforms with a 3 channel Gyger controller printed circuit board (PCB) may be included in the controller. The controller may include a plurality of modules that are responsible for controlling respective elements of the platform. The controller may also include a processor configured to execute program instructions to perform the vector-free payload delivery processes, to operate input/output devices for user interface, and to operate communication modules to connect the platform to a network.

Referring to FIG. 9A, an example method of the vector-free payload delivery across the cell membranes will be described. In operation, the target cells may be mixed in a medium at a particular concentration. For example, about 60 million cells may be mixed in about 60 mL medium. The prepared cell-containing medium may be introduced into the chamber via a disposable tube set and/or sterile needle/cannula (Step S11). The cell-containing medium may be supplied to the chamber through a septum or a port (e.g., a bulkhead to receive a plastic welded tube) in the lid. The loading procedure may be performed manually, or may be performed automatically using a pump (e.g., peristaltic pump or positive displacement pump) and a controller. After the cell-containing medium is loaded in the chamber, the chamber is sealed by closing valves. Similarly, the valve operation may be performed manually, or may be performed automatically using, for example, a solenoid valve and a controller.

After the valves are closed, and the chamber is sealed, the medium is discharged through the filters, thereby depositing the target cells (e.g., T cells) on the filter surfaces (Step S12). For example, a positive pressure may be supplied to the chamber through the central pressure port of the lid. After the medium is discharged from the chamber, a vacuum pressure may be supplied to the chamber to release remaining positive pressure within the chamber. Removing the remaining positive pressure with the vacuum pressure may or may not be required. In some implementations, the positive pressure and the vacuum pressure may be alternatingly supplied to the chamber during the discharge of the medium to adjust/rearrange the cell deposition on the filters. The medium may also be discharged by opening a valve, for example a pinch valve, to expose the pressure port of the lid to the ambient pressure and drain the medium by gravity. A filter such as a 0.2 micron filter may be disposed at the pressure port to prevent foreign particulate matter from entering the chamber.

Figure 11A:
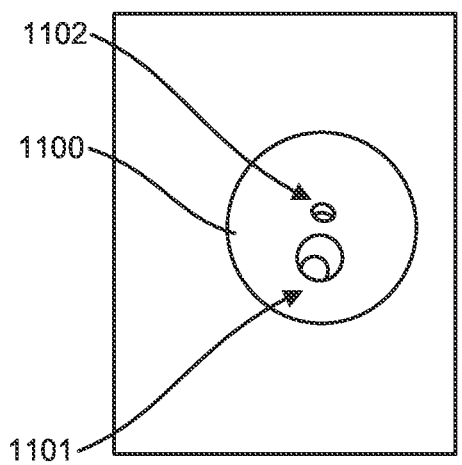
FIGS. 11A-11C show an exemplary embodiment of an atomizer for spraying process.
Figure 11B:
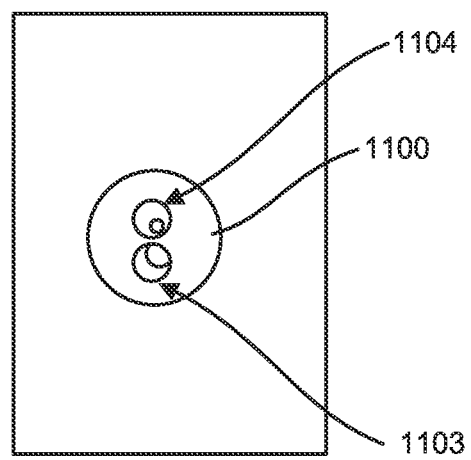
Figure 11C:
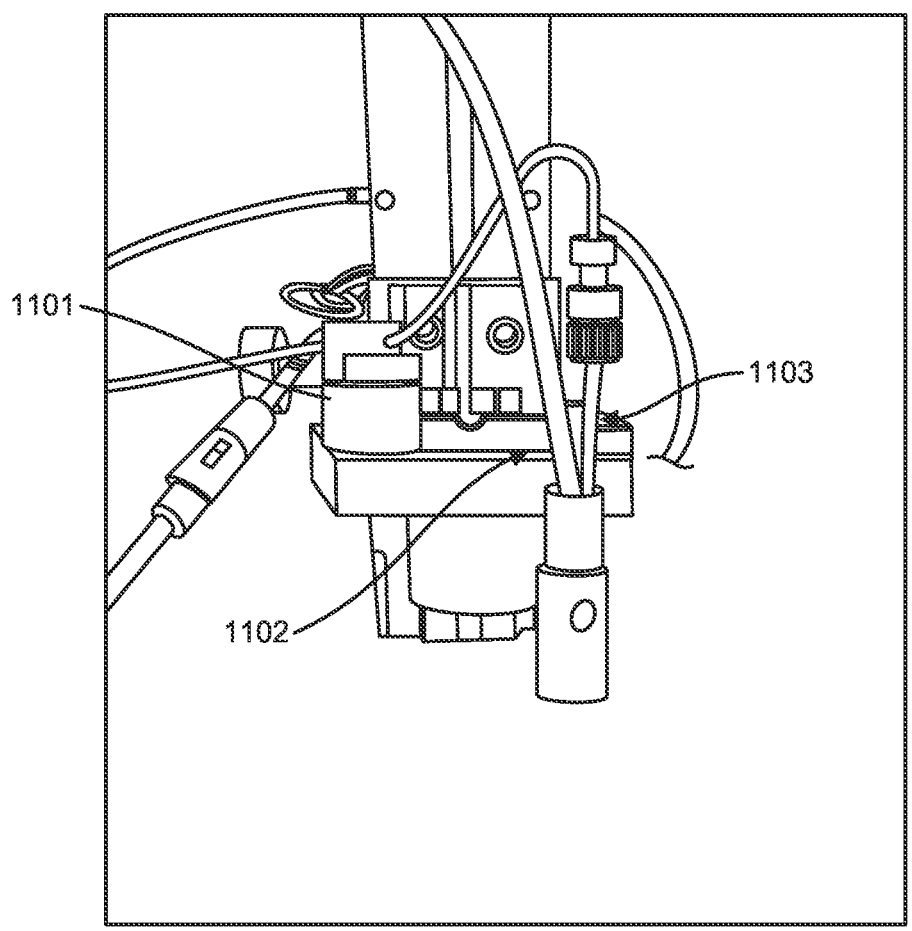
Figure 11D:
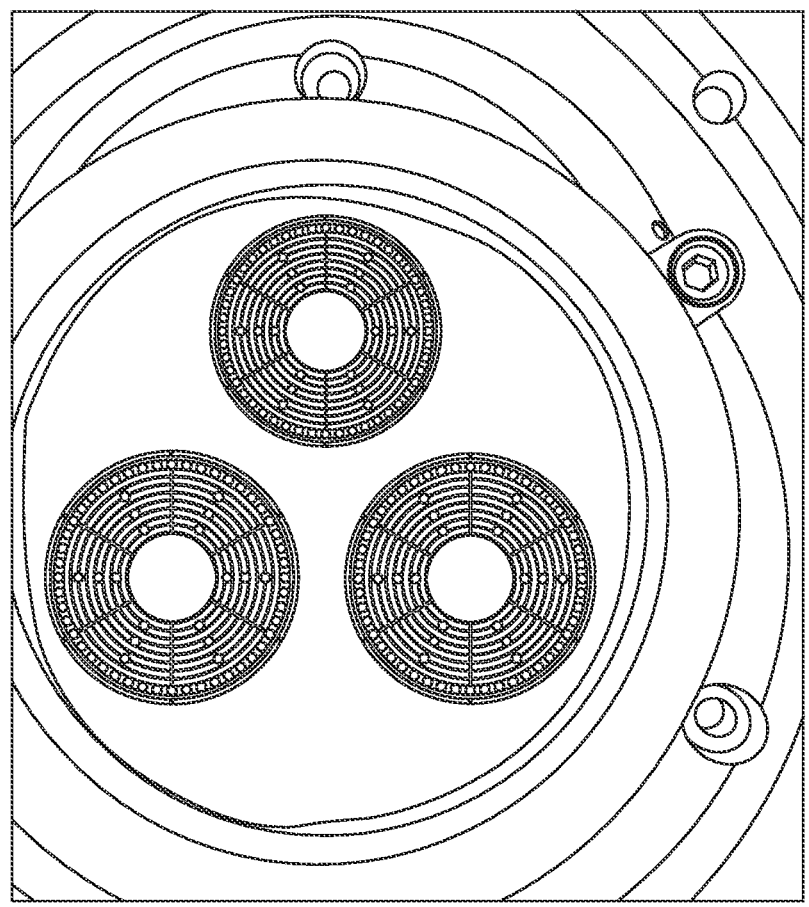
FIG. 11D shows an exemplary image after the cell deposit process.

FIG. 11D shows an exemplary image of the cell deposition pattern after Step S12. FIG. 11D is an image taken using colored beads that mimic cell behavior. Due to the plurality of apertures 141 in the filter holder 140, the cell deposition pattern substantially correspond to the pattern of the plurality of apertures 141. For Step 12, a filter membrane of appropriate pore size may be selected for efficient cell deposition. The filter membrane may allow easy filtration of the liquid, while retaining cells and without affecting cell viability. Pores obtained by means of track etched technology provide the highest yield (e.g., smallest effect on viability, loss of cells in the filtrate minimized). To avoid deformation during filtration and facilitate uniform cell distribution across the target surface, a drain disc having a thicker membrane with a porosity greater than the filter may be disposed underneath the filter. For example, the filter may be 9 μm to 30 μm thick, and the drain disc may be 80 μm thick. During filtration, while liquid suspending the cells (e.g. cell culture media) is drained, cells evenly distribute only on the filtrating areas that correspond to the targets with minimal loss in the non-filtrating areas.

Accordingly, the cell deposition pattern can be controlled and restricted to the areas where the cells are deposited on the filter as a monolayer. Herein, a "monolayer" of cells may refer to the cells distributed substantially horizontally and forming one or more vertical layers of cells. The monolayer may include one cell layer, one to two cell layers, one to three cell layers, one to five cell layers, or more. The number of cell layers are not limited thereto, and the monolayer may refer to any number of cell layers in some implementations.

Subsequently, the delivery solution containing the cell permeabilization agent and the payload (e.g., cargo) is sprayed via the atomizer (Step S13). The controller may control the amount and duration of the spray. For example, the delivery solution may be sprayed for about 300 ms. For spraying the delivery solution, the cargo may be introduced to the spray head via microvial or injected via resealable injection port.

After the delivery solution is sprayed, a stop solution is introduced via a disposable tube set and/or sterile plastic needle/cannula (Step S14). The stop solution may be supplied to the chamber through a septum or a port in the lid. The stop solution may be supplied manually, or may be supplied automatically using the pump and the controller. A desired amount of stop solution is introduced into the chamber. For example, about 10 mL of stop solution may be introduced over about 20 seconds. Step S14, however, is not limited to the stop solution application, and may also provide a cell wash process depending on the composition of the applied solution.

Following the introduction of the stop solution, the cells are resuspended (Step S15). For the resuspension, about 60 mL medium, which may be a used, new medium or the medium that was previously drained from the chamber, can be introduced by a syringe or a pump. The new medium may be supplied into the chamber through a septum or a port in the lid. Alternatively or additionally, the new medium may be supplied into the chamber from below the filter through a drainage hole. The new medium may be supplied into the chamber by injecting the new medium into the chamber with a positive pressure or by applying a vacuum pressure (e.g., through the pressure port 122) to the chamber, and thereby allowing the chamber to take in the new medium. The duration for the resuspension step may be about 3 seconds to about 1 minute, for example. In some implementations, to improve resuspension, various methods such as tilting of the platform, agitation (e.g., vibration of the platform), and the like may be used during the resuspension process or after the resuspension process. Step S15, however, is not limited to the resuspension step, and may also provide a cell concentration change process, a cell wash process, and/or a cell medium change process. The cell concentration change process, the cell wash process, and/or the cell medium change process may also be performed in Steps S11 and S12 by refilling the chamber after Step S12 and repeating the discharge/refill process multiple times as necessary.

After the cells are resuspended in the medium, the engineered cells are collected for further processes (Step S16). Alternatively or additionally, the engineered cells may be cultured within the chamber before they are collected and/or further processed. The platform may be flushed or washed after the process for subsequent procedures. Alternatively or additionally, the entire chamber or a part of the chamber may be made as a disposable unit that can be disposed after a use and replaced with a new one.

Figure 9B:
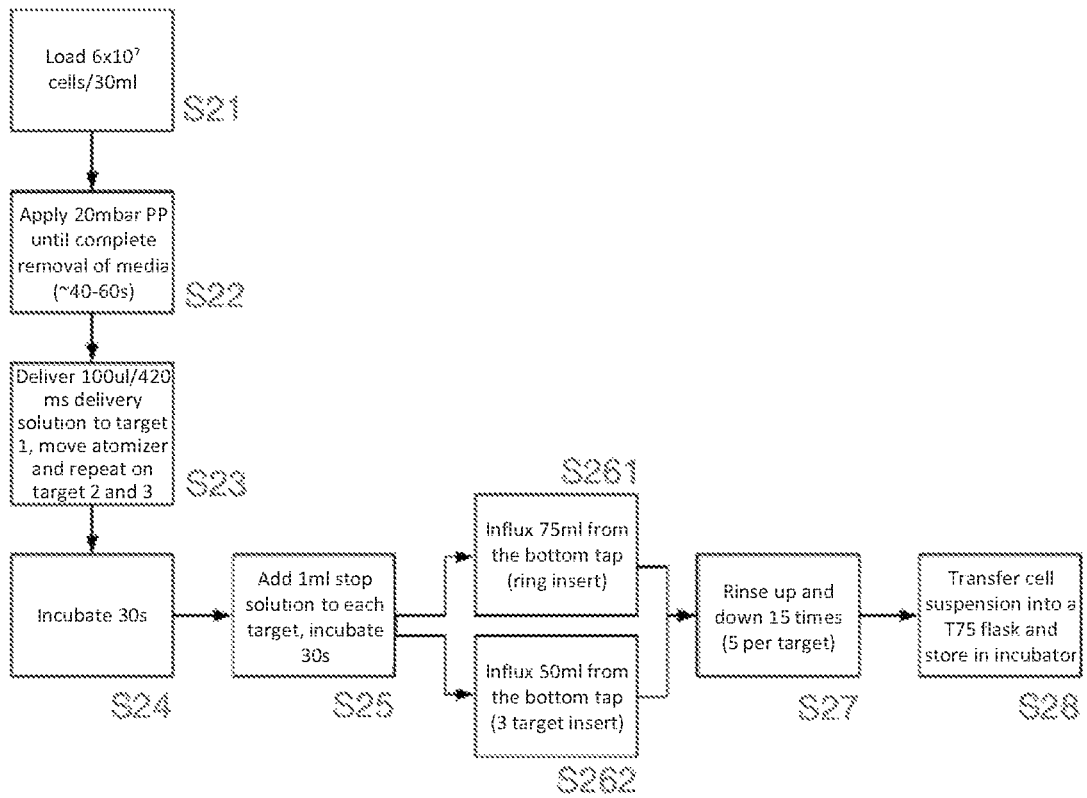
Figure 9C:
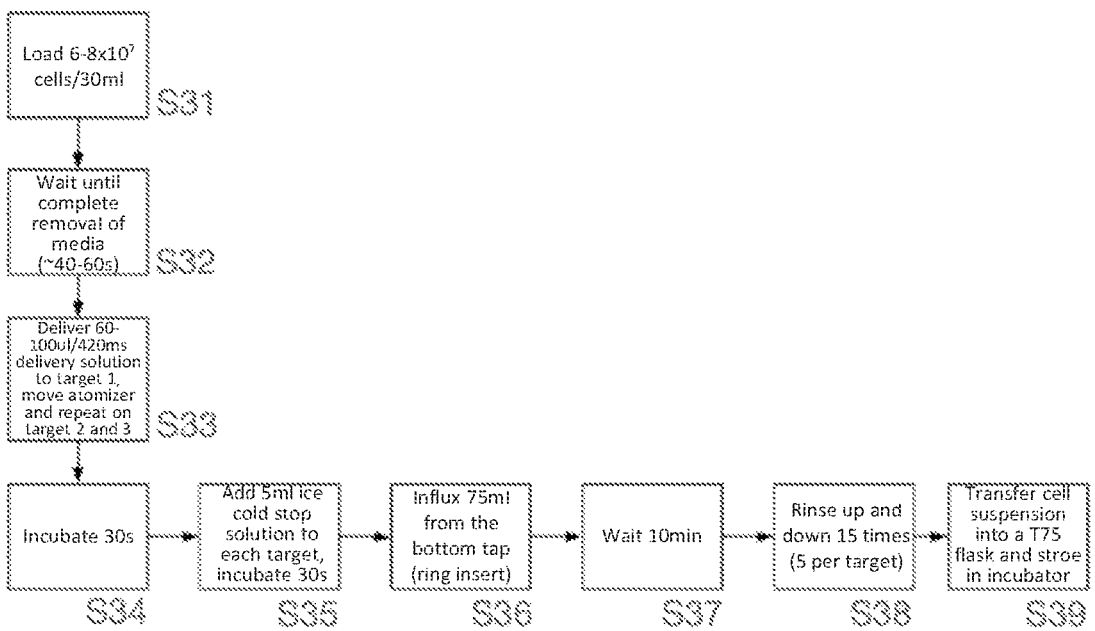

FIGS. 9B and 9C show exemplary process flows with exemplary process parameters. The process parameters, however, are not limited to those shown in FIGS. 9B and 9C, and the process parameters, such as amount (volume) of medium, number of cells, concentration, duration for each step, may be varied depending on applications. Referring to FIG. 9B, the first step may be mixing $6 \times 10^7$ cells within 30 ml media (Step S21). By applying a positive pressure of 20 mbar, the media may be removed (Step S22), which takes 40 to 60 seconds. In Step S23, 100 µL of delivery solution may be delivered over 420 ms to target 1, and subsequently, the atomizer may be moved and the delivery of the delivery solution may be repeated on targets 2 and 3. After the delivery, the cells may be incubated for 30 seconds (Step S24), and 1 mL of stop solution may be delivered to each target for 30 second incubation (Step S25). To resuspend the cells, new media may be supplied from the bottom tap. When a ring insert is used, 75 mL of media may be used (Step S261), and when a 3 target insert is used, 50 mL of media may be used (Step S262). In Step S27, the resuspended cells may be rinsed 15 times (i.e., 5 times per target). Finally, the engineered cells may be transferred into a T75 flask and stored in an incubator (Step S28).

Referring to FIG. 9C, $6 \times 10^7$ to $8 \times 10^7$ cells may be mixed within 30 ml media (Step S31). The media may be removed by means of gravity (Step S32), which takes 40 to 60 seconds. In Step S33, 60-100 µL of delivery solution may be delivered over 420 ms to target 1, and subsequently, the atomizer may be moved and the delivery of the delivery solution may be repeated on targets 2 and 3. After the delivery, the cells may be incubated for 30 seconds (Step S34), and 5 mL of stop solution may be delivered to each target for 30 second incubation (Step S35). To resuspend the cells, a media may be supplied from the bottom tap. When a ring insert is used, 75 mL of media may be used (Step S36). A step of waiting for 10 minutes may be added (Step S37). In Step S38, the resuspended cells may be rinsed 15 times (i.e., 5 times per target). Finally, the engineered cells may be transferred into a T75 flask and stored in an incubator (Step S39).

Figure 10:
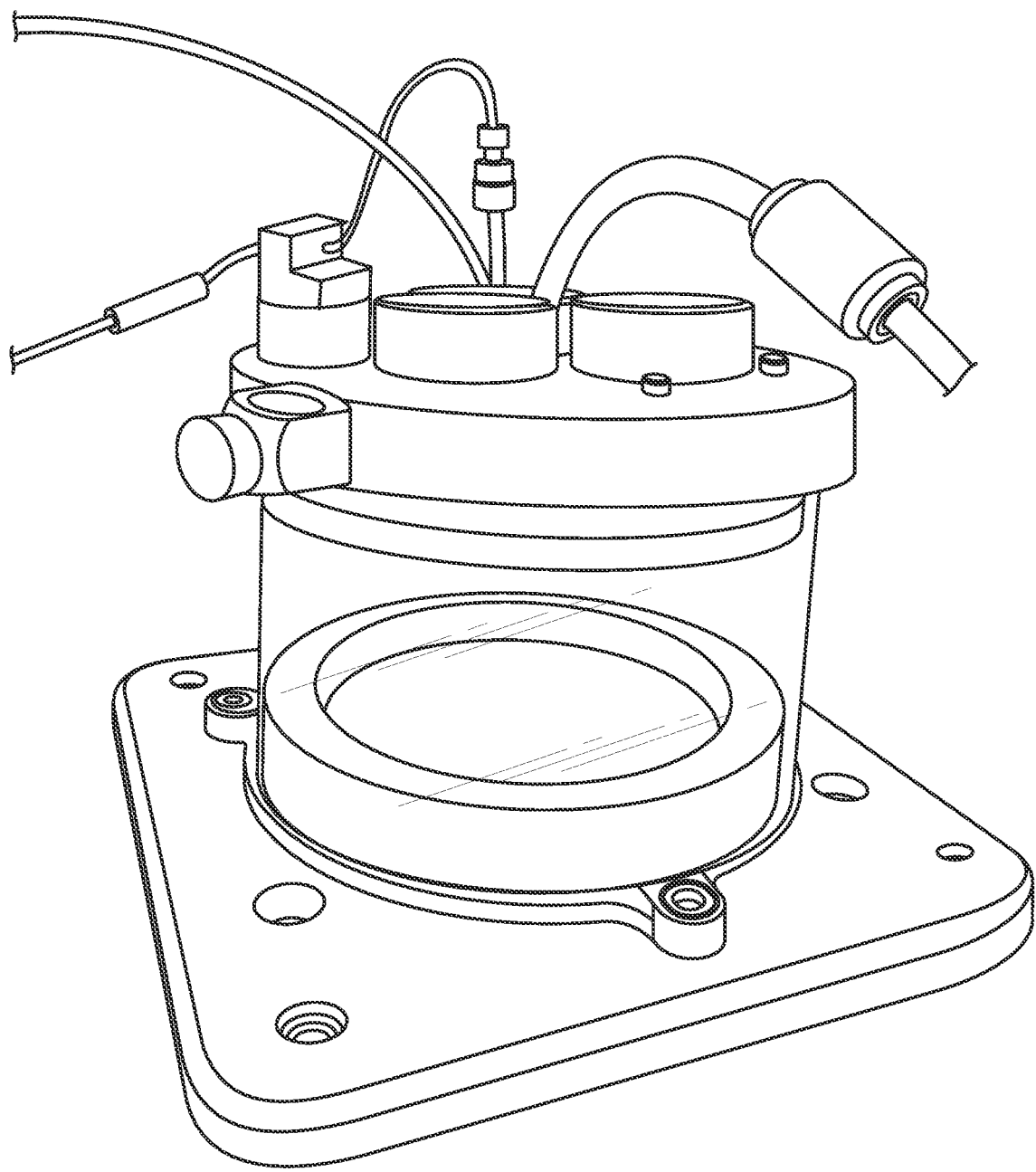
FIG. 10 shows an exemplary embodiment of the cell engineering platform.

FIG. 10 shows an exemplary embodiment of the cell engineering platform, and FIG. 11A-11C show an exemplary embodiment of the atomizer 1100 for the spraying process. Referring to FIGS. 11A-11C, the atomizer 1100 includes a liquid orifice 1101 and a gas orifice 1102 on a lower surface thereof (FIG. 11A). On an upper surface of the atomizer 1100, a liquid tubing inlet 1103 and an air tubing inlet 1104 may be formed (FIG. 11B). Accordingly, the liquid orifice 1101 is connected to a liquid reservoir through the liquid tubing inlet 1103, and the gas orifice 1102 is connected to a gas reservoir through the air tubing inlet 1104 as shown in FIG. 11C. The gas reservoir may be an air cylinder or an air pump, and may be provided with a valve.

The gas (e.g., air) flow may be controlled by a mass flow controller or a volumetric flow controller. By using the mass/volume flow controller, a constant amount (e.g., a constant mass and/or a constant volume) of gas may be supplied through the atomizer 1100, thereby ensuring a constant amount of liquid to be sprayed and the droplet sizes to be maintained consistently, regardless of pressure, temperature, humidity, on/off timing variations in the chamber, or the like. Mass/volume flow regulation may also permit more accurate and repeatable dosing of atomized solution to the cells. By actively controlling the mass/volume flow rate of the driving gas, the spray plume is less susceptible to variability in plume density, angle, velocity, vortex formation, droplet size, deposition area, or the like, which results in more repeatable and consistent transfection performance.

Figure 11E:
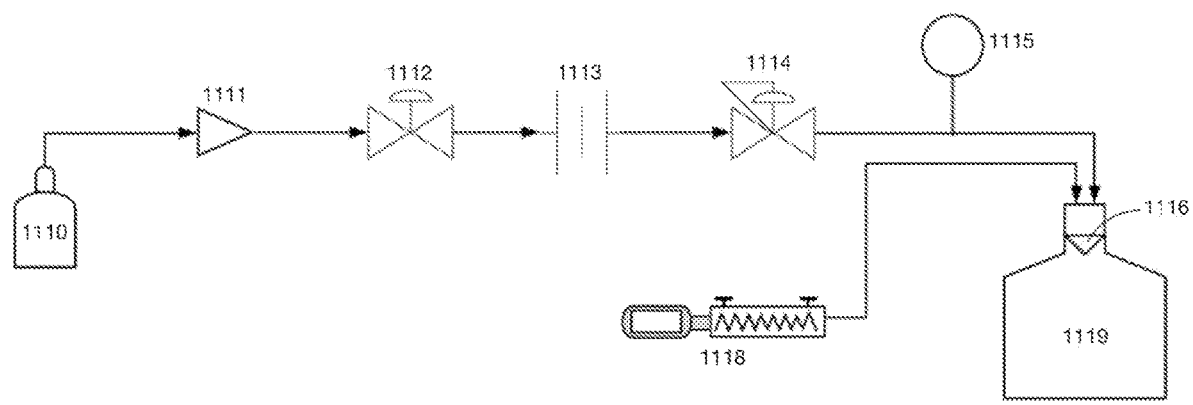
FIGS. 11E-11G show schematics of mass flow regulation for atomizer operation.
Figure 11F:
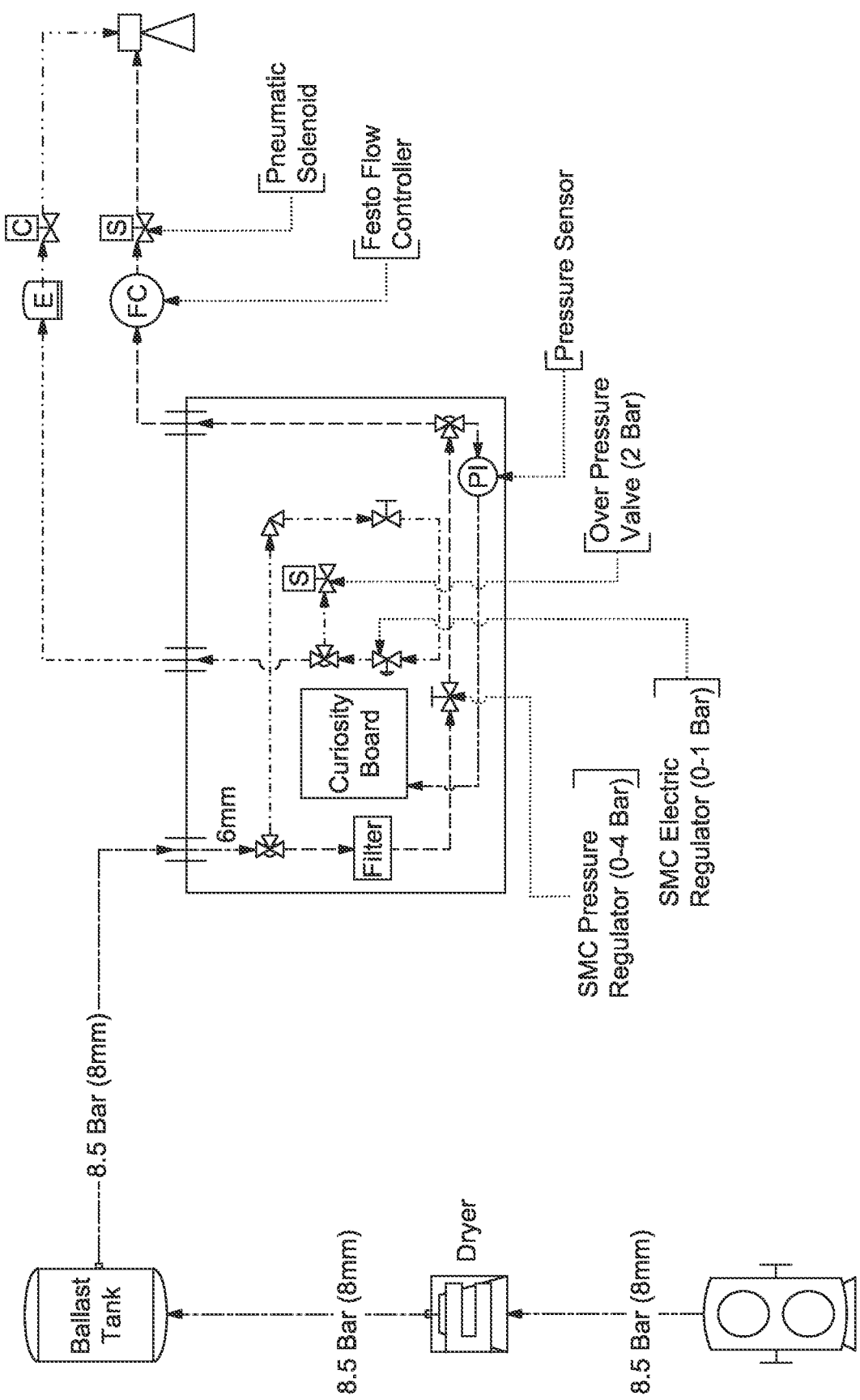
Figure 11G:
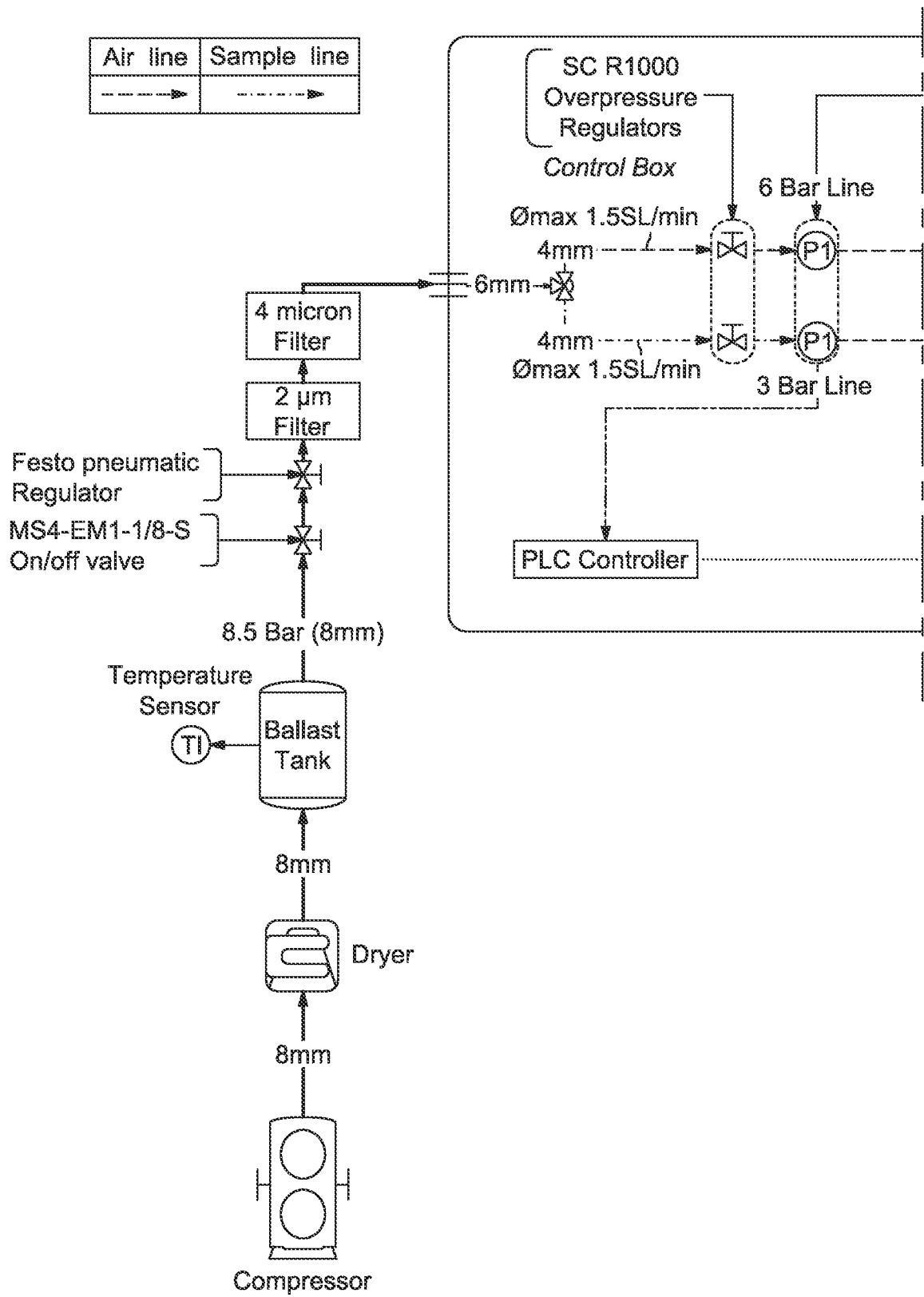
Figure 11G:
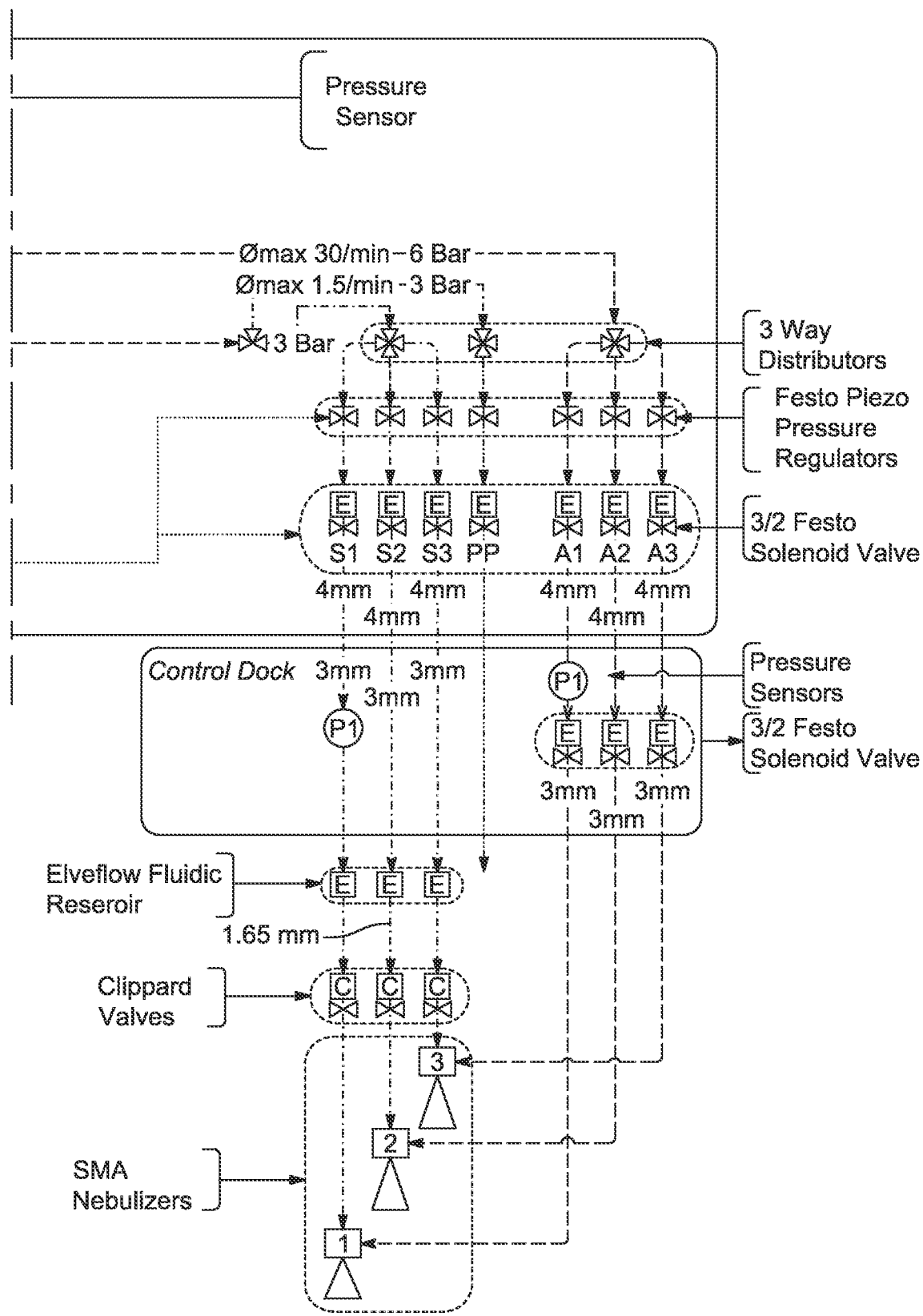
Figure 11G:
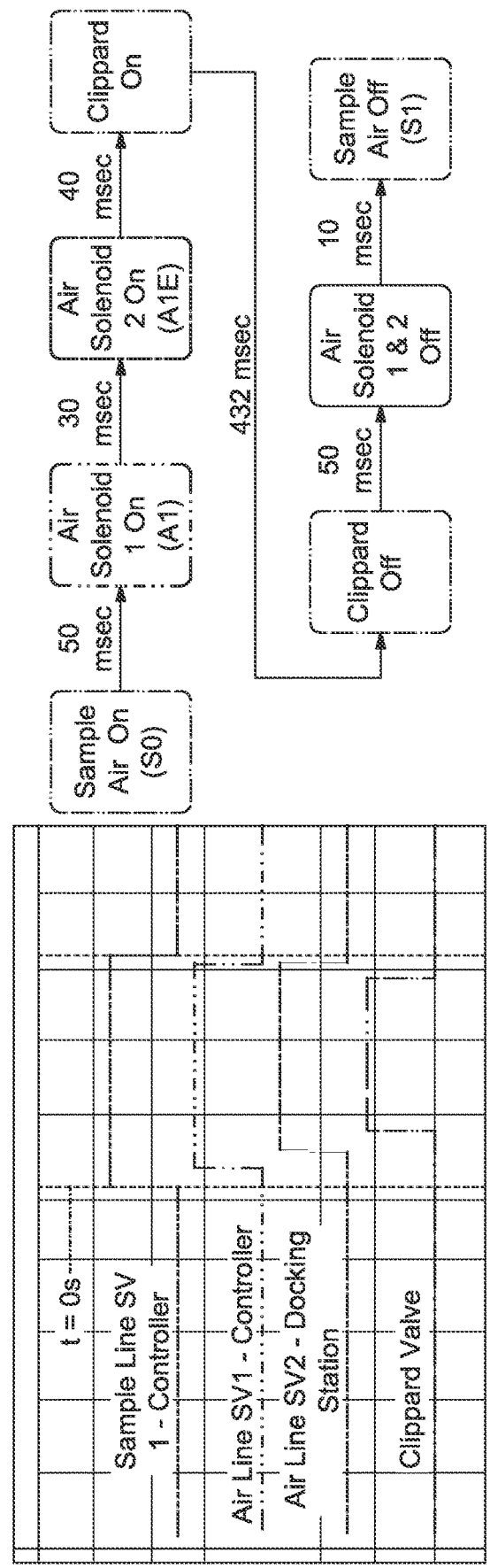

FIG. 11E shows an example pneumatic circuit for the mass/volume flow regulation of the driving gas. The driving gas may be supplied from a gas cylinder 1110, pass through a gas supply 1111, a control valve 1112, an orifice 1113, and a back pressure regulator 1114. Subsequently, the gas may be controlled by a mass/volume flow controller 1115 before it is delivered to the atomizer 1116 through a gas line 1117. The solution to be sprayed may be supplied by a pump 1118. The pump 1118 may be a screw pump, positive displacement pump, a gas driven fluidic pump, or the like. Accordingly, the solution may be sprayed through the atomizer 1116 and delivered into the chamber 1119. FIGS. 11F and 11G show examples of control and fluidic pathways for the spray operation. FIG. 11F shows the pathways for one spray head, and FIG. 11G shows the pathways for three spray heads.

Figure 12:
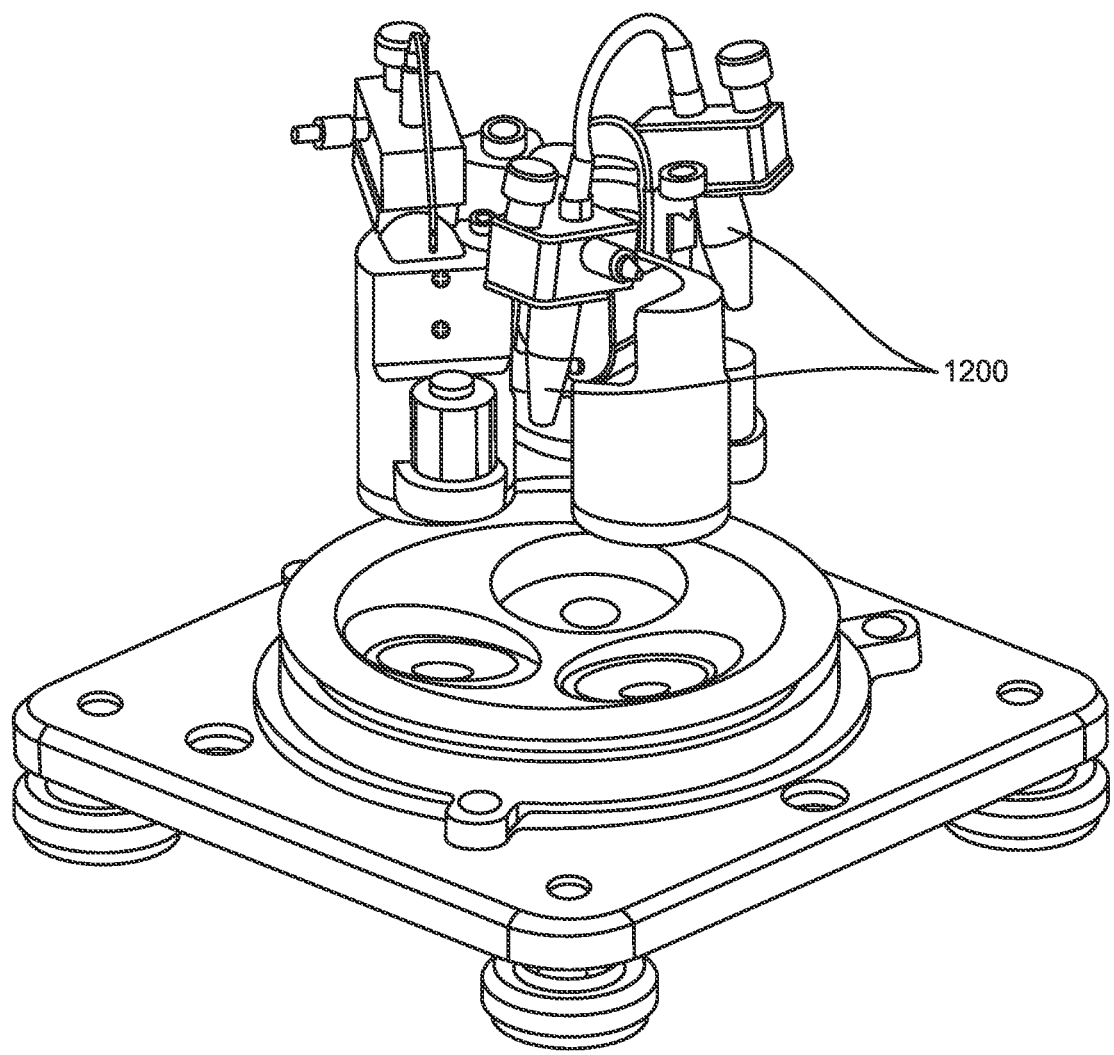
FIG. 12 is a computer aided design (CAD) drawing illustrating an exemplary embodiment in which three spray heads are mounted.
Figure 13:
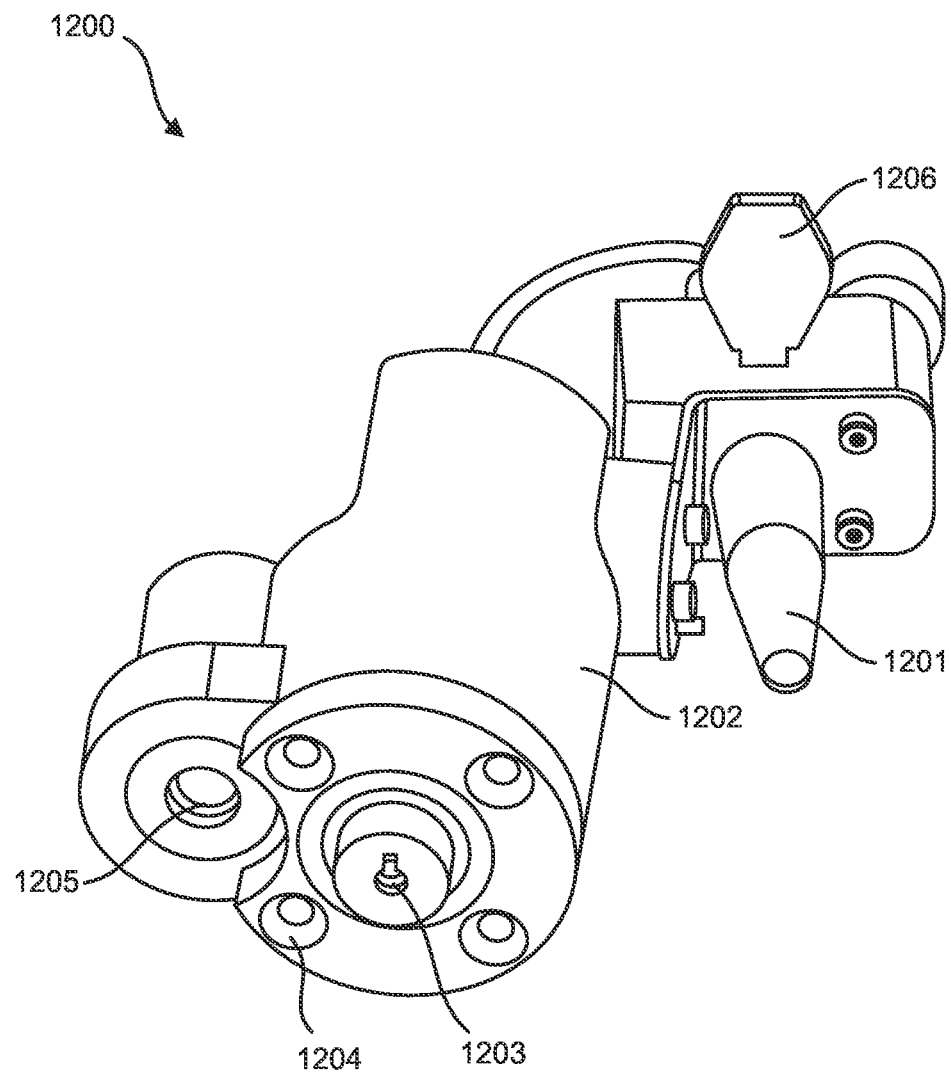
FIG. 13 shows a CAD drawing for one spray head.

FIG. 12 is a computer aided design (CAD) drawing illustrating an exemplary embodiment in which three spray heads 1200 are mounted. FIG. 13 shows a CAD drawing for one of the spray heads 1200. Referring to FIG. 13, the spray head 1200 includes a spraying nozzle 1203, a local fluidic reservoir 1201, and a lid of the local fluidic reservoir 1206, supported on a cylindrical substrate 1202. Threaded holes 1204 permit affixing of the spray head to the chamber. The cylindrical substrate 1202 includes a valve 1205, for example, a pinch valve to start and/or stop the fluid flow from the reservoir.

Figure 14A:
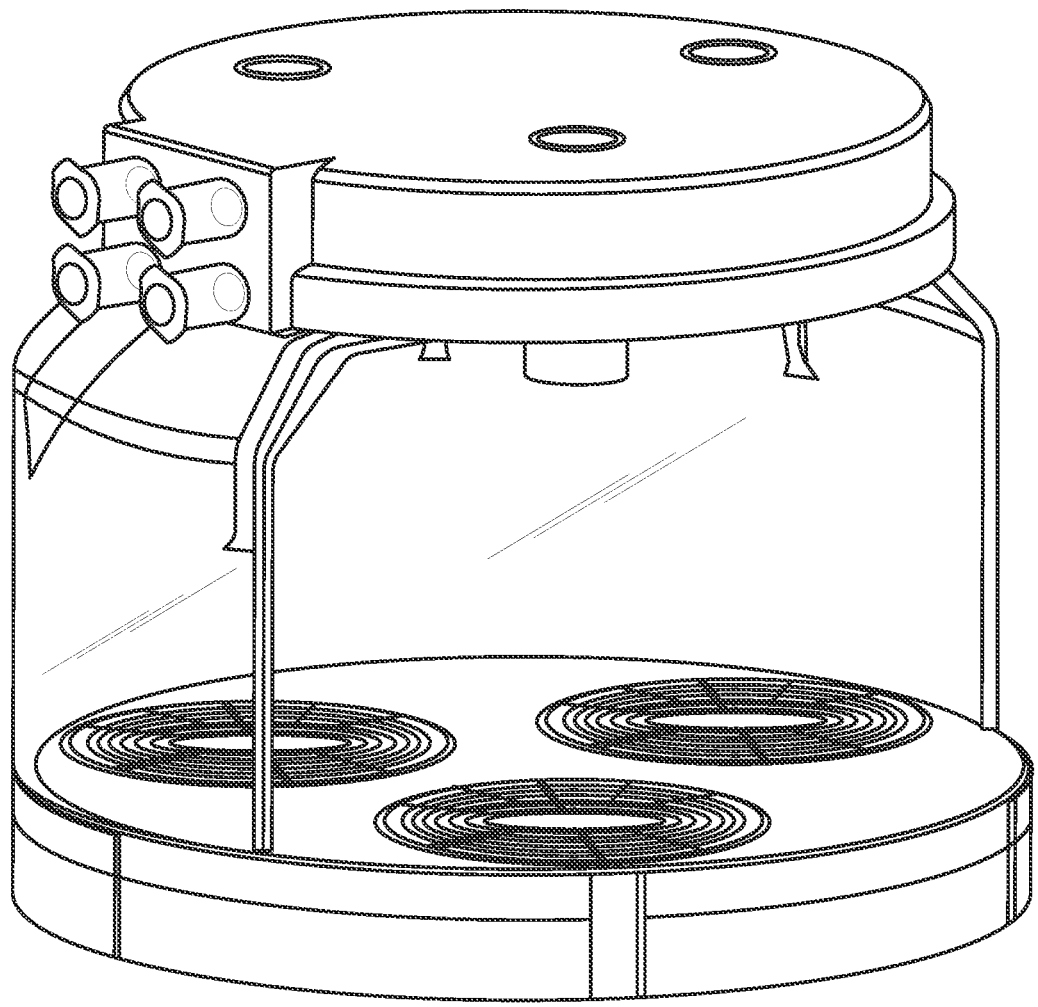
FIGS. 14A-14F show exemplary implementations of a disposable chamber assembly.
Figure 14B:
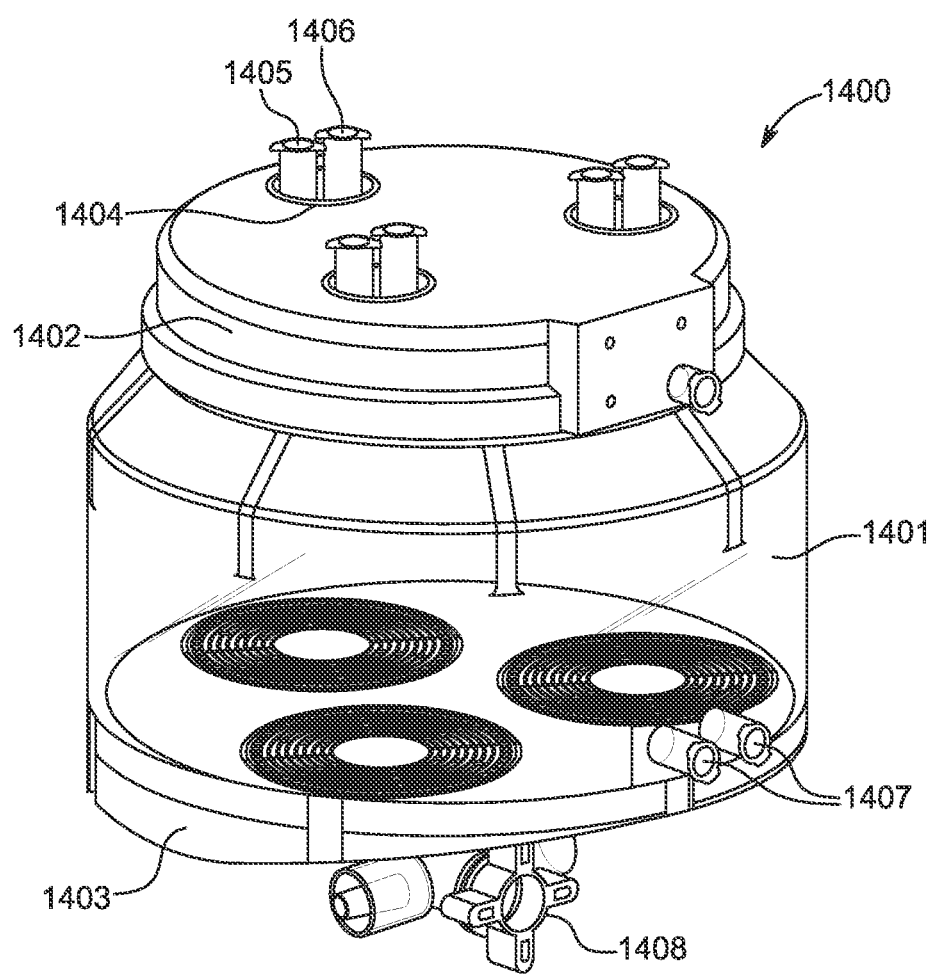
Figure 14C:
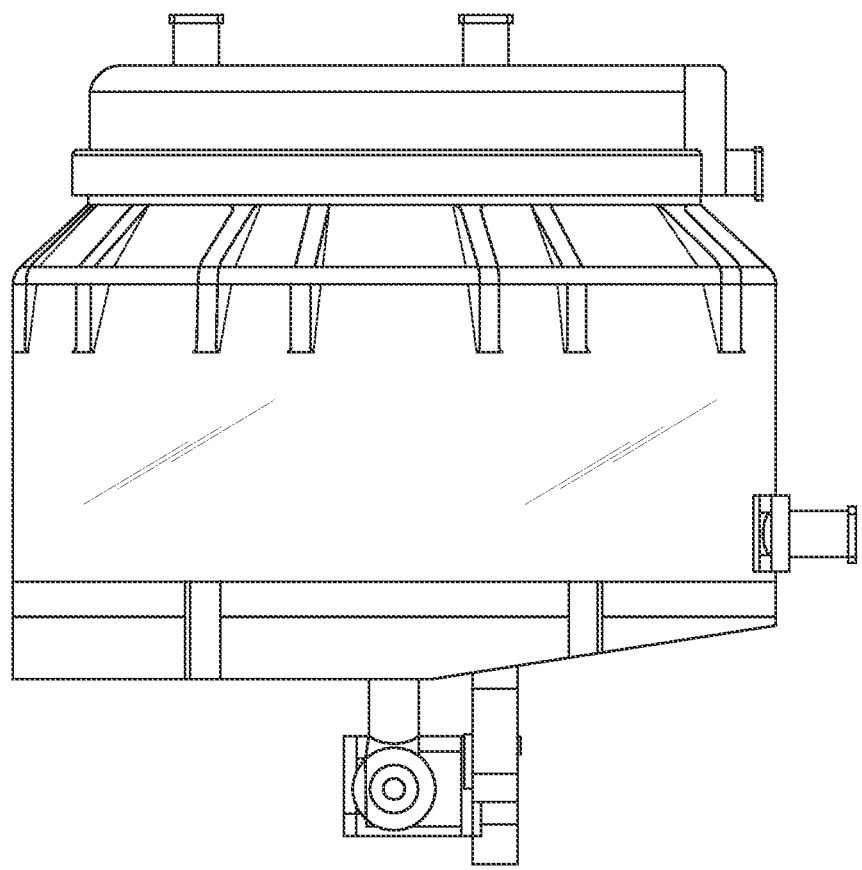
Figure 14D:
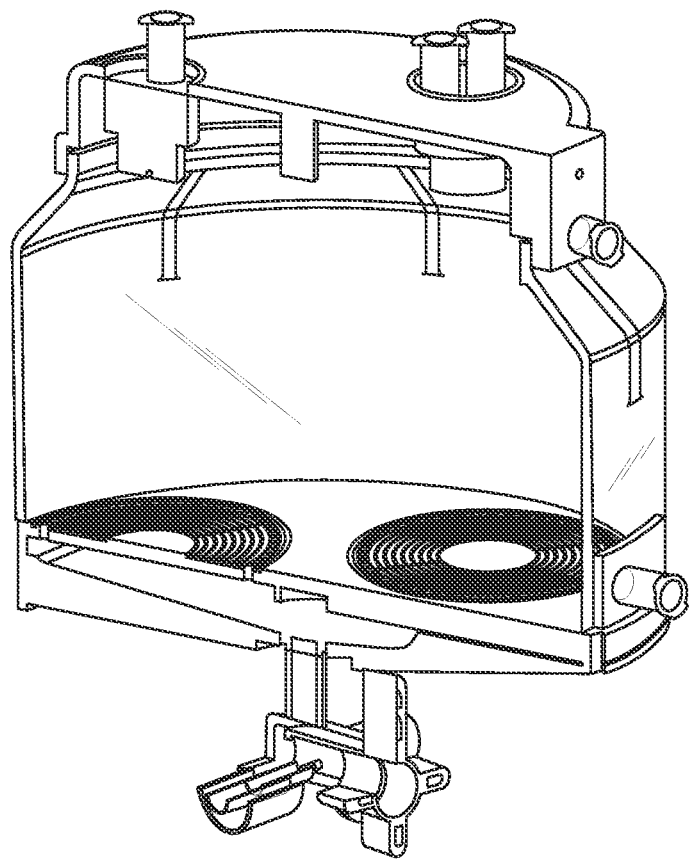
Figure 14E:
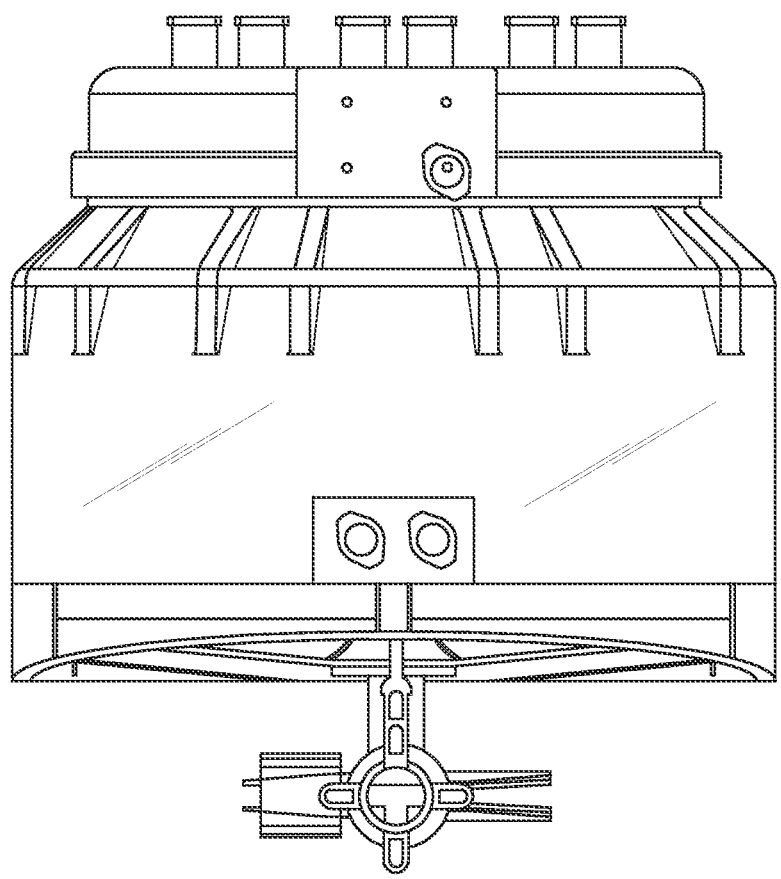
Figure 14F:
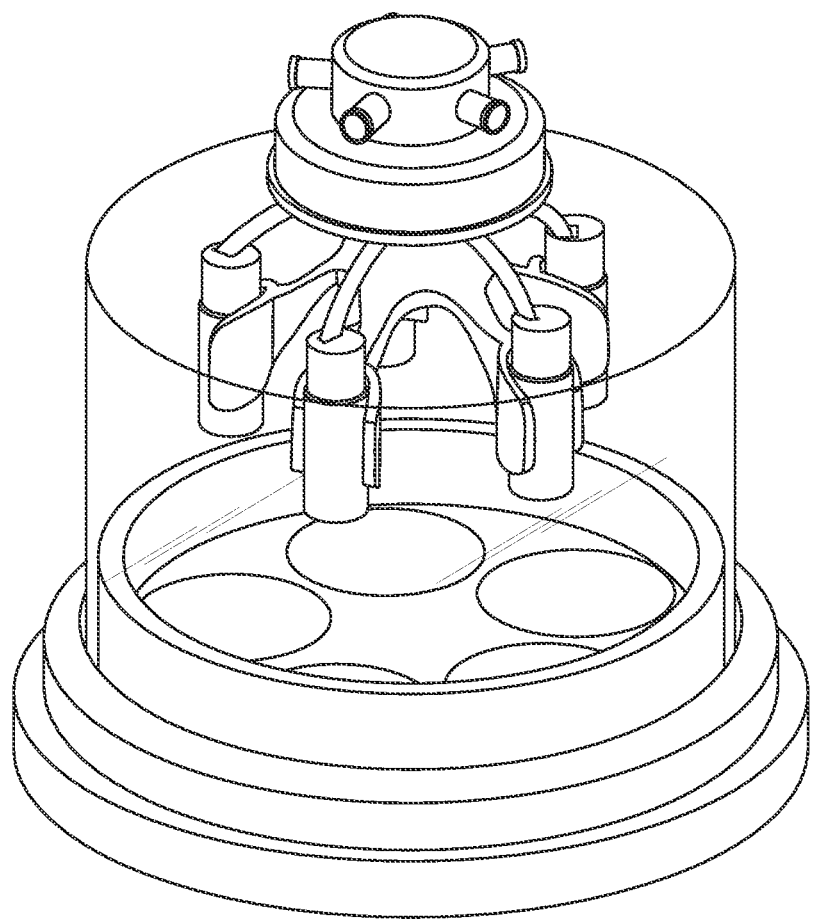

FIGS. 14A-14F show exemplary implementations of a disposable chamber assembly. Referring to FIG. 14B, the example disposable chamber assembly 1400 may include a chamber wall 1401 made of, for example, polycarbonate, a seam welded lid module 1402, a base module 1403 with welded membrane, atomizer mounting apertures 1404, cells in/out ports 1407, and a three-way valve 1408. To operate the atomizer, payload and delivery solution may be supplied through a media port 1405, and pressurized air may be supplied through an air pressure port 1406. FIG. 14C shows a side view of the example disposable chamber assembly, FIG. 14D shows a cutout view of the example disposable chamber assembly, and FIG. 14E shows a front view of the example disposable chamber assembly. FIG. 14F shows another example disposable chamber assembly with five targets and five spray heads.

Figure 15B:
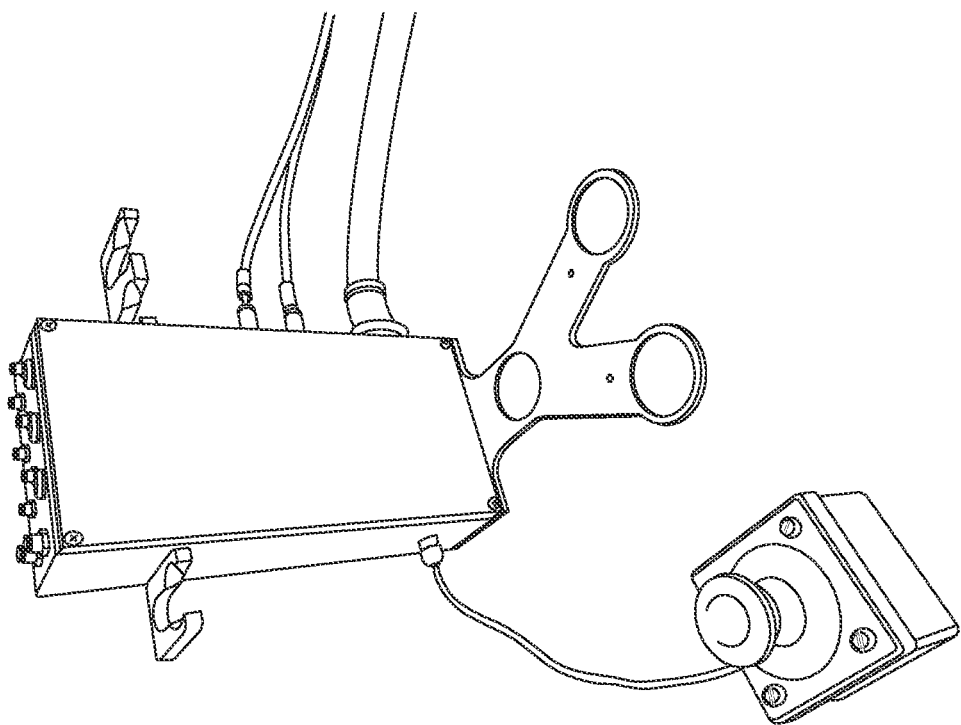
FIG. 15B shows an image of the platform with the chamber removed.
Figure 15A:
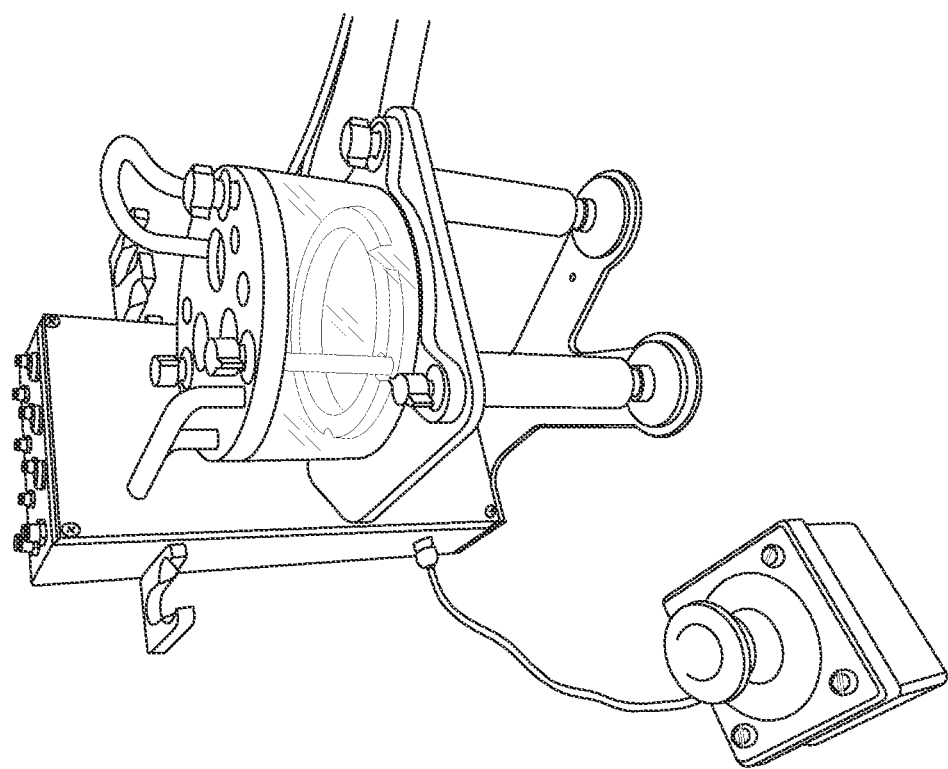
FIG. 15A shows an image of an exemplary embodiment of the cell engineering platform with a support system and a mounting stand.

FIG. 15A shows an exemplary embodiment of the cell engineering platform with a support system and a mounting stand, and FIG. 15B shows the platform with the chamber removed.

The exemplary embodiments described in the Example 1 section can transfect from about $10^7$ to about $10^9$ cells or more in a single transfection. The platform can allow consistent delivery of cargos, such as mRNA and the like, to T cells. The system may be enclosed within a biosafety cabinet for a sterile operation, or may be made as a closed system to be used in any environment. The operation of the platform may be performed manually or automatically. For the automated operation, the fluid handling system can be controlled automatically via the controller and control software. The platform may be configured as a multiple-use system, which can be reused after cleaning and washing. In some implementations, the platform may be configured as a single use disposable system, which includes disposable parts such as a disposable chamber unit. In some implementations, the platform may be used for the vector-free payload delivery across cell membranes and/or the viral payload delivery across cell membranes.

Due to the process automation, the cell engineering platform can perform the vector-free payload delivery process more consistently, contamination can be minimized, and therefore, the system can be scaled. Accordingly, the cell engineering platform can provide reliable vector-free delivery method to reduce the cost and complexity of the cell engineering technologies.

Example 2

Figure 16:
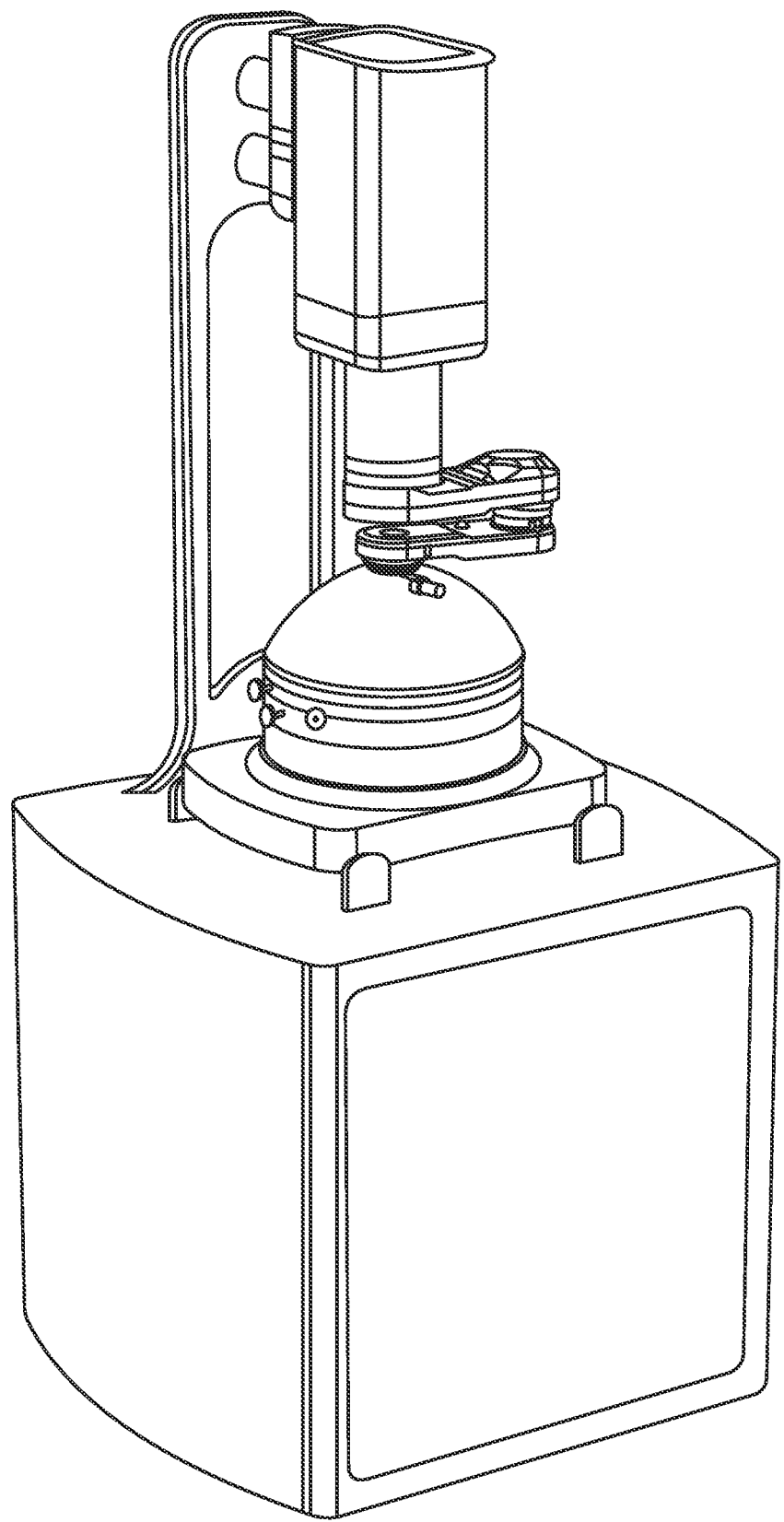
FIG. 16 is a computer aided design (CAD) drawing illustrating an example clinical cell engineering platform for cell therapies.
Figure 17:
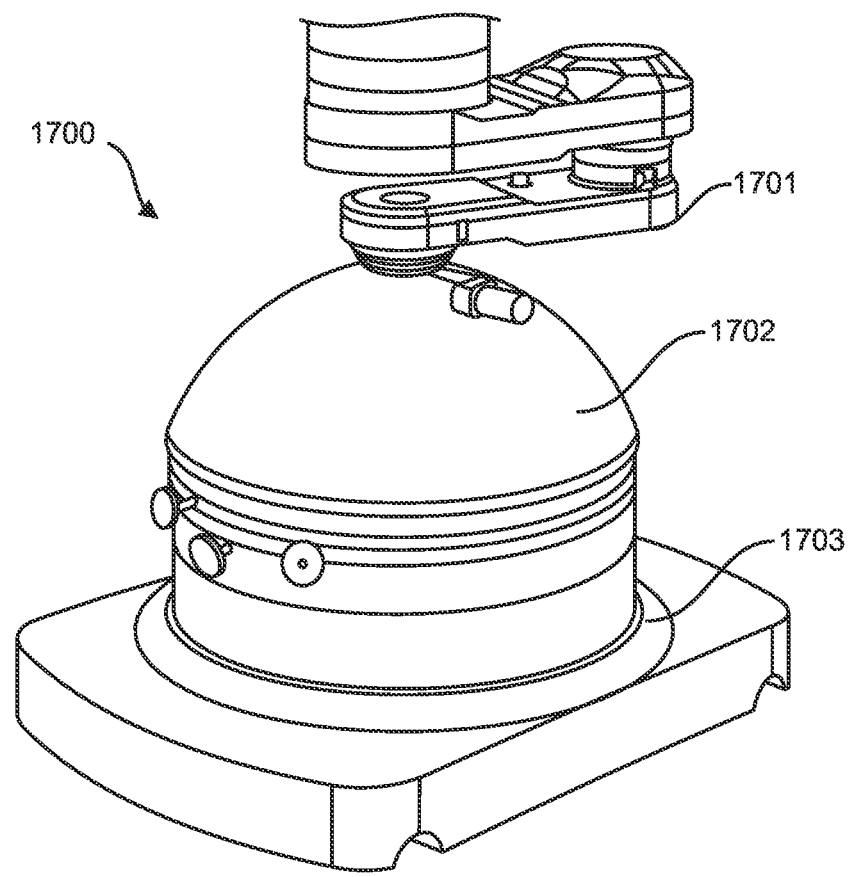
FIG. 17 is a magnified view of a portion of the platform.

FIG. 16 is a computer aided design (CAD) drawing illustrating another example clinical cell engineering platform for cell therapies and FIG. 17 is a magnified view of a portion of the platform. The platform 1700 includes a robotic arm 1701 that carries a spray head, a soft elastomeric dome 1702 enclosing a filter base 1703 and the spay head. The platform further includes media, reagents, cargo, and waste ports, enabling a closed system.

The robotic arm 1701 can carry the spray head to multiple locations within the elastomeric dome 1702 for spraying solution onto cells formed into a monolayer on the filter base 1703. In addition, the filter base 1703 can tilt and rotate to bath cells with reagents.

Figure 18:
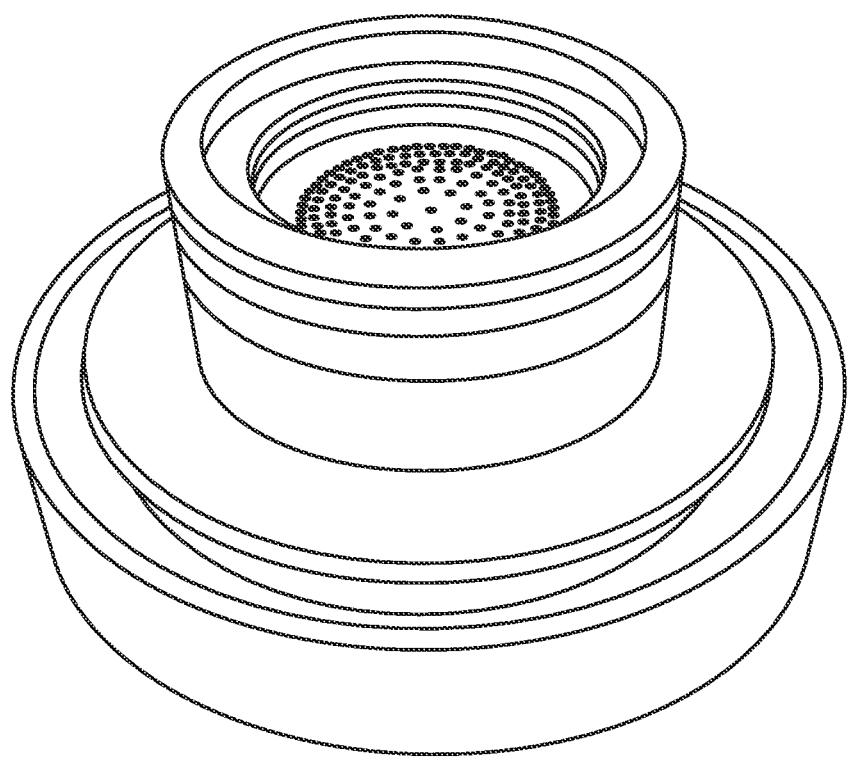
FIG. 18 is a CAD drawing illustrating an example filter plate and filter.

FIG. 18 is a CAD drawing illustrating an example filter plate and filter. In order to effectuate delivery, a cellular mono can be formed on the filter plate. Positive pressure is applied to the vessel. Pinch valves on inputs and outputs can be closed during the positive pressure. The filter can be track etched and single use according to an activation regime. The filter holder includes a hole pattern designed to aid media removal completely and rapidly. In operation, the spraying can occur immediately after monolayer formation.

FIG. 19 is a CAD drawing illustrating a cross-sectional view of the example platform and rotation of the filter plate. The platform 1700 is shaped to collect waste media under the filter plate. The platform 1700 may include a soft elastomeric dome 1702, circumferential ports 1704 for media and stop solution, a filter substrate 1705, a waste media plenum 1706, and a tilt/rotate unit 1707. The filter substrate 1705 may be molded from polysulfone may form a stencil when media is pressurized off the cells. In operation, the unit can tilt and rotate to remove cells suspended in new media.

Figure 20C:
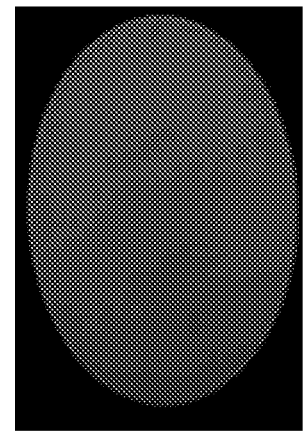
FIGS. 20A-20C show a series of pictures illustrating components of an example implementation of the platform.
Figure 20B:
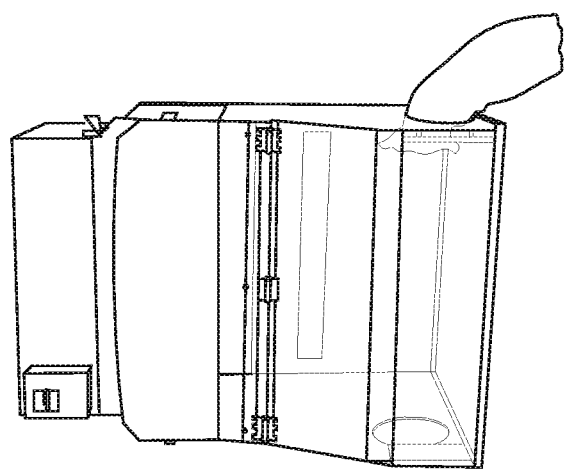
Figure 20A:
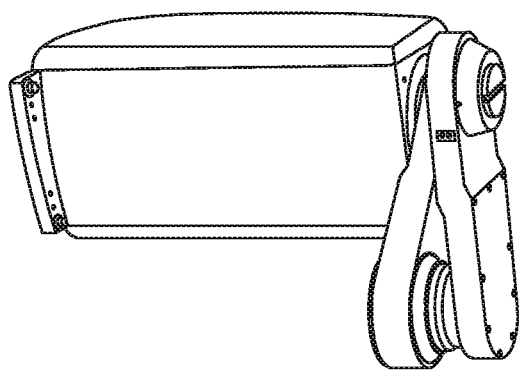

FIGS. 20A-20C are a series of pictures illustrating components of an example implementation of the platform. FIG. 20A shows an example robotic arm, FIG. 20B shows an example safe enclosure to house the platform, and FIG. 20C shows an example filter disk. The filter disk may be a polycarbonate track etched (PCTE) filter having a diameter of 293 mm.

Figure 21:
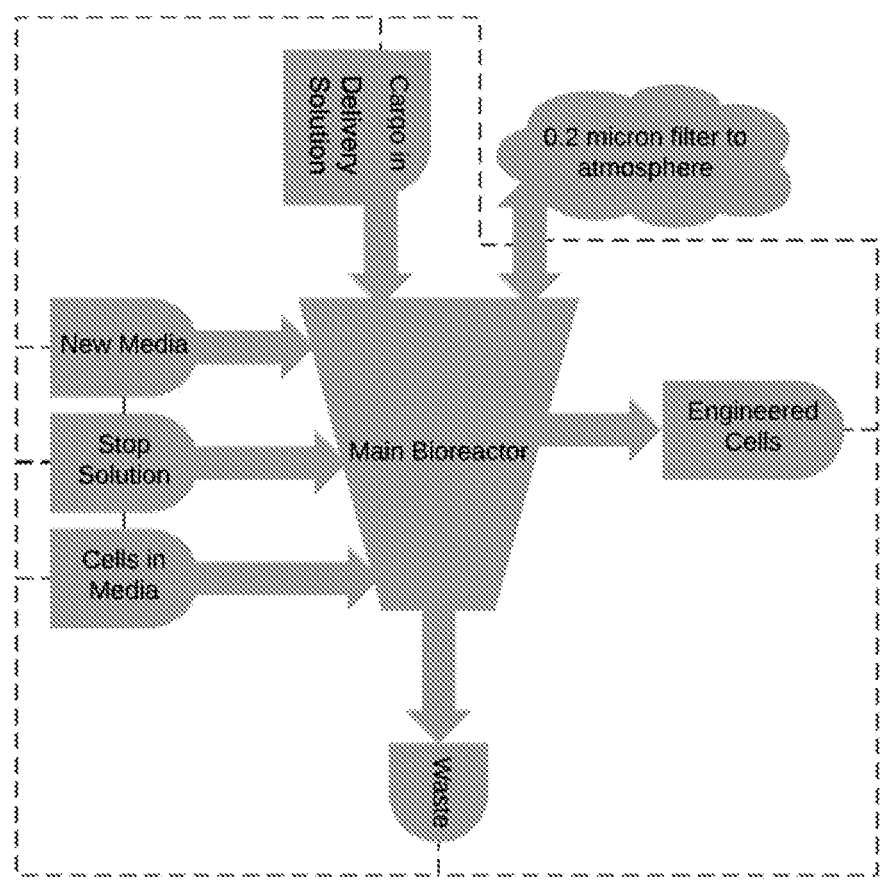
FIG. 21 is a functional block diagram of an example platform.

FIG. 21 is a functional block diagram of an example platform. The platform includes modules for applying new media, stop solution, cells in media, and cargo in the delivery solution into the main bioreactor. In addition, the platform can include a 0.2 micron to atmosphere filter. The platform can conduct the delivery protocol utilizing the inputs and outputting waste and engineered cells.

Figure 22:
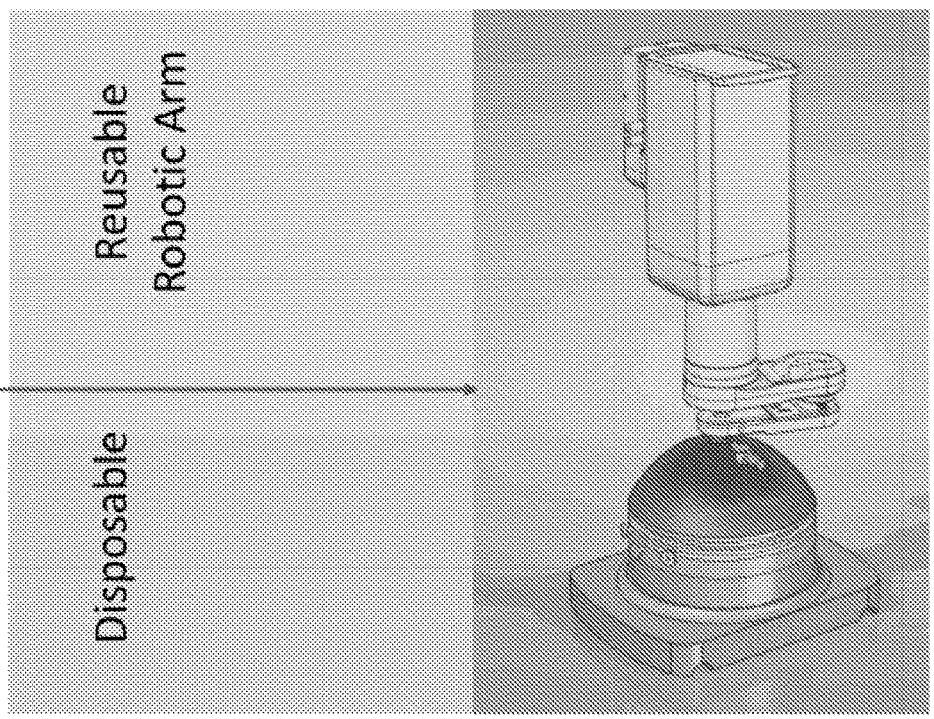
FIG. 22 is a diagram illustrating disposable and reusable portions of the example platform.

FIG. 22 is a diagram illustrating disposable and reusable portions of the example platform. The robotic arm can be magnetically coupled to the closed cartridge, which can include a single use cartridge that keeps the local environment between the spray head and filter base. Single-use tubing can carry fluids in and out of the bioreactor. The cargo can be introduced in the delivery solution via a syringe or other means.

FIG. 23 is a table illustrating some example performance capabilities for the example platform. In some embodiments, the system input can include cells, culture media, molecular cargo, stop solution and air and/or gas. While performing the vector-free payload delivery, relevant regulations and standards are applied as protocols. The relevant standards include current Good Automated Manufacturing Practice (cGAMP), ASTM E2500, ISO 14791, 21 CFR § 211.68, and 21 CFR § 1271.160 [d].

In some embodiments, the cells can include adherent cells or non-adherent cells. The adherent cells can include at least one of primary mesenchymal stem cells, fibroblasts, monocytes, macrophages, lung cells, neuronal cells, fibroblasts, human umbilical vein (HUVEC) cells, Chinese hamster ovary (CHO) cells, and human embryonic kidney (HEK) cells or immortalized cells, such as cell lines. In preferred embodiments, the population of cells comprises non-adherent cells, e.g., the % non-adherent cells in the population is at least 50%, 60%, 75%, 80%, 90%, 95%, 98%, 99% or 100% non-adherent cells. Non-adherent cells primary cells as well as immortalized cells (e.g., cells of a cell line). Exemplary non-adherent/suspension cells include primary hematopoietic stem cell (HSC), T cells (e.g., (cluster of differentiation 3) CD3+ cells, (cluster of differentiation 4) CD4+ cells, (cluster of differentiation 8) CD8+ cells), natural killer (NK) cells, cytokine-induced killer (CIK) cells, human cord blood CD34+ cells, B cells, or cell lines such as Jurkat T cell line. Non limiting examples of T cells may include CD8+ or CD4+ T cells. In some aspects, the CD8+ subpopulation of the CD3$^+$ T cells are used. CD8$^+$ T cells may be purified from the PBMC population by positive isolation using anti-CD8 beads.

In examples, cells are cultured in standard cell culture media, e.g., complete RPMI (Roswell Park Memorial Institute medium) using RPMI basal medium, heat-inactivated fetal bovine serum (FBS), e.g., about 10% v/v, penicillin-streptomycin, and L-glutamine. In some examples, the standard culture media can be supplemented with cytokines, e.g., Interleukin-2 (IL-2) (200 U/ml).

In embodiments, the cytokines can be at a concentration from about 10 U/ml to about 500 U/ml. In other examples, the cytokines can be at a concentration of about 50 U/ml, about 100 U/ml, about 200 U/ml, about 300 U/ml, about 400 U/ml, or about 500 U/ml. The cytokine concentration can be about 200 U/ml.

In some examples, cell-compatible culture media are used in the delivery methods. For example, Prime-XV (Irvine Scientific) and X-Vivo (Lonza) are serum-free and animal component free media that can be used.). In some examples, the cell culture media was supplemented with a higher concentration of cytokines. The cytokines can include, for example, interleukin-2 (IL-2), to enhance the rate of proliferation (Tumeh P, et al., *J Immunother* 2010. 33 (6): 759-768 and Besser M J, et al., *Cytotherapy* 2009. 11:206-217). In other examples, the culture medium can include Immunocult™-XF Expansion Medium (StemCell Technologies). Like Prime XV, it is also a serum-free, xeno-free T cell culture medium. In some examples, TexMACS (Miltenyi Biotech) may be used as an alternative serum-free medium for T-cell culture. CTS OpTmizer T Cell Expansion SFM may also be used as an alternative serum-free medium for T cell culture.

In embodiments, the molecular cargo (e.g., payload) can include gene editing tools, a small chemical molecule, a peptide or protein, or a nucleic acid. The payload can comprise a messenger ribonucleic acid (mRNA). The mRNA can encode a gene-editing composition. The mRNA can encode a chimeric antigen receptor.

In additional embodiments, the molecular cargo (e.g., payload) to be delivered may include a composition that edits genomic DNA (i.e., gene editing tools). For example, the gene editing composition may include a compound or complex that cleaves, nicks, splices, rearranges, translocates, recombines, or otherwise alters genomic DNA. Alternatively or in addition, a gene editing composition may include a compound that (i) may be included a gene-editing complex that cleaves, nicks, splices, rearranges, translocates, recombines, or otherwise alters genomic DNA; or (ii) may be processed or altered to be a compound that is included in a gene-editing complex that cleaves, nicks, splices, rearranges, translocates, recombines, or otherwise alters genomic DNA. In various embodiments, the gene editing composition comprises one or more of (a) gene editing protein; (b) RNA molecule; and/or (c) ribonucleoprotein (RNP).

In some embodiments, the gene editing composition comprises a gene editing protein, and the gene editing protein is a zinc finger nuclease (ZFN), a transcription activator-like effector nuclease (TALEN), a Cas protein, a Cre recombinase, a Hin recombinase, or a Flp recombinase. In additional embodiments, the gene editing protein may be a fusion proteins that combine homing endonucleases with the modular DNA binding domains of TALENs (megaTAL). For example, megaTAL may be delivered as a protein or alternatively, a mRNA encoding a megaTAL protein is delivered to the cells.

In embodiments, the molecular cargo (e.g., payload) can include a small chemical molecule. The small chemical molecule can be less than 1,000 Da. The chemical molecule can include MitoTracker® Red CMXRos, propidium iodide, methotrexate, and/or DAPI (4',6-diamidino-2-phenylindole).

In embodiments, the molecular cargo can be a peptide. The peptide can be about 5,000 Da. The peptide can include ecallantide under trade name Kalbitor, is a 60 amino acid polypeptide for the treatment of hereditary angioedema and in prevention of blood loss in cardiothoracic surgery), Liraglutide (marketed as the brand name Victoza, is used for the treatment of type II diabetes, and Saxenda for the treatment of obesity), and Icatibant (trade name Firazyr, a peptidomimetic for the treatment of acute attacks of hereditary angioedema). The small-interfering ribonucleic acid (siRNA) molecule can be about 20-25 base pairs in length, or can be about 10,000-15,000 Da. The siRNA molecule can reduces the expression of any gene product, e.g., knockdown of gene expression of clinically relevant target genes or of model genes, e.g., glyceraldehyde-3phosphate dehydrogenase (GAPDH) siRNA, GAPDH siRNA-FITC, cyclophilin B siRNA, and/or lamin siRNA. Protein therapeutics can include peptides, enzymes, structural proteins, receptors, cellular proteins, or circulating proteins, or fragments thereof. The protein or polypeptide be about 100-500,000 Da, e.g., 1,000-150,000 Da. The protein can include any therapeutic, diagnostic, or research protein or peptide, e.g., beta-lactoglobulin, ovalbumin, bovine serum albumin (BSA), and/or horseradish peroxidase. In other examples, the protein can include a cancer-specific apoptotic protein, e.g., Tumor necrosis factor-related apoptosis inducing protein (TRAIL).

An antibody is generally be about 150,000 Da in molecular mass. The antibody can include an anti-actin antibody, an anti-GAPDH antibody, an anti-Src antibody, an anti-Myc ab, and/or an anti-Raf antibody. The antibody can include a green fluorescent protein (GFP) plasmid, and a GLuc plasmid. The DNA molecule can be greater than 5,000,000 Da. In some examples, the antibody can be a murine-derived monoclonal antibody, e.g., ibritumomab tiuxetin, muromomab-CD3, tositumomab, a human antibody, or a humanized mouse (or other species of origin) antibody. In other examples, the antibody can be a chimeric monoclonal antibody, e.g., abciximab, basiliximab, cetuximab, infliximab, or rituximab. In still other examples, the antibody can be a humanized monoclonal antibody, e.g., alemtuzamab, bevacizumab, certolizumab pegol, daclizumab, gentuzumab ozogamicin, trastuzumab, tocilizumab, ipilimumamb, or panitumumab. The antibody can comprise an antibody fragment, e.g., abatacept, aflibercept, alefacept, or etanercept. The invention encompasses not only an intact monoclonal antibody, but also an immunologically-active antibody fragment, e.g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

The molecular cargo (e.g., payload) can include a therapeutic agent. A therapeutic agent, e.g., a drug, or an active agent", can mean any compound useful for therapeutic or diagnostic purposes, the term can be understood to mean any compound that is administered to a patient for the treatment of a condition. Accordingly, a therapeutic agent can include, proteins, peptides, antibodies, antibody fragments, and small molecules. Therapeutic agents described in U.S. Pat. No. 7,667,004 "Humanized antibodies against vascular endothelial growth factor" (incorporated herein by reference) can be used in the methods described herein. The therapeutic agent can include at least one of cisplatin, aspirin, statins (e.g., pitavastatin, atorvastatin, lovastatin, pravastatin, rosuvastatin, simvastatin, promazine hydrochloric acid (HCl), chloropromazine HCl, thioridazine HCl, Polymyxin B sulfate, chloroxine, benfluorex HCl and phenazopyridine HCl), and fluoxetine. The payload can include a diagnostic agent. The diagnostic agent can include a detectable label or marker such as at least one of methylene blue, patent blue V, and indocyanine green. The payload can include a fluorescent molecule. The payload can include a detectable nanoparticle. The nanoparticle can include a quantum dot.

In some implementations, the cargo can include linear DNA or DNA plasmid.

In an example, following delivery, the cells are incubated prior to the addition of Stop Solution. In examples, the Stop Solution includes phosphate buffered saline (PBS). The concentration of PBS can be about 0.5×PBS.

In some implementations, the delivery solution can be formulated by a GMP (Good Manufacturing Provider) provider and can be provided in a foil-top 10 mL vial. Separate drug master file (DMF) put on file for delivery solution. Stability testing and Certificate of Analysis (C of A) provided, and suppliers of current Good Manufacturing Practices (cGMPs) are utilized.

FIG. 24 is a table illustrating compatible technologies that the example platform can be integrated with. For example, various selection/isolation/enrichment kits can be used. Also, various activation and stimulation technologies can be used, including, for example, Anti-CD3 (cluster of differentiation 3) mAb (monoclonal antibody) Muromonab-CD3 (OKT3) and Interleukin 2 (IL-2), CD3/cluster of differentiation 28 (CD28) Dynabeads®, TransAct™ beads, viral peptides, artificial antigen presenting cells (AAPC), Expamer™, or ImmunoCult™ Human CD2/CD3/CD28 T-cell Activators. In Examples, various expansion and culture medias can be used (gas permeable static bags, expandable bags, gas-permeable rapid expansion, Xuri™ Cell Expansion System W25, Xuri™ Cell Expansion System W5, Quantum®). In examples, various formulations (COBE® 2991 Cell Processor, Cell Saver® 5, LOVO Automated Cell Processing System and Sefia), cryopreservation (Mr. Frosty™, VIA Freeze™ Duo, VIA Freeze™ Qyad, Cryomed™, and CoolCell®) and thaw buffers (VIA ThawCB1000, Via ThawSC2, CellSeal® Automated Thawing System, and ThawSTAR® CFTZ Transport and Cell Thawing system) can be used.

Figure 25:
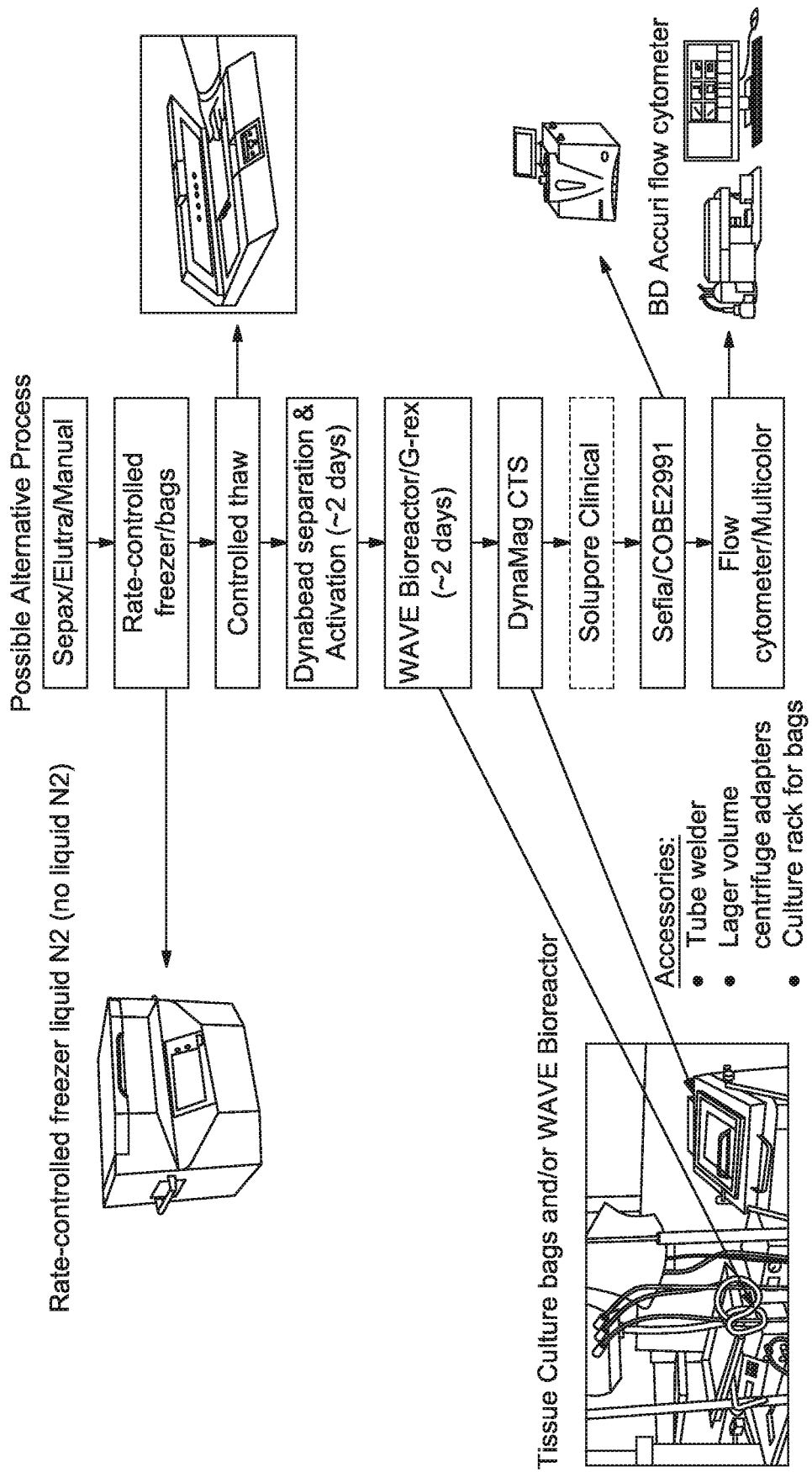
FIG. 25 is a process flow diagram illustrating example cell engineering processing steps.

FIG. 25 is a process flow diagram illustrating example cell engineering processing steps. The example platform can be utilized between DynaMag CTS and Sefia/COBE2991. In examples, the Dynabead separation and activation takes about two days. After activation, the sample can be added to a WAVE Bioreactor/G-rex (Gas Permeable Rapid Expansion) to produce immune cells, and then further processed with DynaMag CTS (ThermoFisher Catalog No. 12102), e.g., for isolation of T cells, Solupore Clinical, the Sefia/COBE2991, and the output can be measured using flow cytometry.

Figure 26:
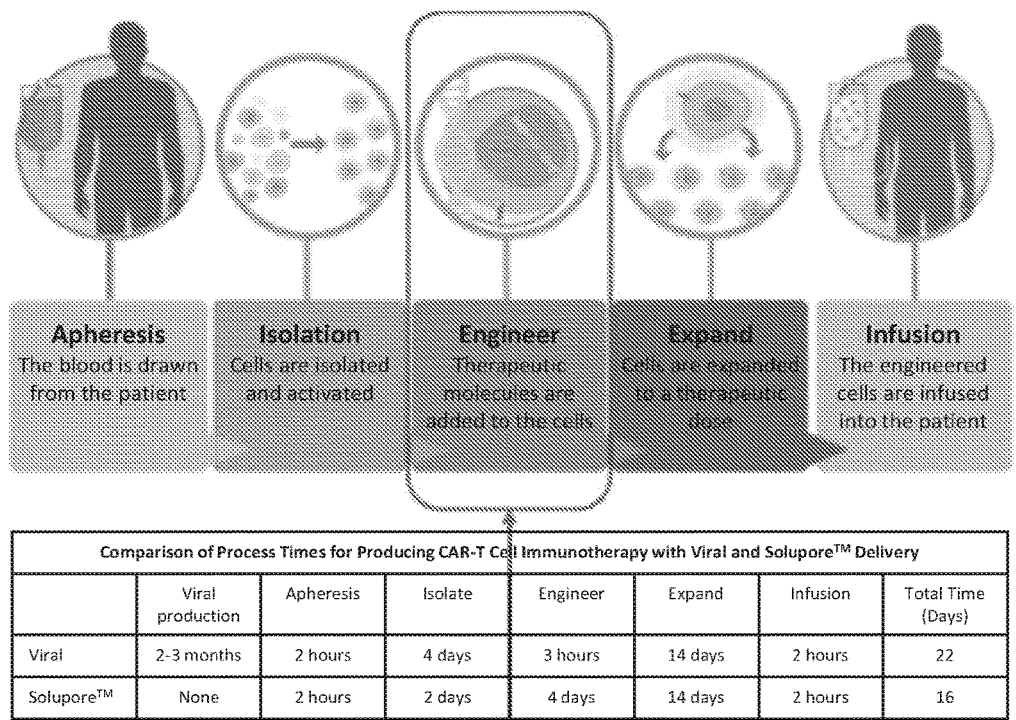
FIG. 26 is a process flow diagram illustrating that the example platform can address cell engineering in the manufacture of adoptive cell therapies.

FIG. 26 is a process flow diagram illustrating that the example platform can address cell engineering in the manufacture of adoptive cell therapies.

Example 3

FIG. 27 is a series of images showing another example bio-reactor design for use with the platform. The example bio-reactor address $2 \times 10^7$ T cells and achieves respectable delivery performance in efficiency, viability, and function. All uptake is achieved in an area bounded by ~30 mm circular diameter. In this configuration, an efficiency greater than about 60% can be achieved in a single spray. In some implementations, the filter may be a polycarbonate track etch (PCTE) filter or a polyester track etch (PETE) filter with about a nominal pore size of 1 µm to 3 µm. The 1 µm to 3 µm filter may be used for the T cell application. In some implementations, the filter may have a nominal pore size of about 5 µm to about 10 µm or larger. The 5 µm to 10 µm filter may be used for the HEK cells, which typically have dimensions in the 11 µm to 15 µm range. The filter material and the filter pore size are not limited thereto, and the filter material and the filter pore size may be selected based on the type of target cells, size of the target cells, concentration of the target cells, or the like.

Figure 28:
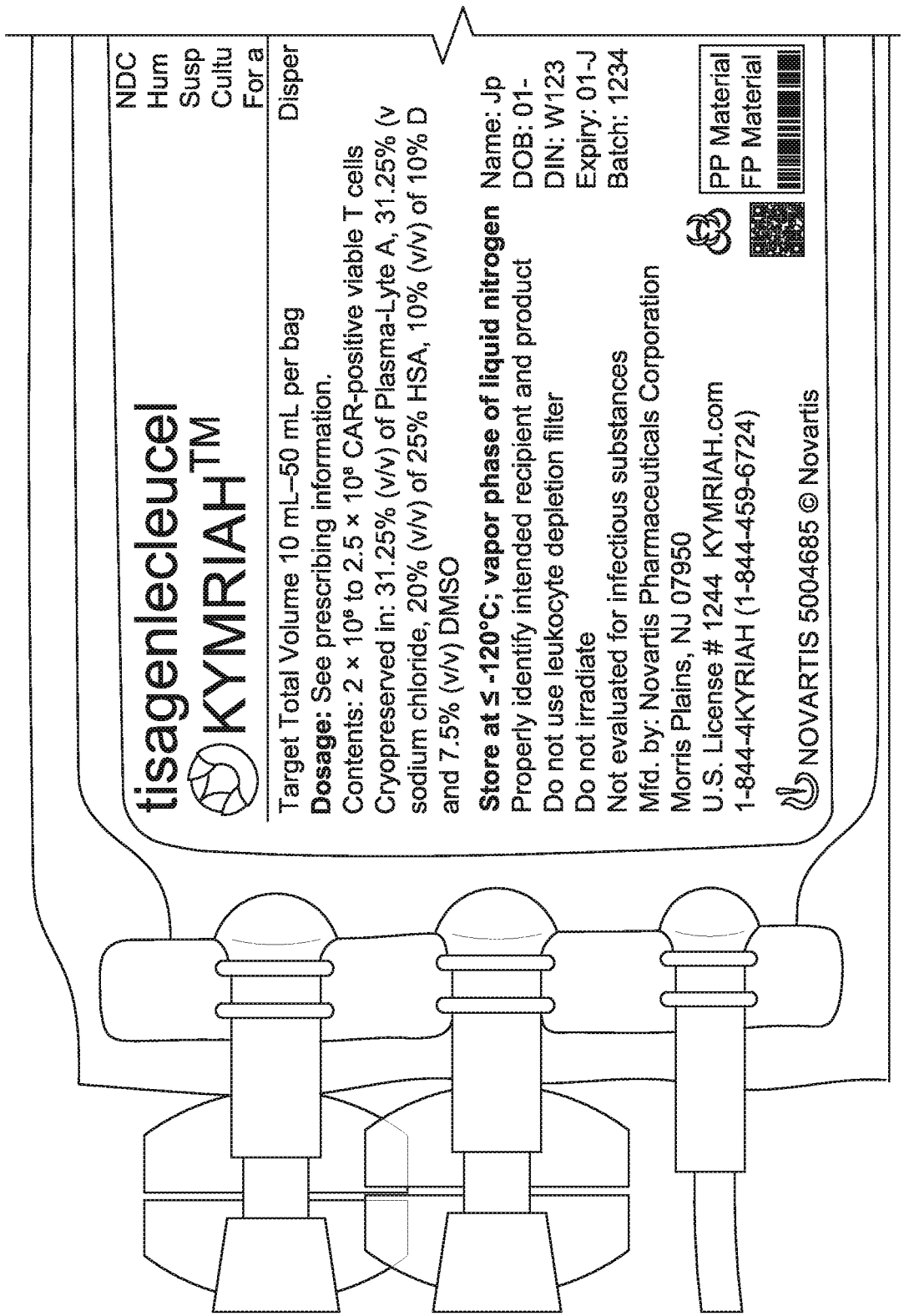
FIG. 28 is an image of Kymriah (tisagenlecleucel), which is approved by the United States Food and Drug Administration (US FDA) for the treatment of pediatric and young adult patients with acute lymphoblastic leukemia (ALL), which uses the body's own T cells to fight cancer.

FIG. 28 is an image of Kymriah (tisagenlecleucel), which is approved by the United States Food and Drug Administration (US FDA) for the treatment of pediatric and young adult patients with acute lymphoblastic leukemia (ALL), which uses the body's own T cells to fight cancer. In examples, the basic unit of scale in cell therapy is a single does, which can vary from $10^6$ to $10^9$ cells. In FIG. 28, the CAR-T (chimeric antigen receptor T cell) therapy Kimriah dose is up to $2.5 \times 10^8$ CAR+ T cells. In other examples, Lonza Nucleofector LV Closed/Sterile system transfects $10^9$ cells in approximately 10 minutes. In examples, the overall process time may be about less than one hour and less than about 20 steps.

Figure 29:
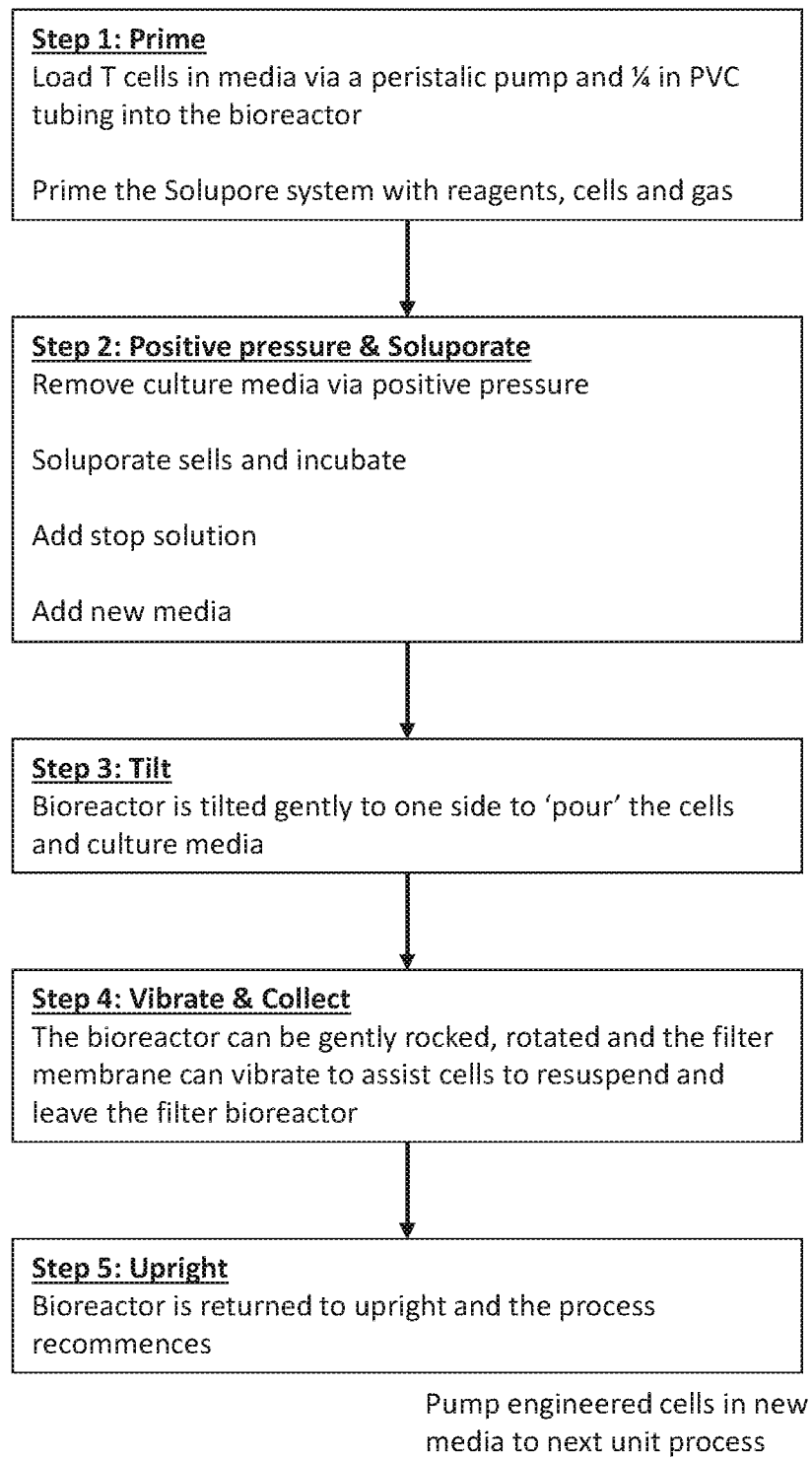
FIG. 29 is a process flow diagram illustrating sub-processes according to some aspects of the current subject matter.

FIG. 29 is a process flow diagram illustrating sub-processes according to some aspects of the current subject matter. At step 1, T cells are loaded into media via a peristaltic pump and ¼ inch PVC tubing into the bioreactor. The system can be primed with reagents, cells, and gas. At step 2, the culture media is removed via positive pressure. The cells are sprayed with the delivery solution, incubated, a stop solution is added, and new media is added. In some implementations, step 2 can be repeated multiple times to improve delivery. At step 3, the bioreactor is tilted gently to one side to 'pour' the cells and culture media. At step 4, the bioreactor can be gently rocked, rotated, and the filter membrane can vibrate to assist cells to re-suspend and leave the filter bioreactor. At step 5, the bioreactor is returned to the upright position and the processing recommences, for example, by returning to step 2 for additional processing, or proceeding to pump engineered cells in new media to next unit process.

Figure 30:
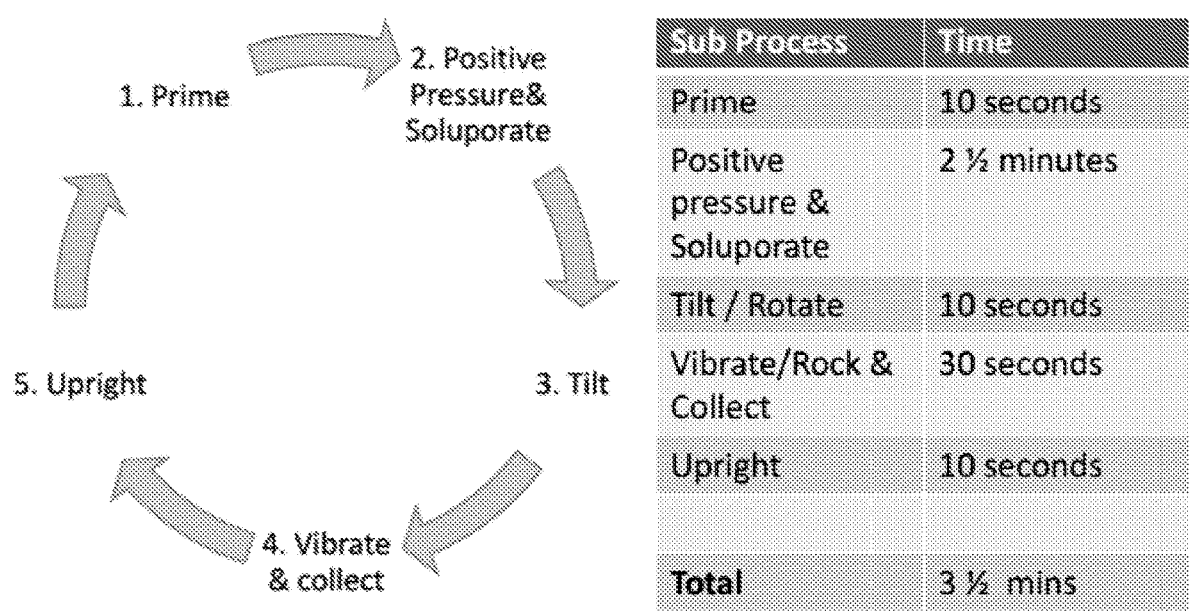
FIG. 30 illustrates an example operational cycle of the example platform, similar to that shown in FIG. 29.

FIG. 30 illustrates an example operational cycle of the example platform, similar to that shown in FIG. 29. Example sub-process execution times are illustrated with a total process time of about 3.5 minutes.

For some example implements, the starting material may include cluster of differentiation 3 (CD3+) T cells or PBMC cells (peripheral blood mononuclear cells). The cells may be activated by various methods, including Dynabeads (e.g., Dynabead CTS (Cell Therapy System) beads), soluble CD3/CD28 (cluster of differentiation 28) antibody, or TransAct for T cell activation. T Cell TransAct is a polymeric nanomatrix conjugated to humanized recombinant CD3 and CD28 agonists ensuring successful activation of resting T cells from hematological cell populations (e.g. PBMCs or enriched T cell populations) without the involvement of CD4 (cluster of differentiation 4) or CD8 (cluster of differentiation 8).

FIG. 31 illustrates a comparison of complexity to isolate and activate 1 million cells. A comparison between peripheral blood mononuclear cells (PBMCs), cluster of differentiation 3 cells (CD3+) and Pan T cells is shown.

FIG. 32 illustrates a comparison of processing options for an exemplary amount of cells, e.g., activation reagent, number of cycles, number of cells, number of cryovials and number of cryobags.

In some embodiments, the system input can include cells, culture media, molecular cargo, stop solution and air and/or gas.

In some embodiments, the cells can include adherent cells or non-adherent cells. The adherent cells can include at least one of primary mesenchymal stem cells, fibroblasts, monocytes, macrophages, lung cells, neuronal cells, fibroblasts, human umbilical vein (HUVEC) cells, Chinese hamster ovary (CHO) cells, and human embryonic kidney (HEK) cells or immortalized cells, such as cell lines. In preferred embodiments, the population of cells comprises non-adherent cells, e.g., the % non-adherent cells in the population is at least 50%, 60%, 75%, 80%, 90%, 95%, 98%, 99% or 100% non-adherent cells. Non-adherent cells primary cells as well as immortalized cells (e.g., cells of a cell line). Exemplary non-adherent/suspension cells include primary hematopoietic stem cell (HSC), T cells (e.g., (cluster of differentiation 3) CD3+ cells, (cluster of differentiation 4) CD4+ cells, (cluster of differentiation 8) CD8+ cells), natural killer (NK) cells, cytokine-induced killer (CIK) cells, human cord blood CD34+ cells, B cells, or cell lines such as Jurkat T cell line. Non limiting examples of T cells may include CD8+ or CD4+ T cells. In some aspects, the CD8+ subpopulation of the $CD3^+$ T cells are used. $CD8^+$ T cells may be purified from the PBMC population by positive isolation using anti-CD8 beads.

In examples, cells are cultured in standard cell culture media, e.g., complete RPMI (Roswell Park Memorial Institute medium) using RPMI basal medium, heat-inactivated fetal bovine serum (FBS), e.g., about 10% v/v, penicillin-streptomycin, and L-glutamine. In some examples, the standard culture media can be supplemented with cytokines, e.g., Interleukin-2 (IL-2) (200 U/ml).

In embodiments, the cytokines can be at a concentration from about 10 U/ml to about 500 U/ml. In other examples, the cytokines can be at a concentration of about 50 U/ml, about 100 U/ml, about 200 U/ml, about 300 U/ml, about 400 U/ml, or about 500 U/ml. The cytokine concentration can be about 200 U/ml.

In some examples, cell-compatible culture media are used in the delivery methods. For example, Prime-XV (Irvine Scientific) and X-Vivo (Lonza) are serum-free and animal component free media that can be used.). In some examples, the cell culture media was supplemented with a higher concentration of cytokines. The cytokines can include, for example, interleukin-2 (IL-2), to enhance the rate of proliferation (Tumeh P, et al., *J Immunother* 2010. 33 (6): 759-768 and Besser M J, et al., *Cytotherapy* 2009. 11:206-217). In other examples, the culture medium can include Immunocult™-XF Expansion Medium (StemCell Technologies). Like Prime XV, it is also a serum-free, xeno-free T cell culture medium. In some examples, TexMACS (Miltenyi Biotech) may be used as an alternative serum-free medium for T-cell culture.

In embodiments, the molecular cargo (e.g., payload) can include gene editing tools, a small chemical molecule, a peptide or protein, or a nucleic acid. The payload can comprise a messenger ribonucleic acid (mRNA). The mRNA can encode a gene-editing composition. The mRNA can encode a chimeric antigen receptor.

In additional embodiments, the molecular cargo (e.g., payload) to be delivered may include a composition that edits genomic DNA (i.e., gene editing tools). For example, the gene editing composition may include a compound or complex that cleaves, nicks, splices, rearranges, translocates, recombines, or otherwise alters genomic DNA. Alternatively or in addition, a gene editing composition may include a compound that (i) may be included a gene-editing complex that cleaves, nicks, splices, rearranges, translocates, recombines, or otherwise alters genomic DNA; or (ii) may be processed or altered to be a compound that is included in a gene-editing complex that cleaves, nicks, splices, rearranges, translocates, recombines, or otherwise alters genomic DNA. In various embodiments, the gene editing composition comprises one or more of (a) gene editing protein; (b) RNA molecule; and/or (c) ribonucleoprotein (RNP).

In some embodiments, the gene editing composition comprises a gene editing protein, and the gene editing protein is a zinc finger nuclease (ZFN), a transcription activator-like effector nuclease (TALEN), a Cas protein, a Cre recombinase, a Hin recombinase, or a Flp recombinase. In additional embodiments, the gene editing protein may be a fusion proteins that combine homing endonucleases with the modular DNA binding domains of TALENs (megaTAL). For example, megaTAL may be delivered as a protein or alternatively, a mRNA encoding a megaTAL protein is delivered to the cells.

In embodiments, the molecular cargo (e.g., payload) can include a small chemical molecule. The small chemical molecule can be less than 1,000 Da. The chemical molecule can include MitoTracker® Red CMXRos, propidium iodide, methotrexate, and/or DAPI (4',6-diamidino-2-phenylindole).

In embodiments, the molecular cargo can be a peptide. The peptide can be about 5,000 Da. The peptide can include ecallantide under trade name Kalbitor, is a 60 amino acid polypeptide for the treatment of hereditary angioedema and in prevention of blood loss in cardiothoracic surgery), Liraglutide (marketed as the brand name Victoza, is used for the treatment of type II diabetes, and Saxenda for the treatment of obesity), and Icatibant (trade name Firazyer, a peptidomimetic for the treatment of acute attacks of hereditary angioedema). The small-interfering ribonucleic acid (siRNA) molecule can be about 20-25 base pairs in length, or can be about 10,000-15,000 Da. The siRNA molecule can reduces the expression of any gene product, e.g., knockdown of gene expression of clinically relevant target genes or of model genes, e.g., glyceraldehyde-3phosphate dehydrogenase (GAPDH) siRNA, GAPDH siRNA-FITC, cyclophilin B siRNA, and/or lamin siRNA. Protein therapeutics can include peptides, enzymes, structural proteins, receptors, cellular proteins, or circulating proteins, or fragments thereof. The protein or polypeptide be about 100-500,000 Da, e.g., 1,000-150,000 Da. The protein can include any therapeutic, diagnostic, or research protein or peptide, e.g., beta-lactoglobulin, ovalbumin, bovine serum albumin (BSA), and/or horseradish peroxidase. In other examples, the protein can include a cancer-specific apoptotic protein, e.g., Tumor necrosis factor-related apoptosis inducing protein (TRAIL).

An antibody is generally be about 150,000 Da in molecular mass. The antibody can include an anti-actin antibody, an anti-GAPDH antibody, an anti-Src antibody, an anti-Myc ab, and/or an anti-Raf antibody. The antibody can include a green fluorescent protein (GFP) plasmid, and a GLuc plasmid. The DNA molecule can be greater than 5,000,000 Da. In some examples, the antibody can be a murine-derived monoclonal antibody, e.g., ibritumomab tiuxetin, muromomab-CD3, tositumomab, a human antibody, or a humanized mouse (or other species of origin) antibody. In other examples, the antibody can be a chimeric monoclonal antibody, e.g., abciximab, basiliximab, cetuximab, infliximab, or rituximab. In still other examples, the antibody can be a humanized monoclonal antibody, e.g., alemtuzamab, bevacizumab, certolizumab pegol, daclizumab, gentuzumab ozogamicin, trastuzumab, tocilizumab, ipilimumamb, or panitumumab. The antibody can comprise an antibody fragment, e.g., abatecept, aflibercept, alefacept, or etanercept. The invention encompasses not only an intact monoclonal antibody, but also an immunologically-active antibody fragment, e.g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

The molecular cargo (e.g., payload) can include a therapeutic agent. A therapeutic agent, e.g., a drug, or an active agent", can mean any compound useful for therapeutic or diagnostic purposes, the term can be understood to mean any compound that is administered to a patient for the treatment of a condition. Accordingly, a therapeutic agent can include, proteins, peptides, antibodies, antibody fragments, and small molecules. Therapeutic agents described in U.S. Pat. No. 7,667,004 "Humanized antibodies against vascular endothelial growth factor" (incorporated herein by reference) can be used in the methods described herein. The therapeutic agent can include at least one of cisplatin, aspirin, statins (e.g., pitavastatin, atorvastatin, lovastatin, pravastatin, rosuvastatin, simvastatin, promazine hydrochloric acid (HCl), chloropromazine HCl, thioridazine HCl, Polymyxin B sulfate, chloroxine, benfluorex HCl and phenazopyridine HCl), and fluoxetine. The payload can include a diagnostic agent. The diagnostic agent can include a detectable label or marker such as at least one of methylene blue, patent blue V, and indocyanine green. The payload can include a fluorescent molecule. The payload can include a detectable nanoparticle. The nanoparticle can include a quantum dot.

In an example, following delivery, the cells are incubated prior to the addition of Stop Solution. In examples, the Stop Solution includes phosphate buffered saline (PBS). The concentration of PBS can be about 0.5×PBS.

Figure 33:
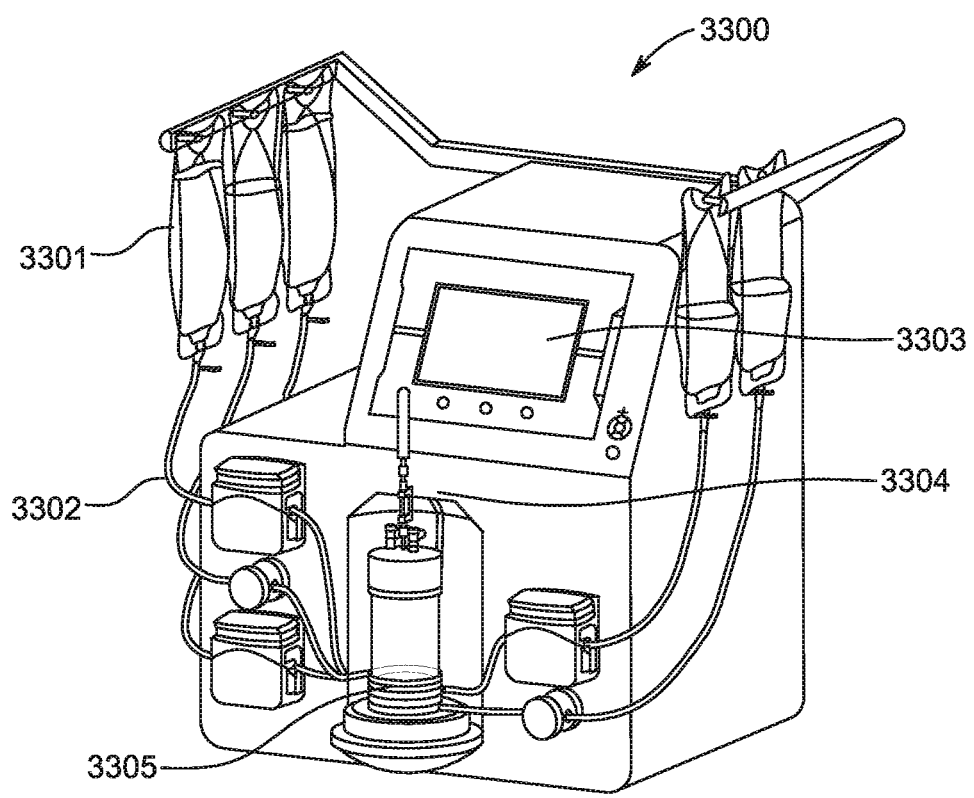
FIG. 33 illustrates another example platform according to the current subject matter.

FIG. 33 illustrates another example platform according to the current subject matter. A closed system 3300 can include bags or reservoirs 3301, pumps 3302, an interface screen 3303, cargo introduction module 3304, and the tilting bioreactor 3305.

Figure 34:
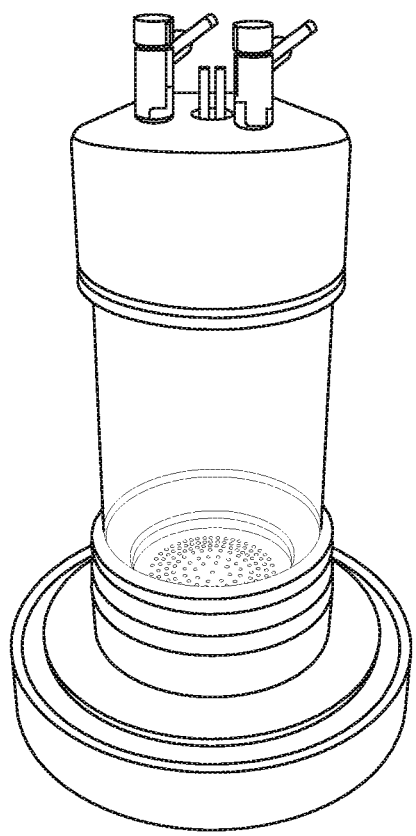
FIG. 34 is a CAD drawing illustrating an example disposable bioreactor.

FIG. 34 is a CAD drawing illustrating an example disposable bioreactor. The bioreactor can tilt up to 15 degrees away from normal, can rotate while titling, can rock and can contain vibrational elements to vibrate the filter membrane. Cargo can be introduced via an SMA01. An SMA01 is a nebulizer, and in embodiments, may include any nebulizer. In embodiments, the values at which the nebulizer is used involves the atomization of a volume between about 10-300 µl of cell permeabilizing solution. Exemplary nebulizers are described in U.S. Pat. No. 5,411,208 or U.S. Pat. No. 6,634,572, hereby incorporated by reference in their entireties. Additional nebulizers are commercially available, e.g., from DuraMist™ Nebulizer (Sigma-Aldrich GXARG1DM04-1EA), Nebulizer, OneNeb, series 2 inert concentric type nebulizer, or use with ICP-OES (Agilent Technologies G8010-60293). In embodiments, the nebulizer can be an ultrasonic nebulizer, or a vibrating mesh nebulizer. Input and output tubes can be welded or Hospira Spinning Spires closed connectors can be utilized.

FIG. 35 illustrates the filter plate vessel with stop solution added. The stop solution can be added through a series of holes (illustrated) in the circumference of the filter plate vessel. The internal manifold of the vessel is designed to ensure equal flow from each orifice.

FIG. 36 illustrates the filter plate vessel with new media added. Post incubation, cell culture media can be added through a second set of circumferential holes. Media addition can occur in second (for mL volumes).

FIG. 37 illustrates the bioreactor tilting during operation. The entire bioreactor is illustrated left, and the filter plate vessel is illustrated right. The system is a closed system. The bioreactor can tilt up to 15 degrees away from normal (the bioreactor including the filter plate vessel). The bioreactor can rotate while tilting. The bioreactor can rock and contains vibrational elements to vibrate the filter membrane.

Figure 38:
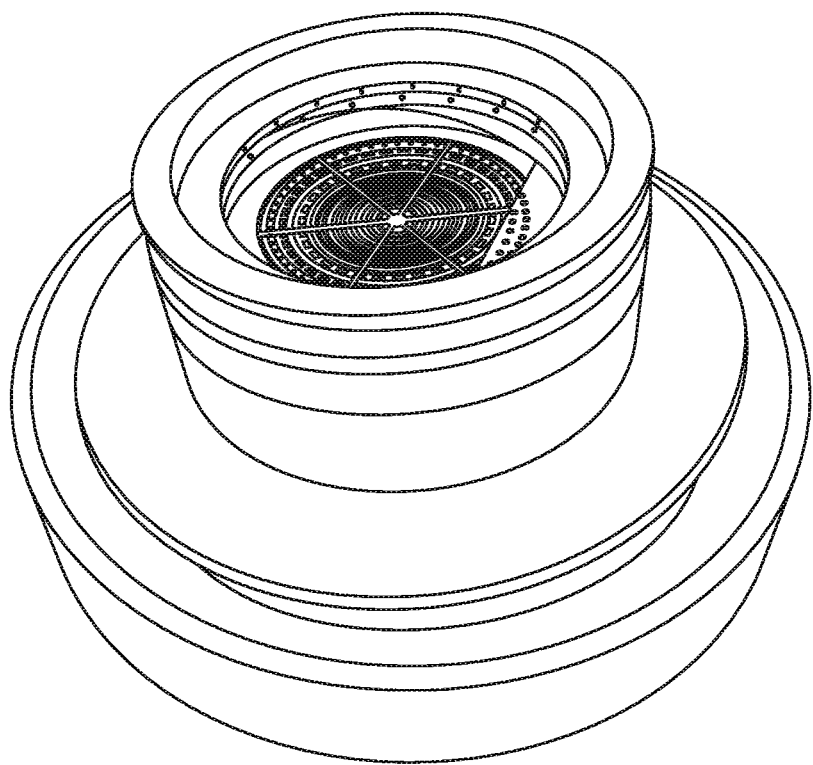
FIG. 38 illustrates the filter plate vessel during cell culture media "pour off" in which the vessel (e.g., reactor) tilts, rotates and vibrates to facilitate removal of cells in media.

FIG. 38 illustrates the filter plate vessel during cell culture media "pour off" in which the vessel (e.g., reactor) tilts, rotates and vibrates to facilitate removal of cells in media. The filter plate vessel can tilt when containing cell culture media with cells in suspension to pour off the membrane surface with the help of tilting, rotating, and vibrating as necessary. For example, this approach can remove cell "cakes" from the filter. Different vibrational patterns and excursions are possible.

The current subject matter can include a number of components including, for example, accelerated product introduction, acoustics, additive manufacturing, adhesive, advanced assembly, automation, device integration, digital prototyping, dynamic tuning, fluidics, human machine interface, optical communications, optics, power electronics, precision injection mold tooling, precision mechanics, printed electronics, sensors, software application design, wireless connectivity, and documentation.

Figure 39:
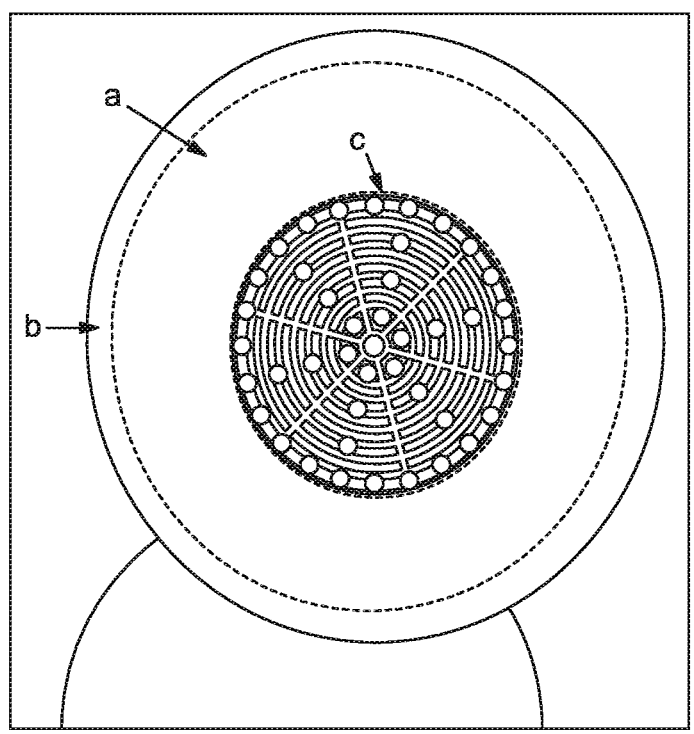
FIG. 39 illustrates an example membrane holder.

FIG. 39 is an example membrane holder. The example membrane holder can be implanted for use with the first example platform (described with reference to FIGS. 16-26) or the second example platform (described with reference to FIGS. 27-38). When forming a monolayer using positive pressure on a filter plate, it can be challenging to control the cell deposition pattern on the filter membrane. The configuration of ridges and holes in the filter plate affects the deposition pattern of suspension cells on a filter membrane. Cells deposit on the filter, but only where the ridges and holes are located on the underlying membrane holder (e.g., acting as a stencil). Where the cells deposit and pattern of deposition within that area can be controlled by the membrane holder design. Further, discrete cell monolayers can be created over a continuous filter membrane using a membrane holder that contains discrete filtration areas which act like drains.

As illustrated in FIG. 39, the membrane hold includes a single filtration area. In the example, a 44-mm polycarbonate track etch (PCTE) filter membrane (denoted 'a' and shown with outer dashed circle) is placed onto the membrane holder (b). The membrane holder has ridges and holes located within a central 25 mm diameter (c). In order to illustrate the effect of the example design, the membrane holder was inserted into the base of an Amicon Stirred cell pressure filtration unit (not shown here). A suspension of Dynabeads was added to the chamber and positive pressure applied. Dynabeads (which were used as a model for T cells) only deposited where the ridges and holes are located (denoted by inner dashed circle).

Figure 40:
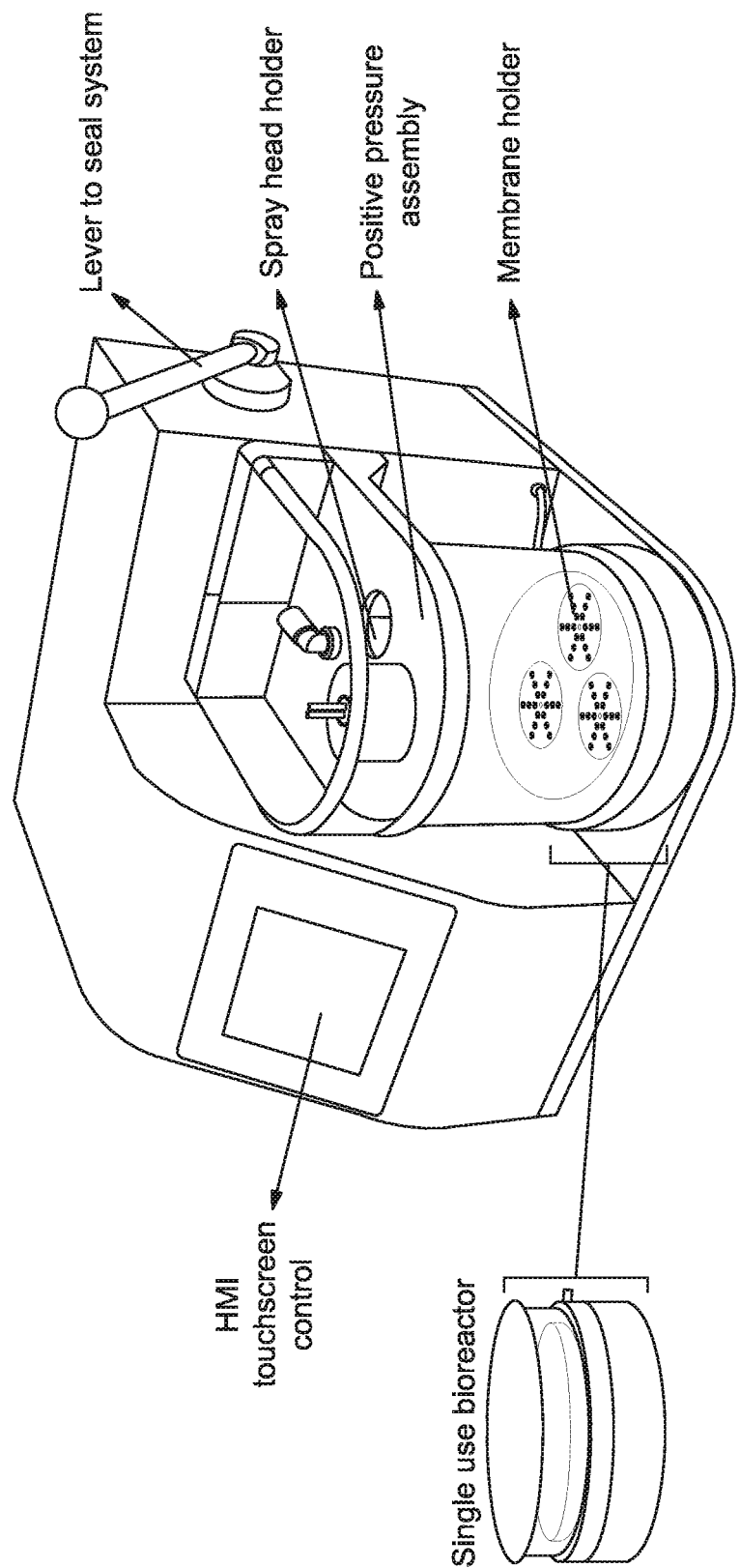
FIG. 40 illustrates an exemplary system. This is an intermediate system which can address up to $5 \times 10^7$ cells. This system has the same features as the Clinical (full scale, $1 \times 10^9$ cells and more cells) system, but does not include a translational spray head mechanism. Instead, the system utilizes a single head or a multiple head array.

FIG. 40 illustrates an example of an intermediate system which address up to $5 \times 10^7$ cells. This system has the same features as the clinical system (full scale, e.g., greater than $5 \times 10^7$ cells, e.g., $1 \times 10^8$, as well as $10^9$ cells or more per processing run), but the system does not include a translational spray head mechanism, and instead utilizes a single head or a multiple head array.

Although a few variations have been described in detail above, other modifications or additions are possible. For example, design variations can include filter substrates of other geometries, e.g., rectangular, square or elliptical. Additionally, filter substrates, with varying topography, can include convex, concave and textured surfaces with micro or macro features. Also, target configurations including both circular targets and annular targets are contemplated. In embodiments, the modifications or additions can optimize cell deposition under the spray target.

The subject matter described herein provides many technical advantages. For example, single use avoids the need for sterilization of the system and greatly reduces the risk of cross contamination between patient samples, and enabling a simpler validation process. Also, single use enables temperature and humidity control within the bioreactor producing a healthier cell population. Another advantage is that it enables the delivery of multiple cargos through co-delivery through a single spray head or the ability to have multiple spray heads installed. Furthermore, the subject matter described herein is fast and simple, and the gentle cell processing maintains cell health and enables engineering of naïve cell populations. Temperature control of the filter substrate also enables better control of the delivery process and aid in recovery of cells from the system. The combination of the membrane holder design and nebulizer parameters enables optimization of the system for delivery of different cargos to different cell types.

Example Delivery Protocol

The invention is based on the surprising discovery that compounds or mixtures of compounds (compositions) are delivered into the cytoplasm of eukaryotic cells by contacting the cells with a solution containing a compound(s) to be delivered (e.g., payload) and an agent that reversibly permeates or dissolves a cell membrane. Preferably, the solution is delivered to the cells in the form of a spray, e.g., aqueous particles. (see, e.g., PCT/US2015/057247 and PCT/IB2016/001895, hereby incorporated in their entirety by reference). For example, the cells are coated with the spray but not soaked or submersed in the delivery compound-containing solution. Exemplary agents that permeate or dissolve a eukaryotic cell membrane include alcohols and detergents such as ethanol and Triton X-100, respectively. Other exemplary detergents, e.g., surfactants include polysorbate 20 (e.g., Tween 20), 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), sodium dodecyl sulfate (SDS), and octyl glucoside.

An example of conditions to achieve a coating of a population of coated cells include delivery of a fine particle spray, e.g., the conditions exclude dropping or pipetting a bolus volume of solution on the cells such that a substantial population of the cells are soaked or submerged by the volume of fluid. Thus, the mist or spray comprises a ratio of volume of fluid to cell volume. Alternatively, the conditions comprise a ratio of volume of mist or spray to exposed cell area, e.g., area of cell membrane that is exposed when the cells exist as a confluent or substantially confluent layer on a substantially flat surface such as the bottom of a tissue culture vessel, e.g., a well of a tissue culture plate, e.g., a microtiter tissue culture plate.

"Cargo" or "payload" are terms used to describe a compound, or composition that is delivered via an aqueous solution across a cell plasma membrane and into the interior of a cell.

In an aspect, delivering a payload across a plasma membrane of a cell includes providing a population of cells and contacting the population of cells with a volume of an aqueous solution. The aqueous solution includes the payload and an alcohol content greater than 2 percent concentration. The volume of the aqueous solution may be a function of exposed surface area of the population of cells, or may be a function of a number of cells in the population of cells.

In another aspect, a composition for delivering a payload across a plasma membrane of a cell includes an aqueous solution including the payload, an alcohol at greater than 2 percent concentration, greater than 46 mM salt, less than 121 mM sugar, and less than 19 mM buffering agent. For example, the alcohol, e.g., ethanol, concentration does not exceed 50%.

One or more of the following features can be included in any feasible combination. The volume of solution to be delivered to the cells is a plurality of units, e.g., a spray, e.g., a plurality of droplets on aqueous particles. The volume is described relative to an individual cell or relative to the exposed surface area of a confluent or substantially confluent (e.g., at least 75%, at least 80% confluent, e.g., 85%, 90%, 95%, 97%, 98%, 100%) cell population. For example, the volume can be between $6.0\times10^{-7}$ microliter per cell and $7.4\times10^{-4}$ microliter per cell. The volume is between $4.9\times10^{-6}$ microliter per cell and $2.2\times10^{-3}$ microliter per cell. The volume can be between $9.3\times10^{-6}$ microliter per cell and $2.8\times10^{-5}$ microliter per cell. The volume can be about $1.9\times10^{-5}$ microliters per cell, and about is within 10 percent. The volume is between $6.0\times10^{-7}$ microliter per cell and $2.2\times10^{-3}$ microliter per cell. The volume can be between $2.6\times10^{-9}$ microliter per square micrometer of exposed surface area and $1.1\times10^{-6}$ microliter per square micrometer of exposed surface area. The volume can be between $5.3\times10^{-8}$ microliter per square micrometer of exposed surface area and $1.6\times10^{-7}$ microliter per square micrometer of exposed surface area. The volume can be about $1.1\times10^{-7}$ microliter per square micrometer of exposed surface area. About can be within 10 percent.

Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel.

Contacting the population of cells with the volume of aqueous solution can be performed by gas propelling the aqueous solution to form a spray. The gas can include nitrogen, ambient air, or an inert gas. The spray can include discrete units of volume ranging in size from, 1 nm to 100 µm, e.g., 30-100 µm in diameter. The spray includes discrete units of volume with a diameter of about 30-50 µm. In some implementations, the spray includes discrete units of volume with a diameter of about 5-8 µm. A total volume of aqueous solution of 20 µl can be delivered in a spray to a cell-occupied area of about 1.9 cm$^2$, e.g., one well of a 24-well culture plate. A total volume of aqueous solution of 10 µl is delivered to a cell-occupied area of about 0.95 cm$^2$, e.g., one well of a 48-well culture plate. Typically, the aqueous solution includes a payload to be delivered across a cell membrane and into cell, and the second volume is a buffer or culture medium that does not contain the payload. Alternatively, the second volume (buffer or media) can also contain payload. In some embodiments, the aqueous solution includes a payload and an alcohol, and the second volume does not contain alcohol (and optionally does not contain payload). The population of cells can be in contact with said aqueous solution for 0.1 10 minutes prior to adding a second volume of buffer or culture medium to submerse or suspend said population of cells. The buffer or culture medium can be phosphate buffered saline (PBS). The population of cells can be in contact with the aqueous solution for 2 seconds to 5 minutes prior to adding a second volume of buffer or culture medium to submerse or suspend the population of cells. The population of cells can be in contact with the aqueous solution, e.g., containing the payload, for 30 seconds to 2 minutes prior to adding a second volume of buffer or culture medium, e.g., without the payload, to submerse or suspend the population of cells. The population of cells can be in contact with a spray for about 1-2 minutes prior to adding the second volume of buffer or culture medium to submerse or suspend the population of cells. During the time between spraying of cells and addition of buffer or culture medium, the cells remain hydrated by the layer of moisture from the spray volume.

The aqueous solution can include an ethanol concentration of 5 to 30%. The aqueous solution can include one or more of 75 to 98% H$_2$O, 2 to 45% ethanol, 6 to 91 mM sucrose, 2 to 500 mM KCl, 2 to 35 mM ammonium acetate, and 1 to 14 mM (4-(2-hydroxyethyl)-1-piperazineethanesulfonic acid) (HEPES). For example, the delivery solution contains 106 mM KCl and 25% ethanol.

The population of cells can include adherent cells or non-adherent cells. The adherent cells can include at least one of primary mesenchymal stem cells, fibroblasts, monocytes, macrophages, lung cells, neuronal cells, fibroblasts, human umbilical vein (HUVEC) cells, Chinese hamster ovary (CHO) cells, and human embryonic kidney (HEK) cells or immortalized cells, such as cell lines. The population of cells can also include cells that are adherent in a suspension culture. The cells that are adherent in a suspension culture can include human embryonic kidney (HEK) cells or macrophages. In preferred embodiments, the population of cells comprises non-adherent cells, e.g., the % non-adherent cells in the population is at least 50%, 60%, 75%, 80%, 90%, 95%, 98%, 99% or 100% non-adherent cells. Non-adherent cells primary cells as well as immortalized cells (e.g., cells of a cell line). Exemplary non-adherent/suspension cells include primary hematopoietic stem cell (HSC), T cells (e.g., CD3+ cells, CD4+ cells, CD8+ cells), natural killer (NK) cells, cytokine-induced killer (CIK) cells, human cord blood CD34+ cells, B cells, or cell lines such as Jurkat T cell line.

The payload can include a small chemical molecule, a peptide or protein, or a nucleic acid. The small chemical molecule can be less than 1,000 Da. The chemical molecule can include MitoTracker® Red CMXRos, propidium iodide, methotrexate, and/or DAPI (4',6-diamidino-2-phenylindole). The peptide can be about 5,000 Da. The peptide can include ecallantide under trade name Kalbitor, is a 60 amino acid polypeptide for the treatment of hereditary angioedema and in prevention of blood loss in cardiothoracic surgery), Liraglutide (marketed as the brand name Victoza, is used for the treatment of type II diabetes, and Saxenda for the treatment of obesity), and Icatibant (trade name Firazyer, a peptidomimetic for the treatment of acute attacks of hereditary angioedema). The small-interfering ribonucleic acid (siRNA) molecule can be about 20-25 base pairs in length, or can be about 10,000-15,000 Da. The siRNA molecule can reduces the expression of any gene product, e.g., knockdown of gene expression of clinically relevant target genes or of model genes, e.g., glyceraldehyde-3phosphate dehydrogenase (GAPDH) siRNA, GAPDH siRNA-FITC, cyclophilin B siRNA, and/or lamin siRNA. Protein therapeutics can include peptides, enzymes, structural proteins, receptors, cellular proteins, or circulating proteins, or fragments thereof. The protein or polypeptide be about 100-500,000 Da, e.g., 1,000-150,000 Da. The protein can include any therapeutic, diagnostic, or research protein or peptide, e.g., beta-lactoglobulin, ovalbumin, bovine serum albumin (BSA), and/or horseradish peroxidase. In other examples, the protein can include a cancer-specific apoptotic protein, e.g., Tumor necrosis factor-related apoptosis inducing protein (TRAIL).

An antibody is generally be about 150,000 Da in molecular mass. The antibody can include an anti-actin antibody, an anti-GAPDH antibody, an anti-Src antibody, an anti-Myc ab, and/or an anti-Raf antibody. The antibody can include a green fluorescent protein (GFP) plasmid, a GLuc plasmid and, and a BATEM plasmid. The DNA molecule can be greater than 5,000,000 Da. In some examples, the antibody can be a murine-derived monoclonal antibody, e.g., ibritumomab tiuxetin, muromomab-CD3, tositumomab, a human antibody, or a humanized mouse (or other species of origin) antibody. In other examples, the antibody can be a chimeric monoclonal antibody, e.g., abciximab, basiliximab, cetuximab, infliximab, or rituximab. In still other examples, the antibody can be a humanized monoclonal antibody, e.g., alemtuzamab, bevacizumab, certolizumab pegol, daclizumab, gentuzumab ozogamicin, trastuzumab, tocilizumab, ipilimumamb, or panitumumab. The antibody can comprise an antibody fragment, e.g., abatecept, aflibercept, alefacept, or etanercept. The invention encompasses not only an intact monoclonal antibody, but also an immunologically-active antibody fragment, e.g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

The payload can include a therapeutic agent. A therapeutic agent, e.g., a drug, or an active agent", can mean any compound useful for therapeutic or diagnostic purposes, the term can be understood to mean any compound that is administered to a patient for the treatment of a condition. Accordingly, a therapeutic agent can include, proteins, peptides, antibodies, antibody fragments, and small molecules. Therapeutic agents described in U.S. Pat. No. 7,667,004 (incorporated herein by reference) can be used in the methods described herein. The therapeutic agent can include at least one of cisplatin, aspirin, statins (e.g., pitavastatin, atorvastatin, lovastatin, pravastatin, rosuvastatin, simvastatin, promazine HCl, chloropromazine HCl, thioridazine HCl, Polymyxin B sulfate, chloroxine, benfluorex HCl and phenazopyridine HCl), and fluoxetine. The payload can include a diagnostic agent. The diagnostic agent can include a detectable label or marker such as at least one of methylene blue, patent blue V, and indocyanine green. The payload can include a fluorescent molecule. The payload can include a detectable nanoparticle. The nanoparticle can include a quantum dot.

The population of non-adherent cells can be substantially confluent, such as greater than 75 percent confluent. Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel. The population of cells can form a monolayer of cells.

The alcohol can be selected from methanol, ethanol, isopropyl alcohol, butanol and benzyl alcohol. The salt can be selected from NaCl, KCl, $Na_2HPO_4$, $KH_2PO_4$, and $C_2H_3O_2NH$. In preferred embodiments, the salt is KCl. The sugar can include sucrose. The buffering agent can include 4-2-(hydroxyethyl)-1-piperazineethanesulfonic acid.

The present subject matter relates to a method for delivering molecules across a plasma membrane. The present subject matter finds utility in the field of intra-cellular delivery, and has application in, for example, delivery of molecular biological and pharmacological therapeutic agents to a target site, such as a cell, tissue, or organ. The method of the present subject matter comprises introducing the molecule to an aqueous composition to form a matrix; atomizing the matrix into a spray; and contacting the matrix with a plasma membrane.

This present subject matter relates to a composition for use in delivering molecules across a plasma membrane. The present subject matter finds utility in the field of intra-cellular delivery, and has application in, for example, delivery of molecular biological and pharmacological therapeutic agents to a target site, such as a cell, tissue, or organ. The composition of the present subject matter comprises an alcohol; a salt; a sugar; and/or a buffering agent.

In some implementations, demonstrated is a permeabilisation technique that facilitates intracellular delivery of molecules independent of the molecule and cell type. Nanoparticles, small molecules, nucleic acids, proteins and other molecules can be efficiently delivered into suspension cells or adherent cells in situ, including primary cells and stem cells, with low cell toxicity and the technique is compatible with high throughput and automated cell-based assays.

The example methods described herein include a payload, wherein the payload includes an alcohol. By the term "an alcohol" is meant a polyatomic organic compound including a hydroxyl (—OH) functional group attached to at least one carbon atom. The alcohol may be a monohydric alcohol and may include at least one carbon atom, for example methanol. The alcohol may include at least two carbon atoms (e.g. ethanol). In other aspects, the alcohol comprises at least three carbons (e.g. isopropyl alcohol). The alcohol may include at least four carbon atoms (e.g., butanol), or at least seven carbon atoms (e.g., benzyl alcohol). The example payload may include no more than 50% (v/v) of the alcohol, more preferably, the payload comprises 2-45% (v/v) of the alcohol, 5-40% of the alcohol, and 10-40% of the alcohol. The payload may include 20-30% (v/v) of the alcohol.

Most preferably, the payload delivery solution includes 25% (v/v) of the alcohol. Alternatively, the payload can include 2-8% (v/v) of the alcohol, or 2% of the alcohol. The alcohol may include ethanol and the payload comprises 5, 10, 20, 25, 30, and up to 40% or 50% (v/v) of ethanol, e.g., 27%. Example methods may include methanol as the alcohol, and the payload may include 5, 10, 20, 25, 30, or 40% (v/v) of the methanol. The payload may include 2-45% (v/v) of methanol, 20-30% (v/v), or 25% (v/v) methanol. Preferably, the payload includes 20-30% (v/v) of methanol. Further alternatively, the alcohol is butanol and the payload comprises 2, 4, or 8% (v/v) of the butanol.

In some aspects of the present subject matter, the payload is in a solution or buffer.

According to the present subject matter, the payload may include at least one salt. The salt may be selected from NaCl, KCl, $Na_2HPO_4$, $C_2H_3O_2NH_4$ and $KH_2PO_4$. For example, KCl concentration ranges from 2 mM to 500 mM. In some preferred embodiments, the concentration is greater than 100 mM, e.g., 106 mM.

According to example methods of the present subject matter, the payload may include a sugar (e.g., a sucrose, or a disaccharide). According to example methods, the payload comprises less than 121 mM sugar, 6-91 mM, or 26-39 mM sugar. Still further, the payload includes 32 mM sugar (e.g., sucrose). Optionally, the sugar is sucrose and the payload comprises 6.4, 12.8, 19.2, 25.6, 32, 64, 76.8, or 89.6 mM sucrose.

According to example methods of the present subject matter, the payload may include a buffering agent (e.g. a weak acid or a weak base). The buffering agent may include a zwitterion. According to example methods, the buffering agent is 4-(2-hydroxyethyl)-1-piperazineethanesulfonic acid. The payload may comprise less than 19 mM buffering agent (e.g., 1-15 mM, or 4-6 mM or 5 mM buffering agent). According to example methods, the buffering agent is 4-(2-hydroxyethyl)-1-piperazineethanesulfonic acid and the payload comprises 1, 2, 3, 4, 5, 10, 12, 14 mM 4-(2-hydroxyethyl)-1-piperazineethanesulfonic acid. Further preferably, the payload comprises 5 mM 4-(2-hydroxyethyl)-1-piperazineethanesulfonic acid.

According to example methods of the present subject matter, the payload includes ammonium acetate. The payload may include less than 46 mM ammonium acetate (e.g., between 2-35 mM, 10-15 mM, or 25 mM ammonium acetate). The payload may include 2.4, 4.8, 7.2, 9.6, 12, 24, 28.8, or 33.6 mM ammonium acetate.

The volume of aqueous solution performed by gas propelling the aqueous solution may include compressed air (e.g. ambient air), other implementations may include inert gases, for example, helium, neon, and argon.

In certain aspects of the present subject matter, the population of cells may include adherent cells (e.g., lung, kidney, immune cells such as macrophages) or non-adherent cells (e.g., suspension cells).

In certain aspects of the present subject matter, the population of cells may be substantially confluent, and substantially may include greater than 75 percent confluent. In preferred implementations, the population of cells may form a single monolayer.

According to example methods, the payload to be delivered has an average molecular weight of up to 20,000,000 Da. In some examples, the payload to be delivered can have an average molecular weight of up to 2,000,000 Da. In some implementations, the payload to be delivered may have an average molecular weight of up to 150,000 Da. In further implementations, the payload to be delivered has an average molecular weight of up to 15,000 Da, 5,000 Da or 1,000 Da.

The payload to be delivered across the plasma membrane of a cell may include a small chemical molecule, a peptide or protein, a polysaccharide or a nucleic acid or a nanoparticle. A small chemical molecule may be less than 1,000 Da, peptides may have molecular weights about 5,000 Da, siRNA may have molecular weights around 15,000 Da, antibodies may have molecular weights of about 150,000 Da and DNA may have molecular weights of greater than or equal to 5,000,000 Da. In preferred embodiments, the payload comprises mRNA.

According to example methods, the payload includes 3.0-150.0 µM of a molecule to be delivered, more preferably, 6.6-150.0 µM molecule to be delivered (e.g. 3.0, 3.3, 6.6, or 150.0 µM molecule to be delivered). In some implementations, the payload to be delivered has an average molecular weight of up to 15,000 Da, and the payload includes 3.3 µM molecules to be delivered.

According to example methods, the payload to be delivered has an average molecular weight of up to 15,000 Da, and the payload includes 6.6 µM to be delivered. In some implementations, the payload to be delivered has an average molecular weight of up to 1,000 Da, and the payload includes 150.0 µM to be delivered.

According to further aspects of the present subject matter, a method for delivering molecules of more than one molecular weight across a plasma membrane is provided; the method including the steps of: introducing the molecules of more than one molecular weight to an aqueous solution; and contacting the aqueous solution with a plasma membrane.

In some implementations, the method includes introducing a first molecule having a first molecular weight and a second molecule having a second molecular weight to the payload, wherein the first and second molecules may have different molecular weights, or wherein, the first and second molecules may have the same molecular weights. According to example methods, the first and second molecules may be different molecules.

In some implementations, the payload to be delivered may include a therapeutic agent, or a diagnostic agent, including, for example, cisplatin, aspirin, various statins (e.g., pitavastatin, atorvastatin, lovastatin, pravastatin, rosuvastatin, simvastatin, promazine HCl, chloropromazine HCl, thioridazine HCl, Polymyxin B sulfate, chloroxine, benfluorex HCl and phenazopyridine HCl), and fluoxetine. Other therapeutic agents include antimicrobials (aminoclyclosides (e.g. gentamicin, neomycin, streptomycin), penicillins (e.g., amoxicillin, ampicillin), glycopeptides (e.g., avoparcin, vancomycin), macrolides (e.g., erythromycin, tilmicosin, tylosin), quinolones (e.g., sarafloxacin, enrofloxin), streptogramins (e.g., viginiamycin, quinupristin-dalfoprisitin), carbapenems, lipopeptides, oxazolidinones, cycloserine, ethambutol, ethionamide, isoniazrid, para-aminosalicyclic acid, and pyrazinamide). In some examples, an anti-viral (e.g., Abacavir, Aciclovir, Enfuvirtide, Entecavir, Nelfinavir, Nevirapine, Nexavir, Oseltamivir Raltegravir, Ritonavir, Stavudine, and Valaciclovir). The therapeutic may include a protein-based therapy for the treatment of various diseases, e.g., cancer, infectious diseases, hemophilia, anemia, multiple sclerosis, and hepatitis B or C.

Additional exemplary payloads can also include detectable markers or labels such as methylene blue, Patent blue V, and Indocyanine green.

The methods described herein may also include the payload including of a detectable moiety, or a detectable nanoparticle (e.g., a quantum dot). The detectable moiety may include a fluorescent molecule or a radioactive agent (e.g., $^{125}$I). When the fluorescent molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthaldebyde and fluorescamine. The molecule can also be detectably labeled using fluorescence emitting metals such as $^{152}$Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

In additional embodiments, the payload to be delivered may include a composition that edits genomic DNA (i.e., gene editing tools). For example, the gene editing composition may include a compound or complex that cleaves, nicks, splices, rearranges, translocates, recombines, or otherwise alters genomic DNA. Alternatively or in addition, a gene editing composition may include a compound that (i) may be included a gene-editing complex that cleaves, nicks, splices, rearranges, translocates, recombines, or otherwise alters genomic DNA; or (ii) may be processed or altered to be a compound that is included in a gene-editing complex that cleaves, nicks, splices, rearranges, translocates, recombines, or otherwise alters genomic DNA. In various embodiments, the gene editing composition comprises one or more of (a) gene editing protein; (b) RNA molecule; and/or (c) ribonucleoprotein (RNP).

In some embodiments, the gene editing composition comprises a gene editing protein, and the gene editing protein is a zinc finger nuclease (ZEN), a transcription activator-like effector nuclease (TALEN), a Cas protein, a Cre recombinase, a Hin recombinase, or a Flp recombinase. In additional embodiments, the gene editing protein may be a fusion proteins that combine homing endonucleases with the modular DNA binding domains of TALENs (megaTAL). For example, megaTAL may be delivered as a protein or alternatively, a mRNA encoding a megaTAL protein is delivered to the cells.

In various embodiments, the gene editing composition comprises a RNA molecule, and the RNA molecule comprises a sgRNA, a crRNA, and/or a tracrRNA.

In certain embodiments, the gene editing composition comprises a RNP, and the RNP comprises a Cas protein and a sgRNA or a crRNA and a tracrRNA. Aspects of the present subject matter are particularly useful for controlling when and for how long a particular gene-editing compound is present in a cell.

In various implementations of the present subject matter, the gene editing composition is detectable in a population of cells, or the progeny thereof, for (a) about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution, or (b) less than about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution.

In some embodiments, the genome of cells in the population of cells, or the progeny thereof, comprises at least one site-specific recombination site for the Cre recombinase, Hin recombinase, or Flp recombinase.

Aspects of the present invention relate to cells that comprise one gene editing compound, and inserting another gene editing compound into the cells. For example, one component of an RNP could be introduced into cells that express or otherwise already contain another component of the RNP. For example, cells in a population of cells, or the progeny thereof, may comprise a sgRNA, a crRNA, and/or a tracrRNA. In some embodiments the population of cells, or the progeny thereof, expresses the sgRNA, crRNA, and/or tracrRNA. Alternatively or in addition, cells in a population of cells, or the progeny thereof, express a Cas protein.

Various implementations of the subject matter herein include a Cas protein. In some embodiments, the Cas protein is a Cas9 protein or a mutant thereof. Exemplary Cas proteins (including Cas9 and non-limiting examples of Cas9 mutants) are described herein.

In various aspects, the concentration of Cas9 protein may range from about 0.1 to about 25 µg. For example, the concentration of Cas9 may be about 1 µg, about 5 µg, about 10 µg, about 15 µg, or about 20 µg. Alternatively, the concentration of Cas9 may range from about 10 ng/µL to about 300 ng/µL; for example from about 10 ng/µL to about 200 ng/µl; or from about 10 ng/µL to about 100 ng/µl, or from about 10 ng/µL to about 50 ng/µl.

In certain embodiments, the gene editing composition comprises (a) a first sgRNA molecule and a second sgRNA molecule, wherein the nucleic acid sequence of the first sgRNA molecule is different from the nucleic acid sequence of the second sgRNA molecule; (b) a first RNP comprising a first sgRNA and a second RNP comprising a second sgRNA, wherein the nucleic acid sequence of the first sgRNA molecule is different from the nucleic acid sequence of the second sgRNA molecule; (c) a first crRNA molecule and a second crRNA molecule, wherein the nucleic acid sequence of the first crRNA molecule is different from the nucleic acid sequence of the second crRNA molecule; (d) a first crRNA molecule and a second crRNA molecule, wherein the nucleic acid sequence of the first crRNA molecule is different from the nucleic acid sequence of the second crRNA molecule, and further comprising a tracrRNA molecule; or (e) a first RNP comprising a first crRNA and a tracrRNA and a second RNP comprising a second crRNA and a tracrRNA, wherein the nucleic acid sequence of the first crRNA molecule is different from the nucleic acid sequence of the second crRNA molecule.

In aspects, the ratio of the Cas9 protein to guide RNA may be 1:1, 1:2, 1:3, 1:4, 1:5, 1:6, 1:7, 1:8, 1:9, or 1:10.

In embodiments, increasing the number of times that cells go through the delivery process (alternatively, increasing the number of doses), may increase the percentage edit; wherein, in some embodiments the number of doses may include 1, 2, 3, 4, 5, 6, 7, 8, 9, or 10 doses.

In various embodiments, the first and second sgRNA or first and second crRNA molecules together comprise nucleic acid sequences complementary to target sequences flanking a gene, an exon, an intron, an extrachromosomal sequence, or a genomic nucleic acid sequence, wherein the gene, an exon, intron, extrachromosomal sequence, or genomic nucleic acid sequence is about 1, 2, 3, 4, 5, 6, 10, 20, 30, 40, 50, 60, 70, 80, 90, 100, 1-100, kilobases in length or is at least about 1, 2, 3, 4, 5, 6, 10, 20, 30, 40, 50, 60, 70, 80, 90, 100, 1-100, kilobases in length. In some embodiments, the use of pairs of RNPs comprising the first and second sgRNA or first and second crRNA molecules may be used to create a polynucleotide molecule comprising the gene, exon, intron, extrachromosomal sequence, or genomic nucleic acid sequence.

In certain embodiments, the target sequence of a sgRNA or crRNA is about 12 to about 25, or about 12, 13, 14, 15, 16, 17, 18, 19, 20, 21, 22, 23, 24, 25, 17-23, or 18-22, nucleotides long. In some embodiments, the target sequence is 20 nucleotides long or about 20 nucleotides long.

In various embodiments, the first and second sgRNA or first and second crRNA molecules are complementary to sequences flanking an extrachromosomal sequence that is within an expression vector.

Aspects of the present subject matter relate to the delivery of multiple components of a gene-editing complex, where the multiple components are not complexed together. In some embodiments, gene editing composition comprises at least one gene editing protein and at least one nucleic acid, wherein the gene editing protein and the nucleic acid are not bound to or complexed with each other.

The present subject matter allows for high gene editing efficiency while maintaining high cell viability. In some embodiments, at least about 10, 20, 30, 40, 50, 60, 70, 80, 90, 95, 99%, 1-99%, or more of the population of cells, or the progeny thereof, become genetically modified after contact with the aqueous solution. In various embodiments, at least about 10, 20, 30, 40, 50, 60, 70, 80, 90, 95, 99%, 1-99%, or more of the population of cells, or the progeny thereof, are viable after contact with the aqueous solution.

In certain embodiments, the gene editing composition induces single-strand or double-strand breaks in DNA within the cells. In some embodiments the gene editing composition further comprises a repair template polynucleotide. In various embodiments, the repair template comprises (a) a first flanking region comprising nucleotides in a sequence complementary to about 40 to about 90 base pairs on one side of the single or double strand break and a second flanking region comprising nucleotides in a sequence complementary to about 40 to about 90 base pairs on the other side of the single or double strand break; or (b) a first flanking region comprising nucleotides in a sequence complementary to at least about 20, 25, 30, 35, 40, 45, 50, 60, 70, 80, or 90 base pairs on one side of the single or double strand break and a second flanking region comprising nucleotides in a sequence complementary to at least about 20, 25, 30, 35, 40, 45, 50, 60, 70, 80, or 90 base pairs on the other side of the single or double strand break. Non-limiting descriptions relating to gene editing (including repair templates) using the CRISPR-Cas system are discussed in Ran et al. (2013) Nat Protoc. 2013 November; 8 (11): 2281-2308, the entire content of which is incorporated herein by reference. Embodiments involving repair templates are not limited to those comprising the CRISPR-Cas system.

In various implementations of the present subject matter, the volume of aqueous solution is delivered to the population of cells in the form of a spray. In some embodiments, the volume is between $6.0 \times 10^{-7}$ microliter per cell and $7.4 \times 10^{-4}$ microliter per cell. In certain embodiments, the spray comprises a colloidal or sub-particle comprising a diameter of 10 nm to 100 µm. In various embodiments, the volume is between $2.6 \times 10^{-9}$ microliter per square micrometer of exposed surface area and $1.1 \times 10^{-6}$ microliter per square micrometer of exposed surface area.

In some embodiments, the RNP has a size of approximately 100 Å×100 Å×50 Å or 10 nm×10 nm×5 nm. In various embodiments, the size of spray particles is adjusted to accommodate at least about 1, 2, 3, 4, 5, 6, 7, 8, 9, 10, or more RNPs per spray particle.

For example, contacting the population of cells with the volume of aqueous solution may be performed by gas propelling the aqueous solution to form a spray. In certain embodiments, the population of cells is in contact with said aqueous solution for 0.01-10 minutes (e.g., 0.1-10 minutes) prior to adding a second volume of buffer or culture medium to submerse or suspend said population of cells.

In various embodiments, the population of cells includes at least one of primary or immortalized cells. For example, the population of cells may include mesenchymal stem cells, lung cells, neuronal cells, fibroblasts, human umbilical vein (HUVEC) cells, and human embryonic kidney (HEK) cells, primary or immortalized hematopoietic stem cell (HSC), T cells, natural killer (NK) cells, cytokine-induced killer (CIK) cells, human cord blood CD34+ cells, B cells. Non limiting examples of T cells may include CD8+ or CD4+ T cells. In some aspects, the CD8+ subpopulation of the CD3$^+$ T cells are used. CD8$^+$ T cells may be purified from the PBMC population by positive isolation using anti-CD8 beads. In some aspects primary NK cells are isolated from PBMCs and GFP mRNA may be delivered by platform delivery technology (i.e., 3% expression and 96% viability at 24 hours). In additional aspects, NK cell lines, e.g., NK92 may be used.

Cell types also include cells that have previously been modified for example T cells, NK cells and MSC to enhance their therapeutic efficacy. For example: T cells or NK cells that express chimeric antigen receptors (CAR T cells, CAR NK cells, respectively); T cells that express modified T cell receptor (TCR); MSC that are modified virally or non-virally to overexpress therapeutic proteins that complement their innate properties (e.g. delivery of Epo using lentiviral vectors or BMP-2 using AAV-6) (reviewed in Park et al, Methods, 2015 August; 84-16.); MSC that are primed with non-peptidic drugs or magnetic nanoparticles for enhanced efficacy and externally regulated targeting respectively (Park et al., 2015); MSC that are functionalised with targeting moieties to augment their homing toward therapeutic sites using enzymatic modification (e.g. Fucosyltransferase), chemical conjugation (eg. modification of SLeX on MSC by using N-hydroxy-succinimide (NHS) chemistry) or non-covalent interactions (eg. engineering the cell surface with palmitated proteins which act as hydrophobic anchors for subsequent conjugation of antibodies) (Park et al., 2015). For example, T cells, e.g., primary T cells or T cell lines, that have been modified to express chimeric antigen receptors (CAR T cells) may further be treated according to the invention with gene editing proteins and or complexes containing guide nucleic acids specific for the CAR encoding sequences for the purpose of editing the gene(s) encoding the CAR, thereby reducing or stopping the expression of the CAR in the modified T cells.

Aspects of the present invention relate to the expression vector-free delivery of gene editing compounds and complexes to cells and tissues, such as delivery of Cas-gRNA ribonucleoproteins for genome editing in primary human T cells, hematopoietic stem cells (HSC), and mesenchymal stromal cells (MSC). In some example, mRNA encoding such proteins are delivered to the cells.

Various aspects of the CRISPR-Cas system are known in the art. Non-limiting aspects of this system are described, e.g., in U.S. Pat. No. 9,023,649, issued May 5, 2015; U.S. Pat. No. 9,074,199, issued Jul. 7, 2015; U.S. Pat. No. 8,697,359, issued Apr. 15, 2014; U.S. Pat. No. 8,932,814, issued Jan. 13, 2015; PCT International Patent Application Publication No. WO 2015/071474, published Aug. 27, 2015; Cho et al., (2013) Nature Biotechnology Vol 31 No 3 pp 230-232 (including supplementary information); and Jinek et al., (2012) Science Vol 337 No 6096 pp 816-821, the entire contents of each of which are incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2 and in the NCBI database as under accession number Q99ZW2.1. UniProt database accession numbers A0A0G4DEU5 and CDJ55032 provide another example of a Cas9 protein amino acid sequence. Another non-limiting example is a *Streptococcus thermophilus* Cas9 protein, the amino acid sequence of which may be found in the UniProt database under accession number Q03JI6.1. In some embodiments, the unmodified CRISPR enzyme has DNA cleavage activity, such as Cas9. In certain embodiments the CRISPR enzyme is Cas9, and may be Cas9 from *S. pyogenes* or *S. pneumoniae*. In various embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In certain embodiments, a Cas9 nickase may be used in combination with guide sequence(s), e.g., two guide sequences, which target respectively sense and antisense strands of the DNA target. This combination allows both strands to be nicked and used to induce NHEJ.

As a further example, two or more catalytic domains of Cas9 (RuvC I, RuvC II, and RuvC III) may be mutated to produce a mutated Cas9 substantially lacking all DNA cleavage activity. A D10A mutation may be combined with one or more of H840A, N854A, or N863A mutations to produce a Cas9 enzyme substantially lacking all DNA cleavage activity. In certain embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In certain embodiments, a protein being delivered (such as a Cas protein or a variant thereof) may include a subcellular localization signal. For example, the Cas protein within a RNP may comprise a subcellular localization signal. Depending on context, a fusion protein comprising, e.g., Cas9 and a nuclear localization signal may be referred to as "Cas9" herein without specifying the inclusion of the nuclear localization signal. In some embodiments, the payload (such as an RNP) comprises a fusion-protein that comprises a localization signal. For example, the fusion-protein may contain a nuclear localization signal, a nucleolar localization signal, or a mitochondrial targeting signal. Such signals are known in the art, and non-limiting examples are described in Kalderon et al., (1984) Cell 39 (3 Pt 2): 499-509; Makkerh et al., (1996) Curr Biol. 6 (8): 1025-7; Dingwall et al., (1991) Trends in Biochemical Sciences 16 (12): 478-81; Scott et al., (2011) BMC Bioinformatics 12:317 (7 pages); Omura T (1998) J Biochem. 123 (6): 1010-6; Rapaport D (2003) EMBO Rep. 4 (10): 948-52; and Brocard & Hartig (2006) Biochimica et Biophysica Acta (BBA)-Molecular Cell Research 1763 (12): 1565-1573, the contents of each of which are hereby incorporated herein by reference. In various embodiments, the Cas protein may comprise more than one localization signals, such as 2, 3, 4, 5, or more nuclear localization signals. In some embodiments, the localization signal is at the N-terminal end of the Cas protein and in other embodiments the localization signal is at the C-terminal end of the Cas protein.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis.

Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme corresponding to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, the degree of complementarity is 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, BLAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In certain embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

CRISPR-Cas technology which facilitates genome engineering in a wide range of cell types is evolving rapidly. It has recently been shown that delivery of the Cas9-gRNA editing tools in the form of ribonucleoproteins (RNPs) yields several benefits compared with delivery of plasmids encoding for Cas9 and gRNAs. Benefits include faster and more efficient editing, fewer off-target effects, and less toxicity. RNPs have been delivered by lipofection and electroporation but limitations that remain with these delivery methods, particularly for certain clinically relevant cell types, include toxicity and low efficiency. Accordingly, there is a need to provide a vector-free e.g., viral vector-free, approach for delivering biologically relevant payloads, e.g., RNPs, across a plasma membrane and into cells. "Cargo" or "payload" are terms used to describe a compound, or composition that is delivered via an aqueous solution across a cell plasma membrane and into the interior of a cell.

The current subject matter relates to delivery technology that facilitates delivery of a broad range of payloads to cells with low toxicity. Genome editing may be achieved by delivering RNPs to cells using some aspects of the current subject matter. Levels decline thereafter until Cas9 is no longer detectable. The delivery technology per se does not deleteriously affect the viability or functionality of Jurkat and primary T cells. The current subject matter enables gene editing via Cas9 RNPs in clinically relevant cell types with minimal toxicity.

The transient and direct delivery of CRISPR/Cas components such as Cas and/or a gRNA has advantages compared to expression vector-mediated delivery. For example, an amount of Cas, gRNA, or RNP can be added with more precise timing and for a limited amount of time compared to the use of an expression vector. Components expressed from a vector may be produced in various quantities and for variable amounts of time, making it difficult to achieve consistent gene editing without off-target edits. Additionally, pre-formed complexes of Cas and gRNAs (RNPs) cannot be delivered with expression vectors.

In one aspect, the present subject matter describes cells attached to a solid support, (e.g., a strip, a polymer, a bead, or a nanoparticle). The support or scaffold may be a porous or non-porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present subject matter. The support material may have virtually any possible structural configuration. Thus, the support configuration may be spherical, as in a bead, or cylindrical, as in the inside surface of a test tube, or the external surface of a rod. Alternatively, the surface may be flat such as a sheet, or test strip, etc. Preferred supports include polystyrene beads.

In other aspects, the solid support comprises a polymer, to which cells are chemically bound, immobilized, dispersed, or associated. A polymer support may be a network of polymers, and may be prepared in bead form (e.g., by suspension polymerization). The cells on such a scaffold can be sprayed with payload containing aqueous solution according to the invention to deliver desired compounds to the cytoplasm of the scaffold. Exemplary scaffolds include stents and other implantable medical devices or structures.

OTHER EMBODIMENTS

In the descriptions above and in the claims, phrases such as “at least one of” or “one or more of” may occur followed by a conjunctive list of elements or features. The term “and/or” may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases “at least one of A and B;” “one or more of A and B;” and “A and/or B” are each intended to mean “A alone, B alone, or A and B together.” A similar interpretation is also intended for lists including three or more items. For example, the phrases “at least one of A, B, and C;” “one or more of A, B, and C;” and “A, B, and/or C” are each intended to mean “A alone, B alone, C alone, A and B together, A and C together, B and C together, or A and B and C together.” In addition, use of the term “based on,” above and in the claims is intended to mean, “based at least in part on,” such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system comprising:

a housing configured to receive a filter plate comprising a well;

a differential pressure applicator configured to apply a differential pressure to the well;

a delivery solution applicator configured to deliver atomized delivery solution to the well;

a stop solution applicator configured to deliver a stop solution to the well; and a culture medium applicator configured to deliver a culture medium to the well.

2. The system of claim 1, wherein the housing comprises:

a chamber;

a lid disposed at a first end of the chamber; and a base disposed at a second end of the chamber, wherein the filter plate is disposed within the chamber.

3. The system of claim 2, wherein the differential pressure applicator is connected to the lid of the housing and includes a shower head, which includes a plurality of apertures at an end portion thereof.

4. The system of claim 2, wherein the stop solution applicator delivers the stop solution to the well through a septum provided in the lid of the housing.

5. The system of claim 2, wherein the culture medium applicator delivers the culture medium to the well through a septum provided in the lid of the housing or through a port of the chamber.

6. The system of claim 1, wherein the housing is configured to tilt the filter plate.

7. The system of claim 1, wherein the delivery solution applicator includes a robotic arm and spray head, the robotic arm magnetically coupled to the spray head.

8. The system of claim 7, further comprising a soft elastomeric barrier enclosing the filter plate and spray head, wherein the soft elastomeric barrier separates the robotic arm and the spray head.

9. The system of claim 7, wherein the robotic arm is configured to carry the spray head to a plurality of locations on the filter plate.

10. The system of claim 1, wherein the stop solution applicator and the culture medium applicator are formed integral within the housing as ports, and wherein the housing forms a vessel.

11. The system of claim 10, wherein the vessel includes a waste media outlet for collecting waste media.

12. The system of claim 1, further comprising a soft elastomeric barrier enclosing the filter plate and delivery solution applicator within the housing, the soft elastomeric barrier and the housing forming a bioreactor.

13. The system of claim 1, wherein the housing includes a filter plate base configured to tilt, rotate, and/or vibrate the filter plate.

14. The system of claim 1, wherein the delivery solution applicator includes a robotic arm and spray head, and the spray head is a single-use cartridge.

15. The system of claim 1, wherein the filter plate is sized to hold greater than $1\times10^7$ T cells.

16. The system of claim 1, wherein the system is configured to automatically:
provide to the filter plate cells in media;
remove culture media to form a cellular monolayer on top of the filter plate;
apply an atomized delivery solution to the cellular monolayer;

incubate the cells, apply a stop solution to the incubated cellular monolayer; and provide new media to the cellular monolayer.

17. The system of claim 16, wherein the system is configured to automatically tilt, vibrate, and/or rotate the filter plate to re-suspend the cells in the new media.

18. The system of claim 16, wherein the system is configured to repeat the application of the atomized delivery solution, the incubation, and the application of the stop solution.

19. The system of claim 1, wherein the delivery solution applicator includes a nebulizer.

20. The system of claim 19, wherein the delivery solution applicator further includes a mass flow controller or a volumetric flow controller to regulate a gas flow to operate the nebulizer.

21. The system of claim 1, wherein the delivery solution applicator is configured to deliver 10-300 micro liters of the delivery solution per actuation.

22. The system of claim 1, further comprising a temperature control system configured to control a temperature of the delivery solution and/or of the plate comprising the well.

23. The system of claim 1, wherein the delivery solution includes an aqueous solution, the aqueous solution including the payload and an alcohol at greater than 2 percent (v/v) concentration.

24. The system of claim 23, wherein said alcohol comprises ethanol.

25. The system of claim 23, wherein said aqueous solution comprises greater than 5% ethanol.

26. The system of claim 23, wherein said aqueous solution comprises between 5-30% ethanol.

27. The system of claim 23, wherein said aqueous solution comprises 12% or 25% ethanol.

28. The system of claim 23, wherein said aqueous solution comprises between 12.5-500 mM KCl.

29. The system of claim 23, wherein said aqueous solution comprises 106 mM KCl.

30. The system of claim 1, further comprising:
the filter plate, wherein the well is configured to contain a population of non-adherent cells.

31. The system of claim 30, wherein said non-adherent cell comprises a peripheral blood mononuclear cell.

32. The system of claim 30, wherein said non-adherent cell comprises an immune cell.

33. The system of claim 30, wherein said non-adherent cell comprises a T lymphocyte.

34. The system of claim 23, wherein said payload comprises a messenger ribonucleic acid (mRNA).

35. The system of claim 34, wherein said mRNA encodes a gene-editing composition.

36. The system of claim 35, wherein said gene editing composition reduces the expression of PD-1.

37. The system of claim 34, wherein said mRNA encodes a chimeric antigen receptor.

38. The system of claim 1 for use to deliver a cargo compound or composition to a mammalian cell.

39. The system of claim 30, wherein said population of non-adherent cells comprises a monolayer.

* * * * *